(12) United States Patent
Maeda et al.

(10) Patent No.: US 9,061,959 B2
(45) Date of Patent: Jun. 23, 2015

(54) METHOD FOR MANUFACTURING OPTICALLY ACTIVE MENTHOL

(75) Inventors: Hironori Maeda, Kanagawa (JP); Hisanori Itoh, Kanagawa (JP); Shinya Yamada, Kanagawa (JP); Yoji Hori, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 110 days.

(21) Appl. No.: 13/990,872

(22) PCT Filed: Dec. 1, 2011

(86) PCT No.: PCT/JP2011/077857
§ 371 (c)(1),
(2), (4) Date: May 31, 2013

(87) PCT Pub. No.: WO2012/074075
PCT Pub. Date: Jun. 7, 2012

(65) Prior Publication Data
US 2013/0253228 A1    Sep. 26, 2013

(30) Foreign Application Priority Data

Dec. 1, 2010    (JP) ................................. 2010-268633

(51) Int. Cl.
| | | |
|---|---|---|
| C07C 29/132 | (2006.01) | |
| C07B 53/00 | (2006.01) | |
| C07C 29/17 | (2006.01) | |
| C07C 29/56 | (2006.01) | |
| B01J 31/18 | (2006.01) | |
| B01J 31/26 | (2006.01) | |
| B01J 21/18 | (2006.01) | |
| B01J 23/44 | (2006.01) | |

(52) U.S. Cl.
CPC .............. *C07C 29/132* (2013.01); *C07B 53/00* (2013.01); *C07C 29/17* (2013.01); *C07C 29/56* (2013.01); *C07B 2200/07* (2013.01); *C07C 2101/14* (2013.01); *B01J 21/18* (2013.01); *B01J 23/44* (2013.01)

(58) Field of Classification Search
CPC ........ C07C 29/132; C07C 35/08; C07C 1/22; C07C 35/12
USPC ......................................... 568/861, 903, 830
See application file for complete search history.

(56) References Cited

U.S. PATENT DOCUMENTS

| | | | |
|---|---|---|---|
| 5,300,706 A | 4/1994 | Immel et al. | |
| 5,756,864 A | 5/1998 | Darsow et al. | |
| 6,342,644 B1 | 1/2002 | Sayo et al. | |
| 6,887,820 B1 * | 5/2005 | Ikariya et al. | ................. 502/155 |
| 2002/0133046 A1 | 9/2002 | Iwata et al. | |
| 2008/0139852 A1 | 6/2008 | Bergner et al. | |
| 2008/0167504 A1 | 7/2008 | Friedrich et al. | |
| 2008/0269528 A1 | 10/2008 | Jakel et al. | |
| 2010/0249467 A1 | 9/2010 | Heydrich et al. | |
| 2010/0324338 A1 * | 12/2010 | Maeda et al. | ................. 568/433 |
| 2011/0082308 A1 | 4/2011 | Itoh et al. | |
| 2011/0257412 A1 | 10/2011 | Itoh et al. | |
| 2011/0295031 A1 | 12/2011 | Itoh et al. | |
| 2011/0319638 A1 | 12/2011 | Itoh et al. | |

FOREIGN PATENT DOCUMENTS

| | | |
|---|---|---|
| EP | 0563611 A1 | 10/1993 |
| EP | 0743295 A1 | 11/1996 |
| JP | 2002-212121 A | 7/2002 |
| JP | 2008-515843 A | 5/2008 |
| JP | 2008-521763 A | 6/2008 |
| JP | 2008-538101 A | 10/2008 |
| JP | 2011-246366 A | 12/2011 |
| WO | 2009-068444 A2 | 6/2009 |
| WO | 2009-144906 A1 | 12/2009 |
| WO | 2010-071227 A1 | 6/2010 |
| WO | 2010-071231 A1 | 6/2010 |
| WO | 2010-140636 A1 | 12/2010 |

OTHER PUBLICATIONS

Geiger, et al.; "Cobalt (II)-Azabis (Oxazoline)-Catalyzed Conjugate Reduction of α,β-Unsaturate Carbnyl Compounds"; Advanced Synt Catal; 2005; 349; pp. 249-254.

Akutagawa; "Enantioselective Isomerization of Allylamine to Enamine: Practical Asymmetric Synthesis of (−)-Menthol by Rh-Binap Catalysts"; Topics in Catalysis 4; 1997; pp. 271-274.

Trasarti; et al.; "Design of Catalyst Systems Fo R the One-Pot Synthesis of Menthols From Citral"; Journal of Catalysis vol. 247; 2007; pp. 155-165.

Virtanen, et al.; "Towards One-Pot Synthesis of Menthols From Citral: Modifying Supported Ionic Liquid Catalysts (SILCAs) With Lewis and Brønsted Acids"; Journal of Catalysis vol. 263; 2009; pp. 209-219.

International Search Report (ISR) (PCT/ISA/210) issued Mar. 6, 2012 in corresponding International Application No. PCT/JP2011/077857.

Written Opinion (PCT/ISA/237) issued Mar. 6, 2012 in corresponding International Application No. PCT/JP2011/077857.

* cited by examiner

*Primary Examiner* — Jafar Parsa
*Assistant Examiner* — Medhanit Bahta
(74) *Attorney, Agent, or Firm* — Sughrue Mion, PLLC

(57) ABSTRACT

An object of the present invention is to provide a method for manufacturing an optically active menthol having fewer steps, which generates less environmentally polluting waste because a catalytic reaction is involved in all of the steps, and is capable of saving a production cost. The present invention relates to a method for manufacturing an optically active menthol, including the following steps: A-1) asymmetrically hydrogenating at least one of geranial and neral to thereby obtain an optically active citronellal, B-1) conducting a ring-closure reaction of the optically active citronellal in the presence of an acid catalyst to thereby obtain an optically active isopulegol, and C-1) hydrogenating the optically active isopulegol to thereby obtain an optically active menthol.

9 Claims, 4 Drawing Sheets

METHOD FOR MANUFACTURING OPTICALLY ACTIVE MENTHOL

TECHNICAL FIELD

The present invention particularly relates to a method for manufacturing an optically active menthol which includes a smaller number of steps and is therefore economically advantageous. More specifically, the present invention relates to a method for manufacturing an optically active menthol by selectively asymmetrically hydrogenating an α,β-unsaturated carbon-carbon double bond of geranial, neral, or citral (a mixture of geranial and neral in any ratio) to thereby obtain an optically active citronellal, converting the resulting optically active citronellal into an optically active isopulegol in the presence of an aluminum catalyst, and hydrogenating the resulting optically active isopulegol as is or after deep cooling crystallization.

BACKGROUND ART

Menthol is one of most important flavor or fragrance substances providing a cooling sensation. In most cases, however, it has still been isolated from natural supply sources by crystallization. In addition to natural menthol, in order to produce 1-menthol ((1R,2S,5R)-menthol) on an industrial scale, it is necessary to enhance the economy of its synthesis process as much as possible. For this purpose, particularly the synthesis of 1-menthol from inexpensive achiral raw materials is a problem to be solved.

This 1-menthol can be synthesized according to two concepts. According to one of the concepts, it is produced by esterifying racemic menthol obtained, for example, by hydrogenation of thymole, followed by racemic resolution (by crystallization or enzymatic resolution) (refer to Patent Documents 1 and 2).

According to the other concept, S. Akutagawa describes the synthesis of 1-menthol by enantioselective isomerization from allylamine to enamine by using rhodium-BINAP (BINAP=2,2'-bis(diphenylphosphino)-1,1'-binaphthyl) as a catalyst (refer to Non-patent Document 1).

On the other hand, there is disclosed a method of asymmetrically synthesizing 1-menthol including, as an important stage thereof, enantioselective hydrogenation of piperitenone (refer to Patent Document 3).

There is also disclosed a method for manufacturing an optically active menthol from geraniol, nerol, or a mixture of geraniol and nerol, including a) asymmetrically hydrogenating geraniol, nerol, or a mixture of geraniol and nerol to thereby obtain an optically active citronellol, b) oxidizing the resulting optically active citronellol to thereby obtain an optically active citronellal, c) conducting a ring-closure of the resulting optically active citronellal to thereby obtain a mixture containing an optically active isopulegol, and taking out the optically active isopulegol from the resulting mixture, and then, d) hydrogenating it to thereby obtain an optically active menthol (refer to Patent Document 4).

There is also disclosed a method for manufacturing optically active menthol from geranial, neral, or a mixture of geranial and neral, including a) subjecting citral (a mixture of geranial and neral) to precision distillation to thereby obtain geranial or neral, b) asymmetrically hydrogenating the resulting geranial or neral to thereby obtain an optically active citronellal, c) conducting a ring-closure of the resulting optically active citronellal to thereby obtain a mixture containing an optically active isopulegol and taking out the optically active isopulegol from the resulting mixture, and then, d) hydrogenating it to thereby obtain an optically active menthol (refer to Patent Document 5).

Isopulegol is an important intermediate for synthesizing racemic menthol and optically active menthol. It is typically prepared by a ring-closing oxo-ene reaction of citronellal in the presence of a Lewis acid catalyst. It is typically obtained as a mixture of four diastereomers, that is, isopulegol, iso-isopulegol, neo-isopulegol, and neoiso-isopulegol. As a method of preparing isopulegol which is important among them with high selectivity, there is disclosed a method of ring-closing citronellal in the presence of an aluminum catalyst (refer to Patent Documents 6 to 10).

PRIOR ART DOCUMENTS

Patent Documents

Patent Document 1: European Patent No. 0743295
Patent Document 2: European Patent No. 0563611
Patent Document 3: U.S. Pat. No. 6,342,644
Patent Document 4: JP-T-2008-521763 (the term "JP-T" as used herein means a published Japanese translation of a PCT patent application)
Patent Document 5: WO 2009/068444
Patent Document 6: JP-A-2002-212121
Patent Document 7: JP-T-2008-538101
Patent Document 8: WO 2009/144906
Patent Document 9: WO 2010/071227
Patent Document 10: WO 2010/071231

Non-Patent Document

Non-patent Document 1: Topics in Catalysis 4 (1997) P271-274

SUMMARY OF THE INVENTION

Problems that the Invention is to Solve

Natural menthol has however a problem in its stable supply, because it is strongly affected by the weather. With regard to the dissolution of racemic menthol described in Patent Documents 1 and 2, a step of taking out 1-menthol, which is contained only in a small amount, from the other seven isomers needs a complex step. In the production method of 1-menthol with myrcene as a raw material which is described in Non-patent Document 1, on the other hand, a larger number of steps is included and in addition, an expensive homogeneous rhodium complex is used as a catalyst for isomerizing diethylgeranylamine into a corresponding optically active enamine. In the method of asymmetrically synthesizing 1-menthol by enantioselective hydrogenation of peperitenone, on the other hand, the piperitenone, which is a raw material, is not easily available, an expensive homogeneous system complex such as rhodium complex or ruthenium complex is used, and a hydrogenation reaction is conducted under high pressure.

The method for manufacturing an optically active menthol from geraniol, nerol, or a mixture of geraniol and nerol, described in Patent Document 4, includes a) asymmetrically hydrogenating geraniol, nerol, or a mixture of geraniol and nerol to thereby obtain an optically active citronellol, b) oxidizing the resulting optically active citronellol to thereby obtain an optically active citronellal, c) conducting the ring-closure of the resulting optically active citronellal to thereby obtain a mixture containing an optically active isopulegol and taking out the optically active isopulegol from the resulting mixture, and then, d) hydrogenating it to thereby obtain an optically active menthol. This method actually needs a larger number of steps because geraniol and nerol should be separated through precision distillation and expensive homogeneous catalysts for asymmetrically hydrogenating each of geraniol and nerol should be prepared separately in order to obtain d-citronellol ((R)-citronellol) which is a raw material necessary for the production of 1-menthol.

The method for manufacturing an optically active menthol, described in Patent Document 5, includes a) subjecting citral (a mixture of geranial and neral) to precision distillation to thereby obtain geranial or neral, b) asymmetrically hydrogenating the resulting geranial or neral to thereby obtain an optically active citronellal, c) conducting the ring-closure of the resulting optically active citronellal to thereby obtain a mixture containing an optically active isopulegol and taking out the optically active isopulegol from the resulting mixture, and then, d) hydrogenating it to thereby obtain an optically active menthol. This method needs precision distillation for taking out high-purity neral or geranial from geraniol, neral, or a mixture of geranial and neral. After the precision distillation, expensive rhodium catalysts having different chiralities for asymmetrically hydrogenating neral and geranial respectively should be prepared separately in order to obtain d-citronellal((R)-citronellal) which is a raw material necessary for the production of 1-menthol. In addition, asymmetric hydrogenation should be conducted under a high hydrogen pressure. This method therefore needs a larger number of steps.

Thus, any of the above-described methods have a problem and there is a demand for the development of a more convenient and efficient production method of an optically active menthol.

An object of the present invention is to provide a method for manufacturing an optically active menthol having fewer steps, which generates less environmentally polluting waste because a catalytic reaction is involved in all of the steps, and is capable of saving a production cost.

Means for Solving the Problems

The present inventors have carried out an extensive investigation with a view to overcoming the above-mentioned problems and as a result, have completed the following method.

The present invention embraces each of the following inventions.

[1] A method for manufacturing an optically active menthol, comprising the following steps:
A-1) asymmetrically hydrogenating at least one of geranial and neral to thereby obtain an optically active citronellal,
B-1) conducting a ring-closure reaction of the optically active citronellal in the presence of an acid catalyst to thereby obtain an optically active isopulegol, and
C-1) hydrogenating the optically active isopulegol to thereby obtain an optically active menthol.

[2] A method for manufacturing an optically active menthol, comprising the following steps:
A-2) asymmetrically hydrogenating citral containing geranial and neral at a molar ratio of from 90:10 to 10:90 to thereby obtain an optically active citronellal,
B-2) conducting a ring-closure reaction of the optically active citronellal in the presence of an acid catalyst to thereby obtain an optically active isopulegol, and
C-2) hydrogenating the optically active isopulegol to thereby obtain an optically active menthol.

[3] A method for manufacturing an optically active menthol, comprising the following steps:
A-3) asymmetrically hydrogenating at least one of geranial and neral to thereby obtain an optically active citronellal,
B-3) conducting a ring-closure reaction of the optically active citronellal in the presence of an acid catalyst to thereby obtain an optically active isopulegol,
D-3) recrystallizing the optically active isopulegol by deep cooling to thereby obtain the isopulegol having an increased purity, and
E-3) hydrogenating the optically active isopulegol obtained in step D-3 to thereby obtain an optically active menthol.

[4] A method for manufacturing an optically active menthol, comprising the following steps:
A-4) asymmetrically hydrogenating citral containing geranial and neral at a molar ratio of from 90:10 to 10:90 to thereby obtain an optically active citronellal,
B-4) conducting a ring-closure reaction of the optically active citronellal in the presence of an acid catalyst to thereby obtain an optically active isopulegol,
D-4) recrystallizing the optically active isopulegol by deep cooling to thereby obtain the isopulegol having an increased purity, and
E-4) hydrogenating the optically active isopulegol obtained in step D-4 to thereby obtain an optically active menthol.

[5] The method for manufacturing an optically active menthol according to [1], comprising the following steps:
A-5) asymmetrically hydrogenating at least one of geranial and neral to thereby obtain an optically active citronellal having an optical purity of from 70 to 99% e.e.,
B-5) conducting a ring-closure reaction of the optically active citronellal in the presence of an acid catalyst to thereby obtain an optically active isopulegol, and
C-5) hydrogenating the optically active isopulegol to thereby obtain an optically active menthol.

[6] The method for manufacturing an optically active menthol according to [2], comprising the following steps:
A-6) asymmetrically hydrogenating citral containing geranial and neral at a molar ratio of from 90:10 to 10:90 to thereby obtain an optically active citronellal having an optical purity of from 70 to 99% e.e.,
B-6) conducting a ring-closure reaction of the optically active citronellal in the presence of an acid catalyst to thereby obtain an optically active isopulegol, and
C-6) hydrogenating the optically active isopulegol to thereby obtain an optically active menthol.

[7] The method for manufacturing an optically active menthol according to [3], comprising the following steps:
A-7) asymmetrically hydrogenating at least one of geranial and neral to thereby obtain an optically active citronellal having an optical purity of from 70 to 99% e.e.,
B-7) conducting a ring-closure reaction of the optically active citronellal in the presence of an acid catalyst to thereby obtain an optically active isopulegol,
D-7) recrystallizing the optically active isopulegol by deep cooling to thereby obtain the isopulegol having an increased purity, and
E-7) hydrogenating the optically active isopulegol obtained in step D-7 to thereby obtain an optically active menthol.

[8] The method for manufacturing an optically active menthol according to [4], comprising the following steps:

A-8) asymmetrically hydrogenating citral containing geranial and neral at a molar ratio of from 90:10 to 10:90 to thereby obtain an optically active citronellal having an optical purity of from 70 to 99% e.e., B-8) conducting a ring-closure reaction of the optically active citronellal in the presence of an acid catalyst to thereby obtain an optically active isopulegol, D-8) recrystallizing the optically active isopulegol by deep cooling to thereby obtain the isopulegol having an increased purity, and E-8) hydrogenating the optically active isopulegol obtained in step D-8 to thereby obtain an optically active menthol.

[9] The method for manufacturing an optically active menthol according to [1], comprising the following steps:

A-9) asymmetrically hydrogenating at least one of geranial and neral to thereby obtain d-citronellal, B-9) conducting a ring-closure reaction of the d-citronellal in the presence of an acid catalyst to thereby obtain l-isopulegol, and C-9) hydrogenating the l-isopulegol to thereby obtain l-menthol.

[10] The method for manufacturing an optically active menthol according to [2], comprising the following steps:

A-10) asymmetrically hydrogenating citral containing geranial and neral at a molar ratio of from 90:10 to 10:90 to thereby obtain d-citronellal, B-10) conducting a ring-closure reaction of the d-citronellal in the presence of an acid catalyst to thereby obtain l-isopulegol, and C-10) hydrogenating the l-isopulegol to thereby obtain l-menthol.

[11] The method for manufacturing an optically active menthol according to [3], comprising the following steps:

A-11) asymmetrically hydrogenating at least one of geranial and neral to thereby obtain d-citronellal, B-11) conducting a ring-closure reaction of the d-citronellal in the presence of an acid catalyst to thereby obtain l-isopulegol, D-11) recrystallizing the l-isopulegol by deep cooling to thereby obtain the l-isopulegol having an increased purity; and E-11) hydrogenating the l-isopulegol obtained in step D-11 to thereby obtain l-menthol.

[12] The method for manufacturing an optically active menthol according to [4], comprising the following steps:

A-12) asymmetrically hydrogenating citral containing geranial and neral at a molar ratio of from 90:10 to 10:90 to thereby obtain d-citronellal, B-12) conducting a ring-closure reaction of the d-citronellal in the presence of an acid catalyst to thereby obtain l-isopulegol, D-12) recrystallizing the l-isopulegol by deep cooling to thereby obtain the l-isopulegol having an increased purity, and E-12) hydrogenating the l-isopulegol obtained in step D-12 to thereby obtain l-menthol.

[13] The method for manufacturing an optically active menthol according to [1], comprising the following steps:

A-13) asymmetrically hydrogenating at least one of geranial and neral to thereby obtain d-citronellal having an optical purity of from 70 to 99% e.e., B-13) conducting a ring-closure reaction of the d-citronellal in the presence of an acid catalyst to thereby obtain l-isopulegol having an optical purity of from 70 to 99% e.e., and C-13) hydrogenating the l-isopulegol to thereby obtain l-menthol having an optical purity of from 70 to 99% e.e.

[14] The method for manufacturing an optically active menthol according to [2], comprising the following steps:

A-14) asymmetrically hydrogenating citral containing geranial and neral at a molar ratio of from 90:10 to 10:90 to thereby obtain d-citronellal having an optical purity of from 70 to 99% e.e., B-14) conducting a ring-closure reaction of the d-citronellal in the presence of an acid catalyst to thereby obtain l-isopulegol having an optical purity of from 70 to 99% e.e., and C-14) hydrogenating the l-isopulegol to thereby obtain l-menthol having an optical purity of from 70 to 99% e.e.

[15] The method for manufacturing an optically active menthol according to [3], comprising the following steps:

A-15) asymmetrically hydrogenating at least one of geranial and neral to thereby obtain d-citronellal having an optical purity of from 70 to 99% e.e., B-15) conducting a ring-closure reaction of the d-citronellal in the presence of an acid catalyst to thereby obtain l-isopulegol having an optical purity of from 70 to 99% e.e., D-15) recrystallizing the l-isopulegol by deep cooling to thereby obtain l-isopulegol having an optical purity of from 98 to 100% e.e., and E-15) hydrogenating the l-isopulegol obtained in step D-15 to thereby obtain l-menthol having an optical purity of from 98 to 100% e.e.

[16] The method for manufacturing an optically active menthol according to [4], comprising the following steps:

A-16) asymmetrically hydrogenating citral containing geranial and neral at a molar ratio of from 90:10 to 10:90 to thereby obtain d-citronellal having an optical purity of from 70 to 99% e.e., B-16) conducting a ring-closure reaction of the d-citronellal in the presence of an acid catalyst to thereby obtain l-isopulegol having an optical purity of from 70 to 99% e.e., D-16) recrystallizing the l-isopulegol by deep cooling to thereby obtain l-isopulegol having an optical purity of from 98 to 100% e.e., and E-16) hydrogenating the l-isopulegol obtained in step D-16 to thereby obtain l-menthol having an optical purity of from 98 to 100% e.e.

[17] The method for manufacturing an optically active menthol according to any one of [1] to [16], wherein in the asymmetric hydrogenation reaction of step A, a hydrogen gas, and a catalyst containing: at least one of a transition metal; an optically active cyclic nitrogen-containing compound; and an acid, are used.

[18] The method for manufacturing an optically active menthol according to any one of [1] to [16], wherein in the asymmetric hydrogenation reaction of step A, a catalyst containing: a powder of at least one metal selected from metals belonging to Group 8 to Group 10 of the Periodic Table or a metal-supported substance in which at least one metal selected from metals belonging to Group 8 to Group 10 of the Periodic Table is supported on a support; an optically active cyclic nitrogen-containing compound represented by the following formula (1); and an acid, is used,

[Chem. 1]

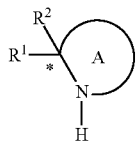
(1)

[in the formula (1), ring A is a 3- to 7-membered ring which may have a substituent group and contains at least one atom selected from the group consisting of carbon, nitrogen, sulfur, oxygen, and phosphorus, and ring A may be a fused ring structure; $R^1$ and $R^2$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amide group which may have a substituent group, a siloxy group which may have a substituent group, an aromatic heterocyclic group which may have a substituent group, or an aliphatic heterocyclic group which may have a substituent group, with the proviso that $R^1$ and $R^2$ do not represent a same substituent group; either $R^1$ or $R^2$ may be bonded to the ring A to form a ring; and * represents an asymmetric carbon atom].

[19] The method for manufacturing an optically active menthol according to any one of [1] to [16], wherein in the asymmetric hydrogenation reaction of step A, a catalyst containing: a powder of at least one metal selected from metals belonging to Group 8 to Group 10 of the Periodic Table or a metal-supported substance in which at least one metal selected from metals belonging to Group 8 to Group 10 of the Periodic Table is supported on a support; an optically active cyclic nitrogen-containing compound represented by the following formula (2); and an acid, is used,

[Chem. 2]

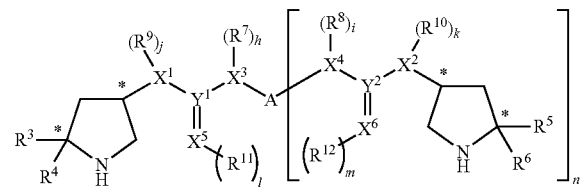
(2)

[in the formula (2), $R^3$, $R^4$, $R^5$, $R^6$, $R^7$, $R^8$, $R^9$, $R^{10}$, $R^{11}$, and $R^{12}$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amide group which may have a substituent group, a siloxy group which may have a substituent group, an aromatic heterocyclic group which may have a substituent group, or an aliphatic heterocyclic group which may have a substituent group, with the proviso that $R^3$ and $R^4$ represent substituent groups different from each other and $R^5$ and $R^6$ represent substituent groups different from each other;

h, i, j, k, l, and m each represent an integer of 0 or 1, n represents an integer of from 0 to 3; and * represents an asymmetric carbon atom;

A represents, when n is 0, a hydrogen atom, a hetero atom which may have a substituent group, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amide group which may have a substituent group, an aromatic heterocyclic group which may have a substituent group, an aliphatic heterocyclic group which may have a substituent group, an oligomer chain or a polymer chain; and A represents, when n is 1 to 3, a hetero atom which may have a substituent group, an alkylene group which may have a substituent group, an arylene group-containing alkylene group which may have a substituent group, a cycloalkylene group-containing alkylene group which may have a substituent group, a hetero atom-containing alkylene group which may have a substituent group, a divalent aliphatic hydrocarbon ring group which may have a substituent group, a divalent aliphatic heterocyclic group which may have a substituent group, a divalent aromatic hydrocarbon ring group which may have a substituent group, a divalent aromatic heterocyclic group which may have a substituent group, an oligomer chain or a polymer chain;

$R^7$ and $R^8$, $R^7$ and A, or $R^8$ and A may be bonded to each other to form a ring;

$X^1$, $X^2$, $X^3$, $X^4$, $X^5$, and $X^6$ each independently represent an oxygen atom, a nitrogen atom, a phosphorus atom or a sulfur atom; and $Y^1$ and $Y^2$ each independently represent a carbon atom, a silicon atom or a sulfur atom].

[20] The method for manufacturing an optically active menthol according to any one of [17] to [19], wherein the metal is selected from the group consisting of nickel, ruthenium, rhodium, iridium, palladium and platinum.

[21] The method for manufacturing an optically active menthol according to any one of [1] to [20], wherein the acid catalyst in the ring-closure reaction of the optically active citronellal in step B is a Lewis acid aluminum catalyst.

[22] The method for manufacturing an optically active menthol according to [21], wherein the Lewis acid aluminum catalyst is an organoaluminum compound obtained by reacting:

a trialkylaluminum represented by the following formula (3), with at least one compound selected from 2,6-diphenylphenol represented by the following formula (4), 2,6,2',6'-tetraphenyl-biphenyl-4,4'-diol represented by the following formula (5), 1,1'-binaphthyl-2,2'-diol represented by the following formula (6) which may be optically active, and (2,2-dimethyl-1,3-dioxolan-4,5-diyl)bis(diphenylmethanol) which may be optically active and is represented by the following formula (7):

[Chem. 3]

(3)

[in the formula (3), RP represents an alkyl group having from 1 to 8 carbon atoms].

[Chem. 4]

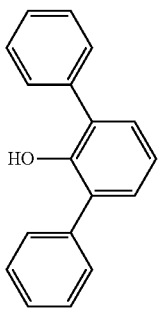
(4)

[Chem. 5]

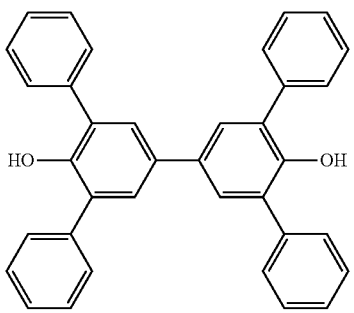
(5)

[Chem. 6]

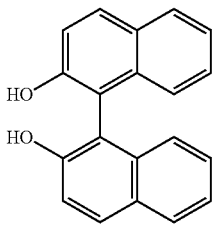
(6)

[Chem. 7]

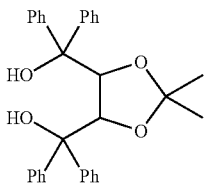
(7)

[23] The method for manufacturing an optically active menthol according to [21], wherein the Lewis acid aluminum catalyst is an organoaluminum catalyst obtained by reacting:

at least one organoaluminumoxy compound selected from a chain alminoxane represented by the following formula (8), a cyclic aluminoxane represented by the following formula (9) and a bis(dialkylaluminumoxy)alkylborane represented by the following formula (10), with at least one hydroxy compound selected from a diarylphenol represented by the following formula (11), a bis(diarylphenol) represented by the following formula (12), a biaryldiol represented by the following formula (13), a dimethanol represented by the following formula (14), and a silanol represented by the following formula (15):

[Chem. 8]

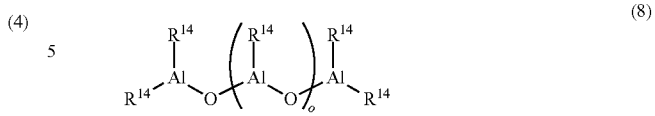
(8)

[in the formula (8), $R^{14}$ represents an alkyl group having from 1 to 6 carbon atoms, an alicyclic group having from 5 to 8 carbon atoms, or an aralkyl group which has from 7 to 12 carbon atoms and may have a substituent group, and a plurality of $R^{14}$ may be the same or different from each other; and o represents an integer of from 0 to 40];

[Chem. 9]

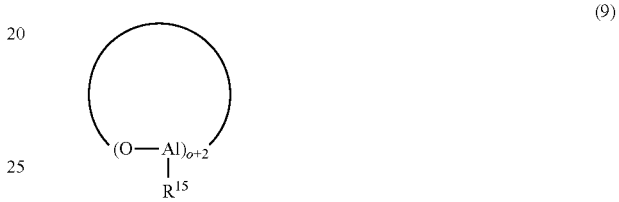
(9)

[in the formula (9), $R^{15}$ represents an alkyl group having from 1 to 6 carbon atoms, an alicyclic group having from 5 to 8 carbon atoms, or an aralkyl group which has from 7 to 12 carbon atoms and may have a substituent group; and o represents an integer of from 0 to 40];

[Chem. 10]

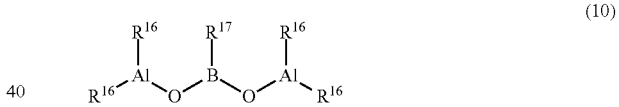
(10)

[in the formula (10), $R^{16}$ represents an alkyl group having from 1 to 6 carbon atoms, an alicyclic group having from 5 to 8 carbon atoms, or an aralkyl group which has from 7 to 12 carbon atoms and may have a substituent group, and a plurality of $R^{16}$ may be the same or different from each other; and $R^{17}$ represents an alkyl group having from 1 to 6 carbon atoms, an alicyclic group having from 5 to 8 carbon atoms, or an aralkyl group which has from 7 to 12 carbon atoms and may have a substituent group];

[Chem. 11]

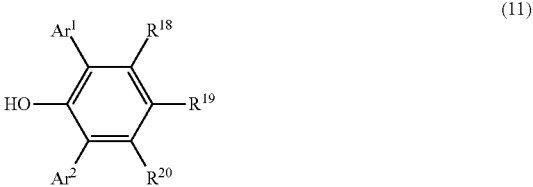
(11)

[in the formula (11), $Ar^1$ and $Ar^2$ each independently represent an aryl group which has from 6 to 15 carbon atoms and may have a substituent group or a heteroaryl group which has from 2 to 15 carbon atoms and may have a substituent group;

$R^{18}$, $R^{19}$, and $R^{20}$ each independently represent a hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group, or a polymer chain; and $R^{18}$ and $R^{19}$, or $R^{19}$ and $R^{20}$ may be bonded to each other to independently form a fused benzene ring, a fused substituted benzene ring, a trimethylene group, a tetramethylene group, a pentamethylene group, a methylenedioxy group, an ethylenedioxy group or a trimethylenedioxy group];

[Chem. 12]

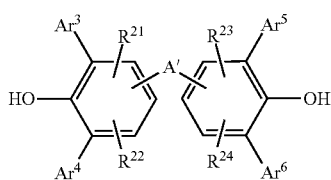

(12)

[in the formula (12), $Ar^3$, $Ar^4$, $Ar^5$, and $Ar^6$ each independently represent an aryl group which has from 6 to 15 carbon atoms and may have a substituent group or a heteroaryl group which has from 2 to 15 carbon atoms and may have a substituent group;

$R^{21}$, $R^{22}$, $R^{23}$ and $R^{24}$ each independently represent a hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group or a polymer chain; and $R^{21}$ and $R^{22}$, or $R^{23}$ and $R^{24}$ may be bonded to each other to independently form a fused benzene ring, a fused substituted benzene ring, a trimethylene group, a tetramethylene group, a pentamethylene group, a methylenedioxy group, an ethylenedioxy group or a trimethylenedioxy group; $R^{21}$ or $R^{22}$ and/or $R^{23}$ or $R^{24}$ may be bonded to A' to form an aromatic ring or a non-aromatic ring;

A' represents (1) a linear or branched and/or cyclic hydrocarbon group having from 1 to 25 carbon atoms, which may have at least one of a substituent group and an unsaturated bond; (2) an arylene group which has from 6 to 15 carbon atoms and may have a substituent group; (3) a heteroarylene group which has from 2 to 15 carbon atoms and may have a substituent group; or (4) a functional group or hetero element selected from the group consisting of —O—, —S—, —N($R^{25}$)—, —S(O)—, —C(O)—, —S(O)$_2$—, —P($R^{25}$)—, —($R^{25}$)P(O)— and —Si($R^{26}R^{27}$)— (wherein, $R^{25}$ to $R^{27}$ each independently represent an alkyl group having from 1 to 6 carbon atoms, an alicyclic group having from 5 to 8 carbon atoms, an aralkyl group which has from 7 to 12 carbon atoms and may have a substituent group, or an aryl group which has from 6 to 10 carbon atoms and may have a substituent group)];

[Chem. 13]

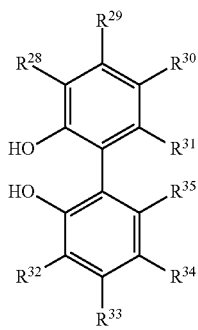

(13)

[in the formula (13), $R^{28}$, $R^{29}$, $R^{30}$, $R^{31}$, $R^{32}$, $R^{33}$, $R^{34}$, and $R^{35}$ each independently represent a hydrogen atom, an alkyl group having from 1 to 8 carbon atoms, a perfluoroalkyl group having from 1 to 4 carbon atoms, an alkoxy group having from 1 to 8 carbon atoms, an alicyclic group having from 5 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group or a polymer chain; and $R^{28}$ and $R^{29}$, $R^{29}$ and $R^{30}$, $R^{30}$ and $R^{31}$, $R^{31}$ and $R^{35}$, $R^{32}$ and $R^{33}$, $R^{33}$ and $R^{34}$, or $R^{34}$ and $R^{35}$ may be bonded to each other to independently form a fused benzene ring, a fused substituted benzene ring, a trimethylene group, a tetramethylene group, a pentamethylene group, a methylenedioxy group, an ethylenedioxy group, or a trimethylenedioxy group];

[Chem. 14]

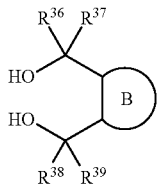

(14)

[in the formula (14), $R^{36}$, $R^{37}$, $R^{38}$, and $R^{39}$ each independently represent a hydrogen atom, an alkyl group having from 1 to 8 carbon atoms, an alicyclic group having from 5 to 8 carbon atoms, a perhalogenoalkyl group having from 1 to 8 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a heteroaryl group which has from 2 to 15 carbon atoms and may have a substituent group, a dialkylamino group having from 2 to 8 carbon atoms, a thioalkoxy group having from 1 to 4 carbon atoms, a nitro group or a polymer chain; and $R^{36}$ and $R^{37}$, and $R^{38}$ and $R^{39}$ may be bonded to each other to independently form a 3- to 9-membered ring which may have a hetero element; and ring B is a 3- to 8-membered ring which may have a hetero element];

[Chem. 15]

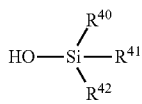
(15)

[in the formula (15), $R^{40}$, $R^{41}$, and $R^{42}$ each independently represent an alkyl group having from 1 to 10 carbon atoms, an alicyclic group having from 5 to 8 carbon atoms, an aralkyl group having from 7 to 12 carbon atoms, an aryl group which has from 6 to 10 carbon atoms and may have a substituent group, a heteroaryl group which has from 2 to 15 carbon atoms and may have a substituent group, or a polymer chain].

[24] The method for manufacturing an optically active menthol according to [21], wherein the Lewis acid aluminum catalyst is an organoaluminum catalyst obtained by reacting:

a chain aluminoxane represented by the following formula (8), with at least one compound selected from a 2,6-di-phenylphenol represented by the following formula (4), 2,6,2',6'-tetraphenyl-biphenyl-4,4'-diol represented by the following formula (5), and 1,1'-binaphthyl-2,2'-diol which may be optically active and is represented by the following formula (6):

[Chem. 16]

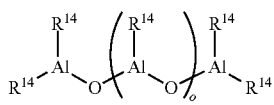
(8)

[in the formula (8), $R^{14}$ represents an alkyl group having from 1 to 6 carbon atoms, an alicyclic group having from 5 to 8 carbon atoms, or an aralkyl group which has from 7 to 12 carbon atoms and may have a substituent group; and a plurality of $R^{14}$ may be the same or different from each other; and o represents an integer of from 0 to 40].

[Chem. 17]

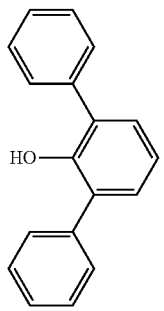
(4)

[Chem. 18]

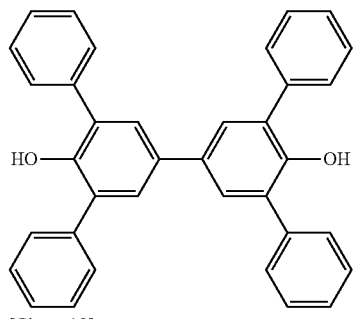
(5)

[Chem. 19]

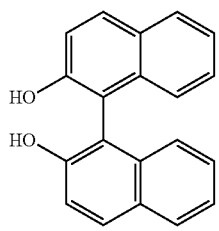
(6)

Effects of Invention

In the present invention, it is preferred to use, for obtaining an optically active menthol, a metal powder or a metal-supported substance, an optically active cyclic nitrogen-containing compound as an additive contributing to enantioselectivity, and an acid, as a catalyst in an asymmetric hydrogenation reaction of geranial, neral, or citral in a first-stage step.

Different from conventional asymmetric hydrogenation catalysts, the asymmetric hydrogenation catalyst in the present invention does not need a reaction step for preparing the catalyst. Asymmetric hydrogenation is conducted only by mixing a raw material compound, an optically active cyclic nitrogen-containing compound, a metal powder or a metal-supported substance, and an acid. Thus, using such a catalyst is industrially advantageous because the operation is simple and easy and in addition, the metal powder or metal-supported substance and the optically active cyclic nitrogen-containing compound can be recovered for re-use.

In the first-stage step of the production method of the present invention, an optically active citronellal is obtained by asymmetrically hydrogenating geranial, neral, or citral which is a mixture thereof. In either case where a Z-configuration compound (neral) or an E-configuration compound (geranial) in the double bond at the α-position or β-position of citral is used as a substrate, the steric configuration of the optically active citronellal thus obtained depends on the steric configuration of the optically active cyclic nitrogen-containing compound used as the catalyst. In the present invention, therefore, not only when only geranial or only neral is used as a substrate but also when a mixture of neral and geranial in any ratio is used as a substrate, optically active citronellals having the same configuration can be prepared.

Different from the asymmetric hydrogenation reaction in the previously disclosed report (Patent Document 5), the asymmetric hydrogenation reaction in the present invention can be conducted in a smaller number of steps, because it becomes unnecessary to separate cotral into geranial and neral through precision distillation and to subject the geranial or neral to asymmetrical hydrogenation.

In the second-stage step, an optically active isopulegol can be produced with high selectivity among four isomers by conducting a ring-closure of the optically active citronellal, which has been obtained in the first-stage step, in the presence of an aluminum catalyst.

In an optional third-stage step, the optically active isopulegol obtained in the second-stage step is subjected to deep cooling crystallization at low temperatures, making it possible to prepare an optically active citronellal with a higher chemical purity and optical purity.

In a fourth-stage step, the optically active citronellal obtained in the second-stage step or the optically active citronellal obtained in the third-stage step is hydrogenated in the presence of an ordinarily available hydrogenation catalyst to thereby manufacture an optically active menthol.

As a result, as the production methods of an optically active menthol by using chemical synthesis, an optically active menthol can be manufactured from raw materials with the fewest steps. In addition, all the production steps except deep cooling crystallization use a catalyst so that the method generates less environmentally polluting waste and can also save a production cost.

MODE FOR CARRYING OUT THE INVENTION

Figure 1:
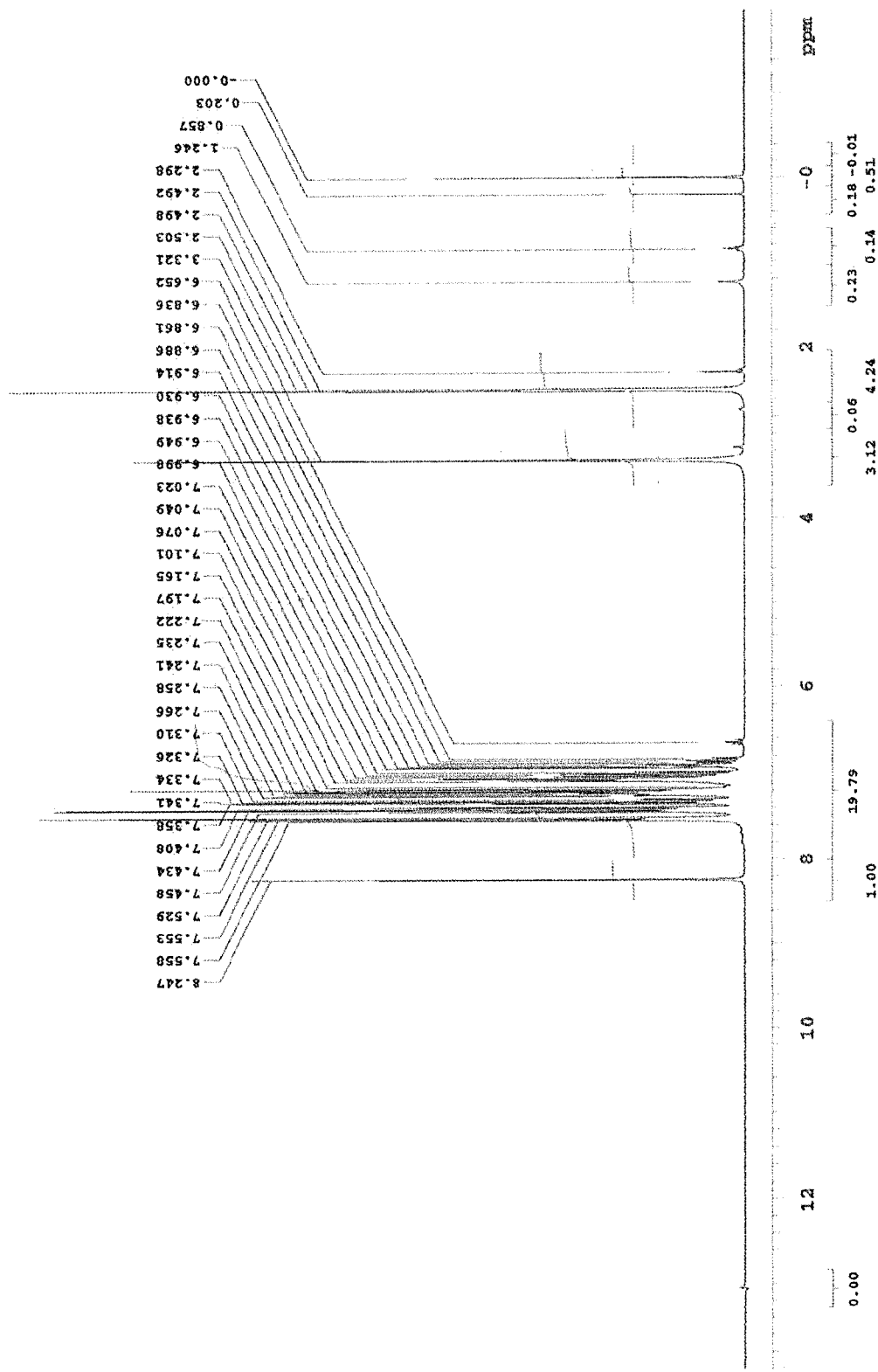
FIG. 1 is a chart showing the $^1$H-NMR spectrum of a reaction product of 2,6-diphenylphenol and methylaluminoxane.

The present invention will hereinafter be described in detail.

In the present application, the terms "wt %" and "part(s) by weight" have the same meanings as "mass %" and "part(s) by mass".

The production method of an optically active menthol according to the present invention is conducted as shown in Scheme 1. The symbol * means an asymmetric carbon.

(Scheme 1)

[Chem. 20]

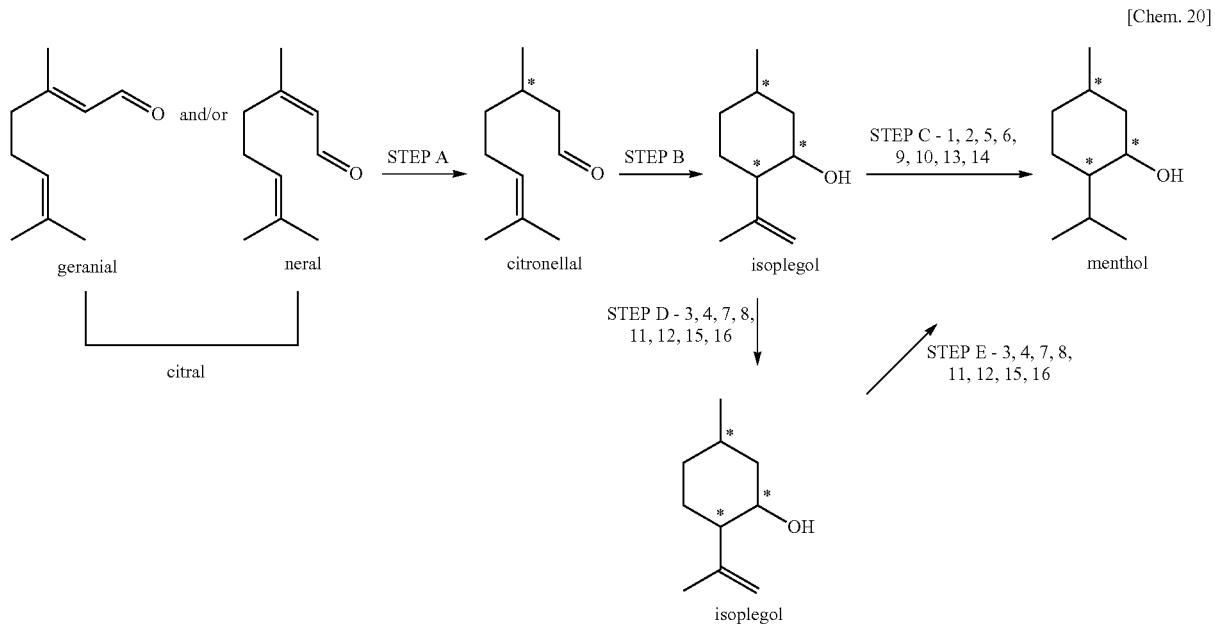

<Step A>

The step A shown in Scheme 1 of the present invention includes asymmetrically hydrogenating citral (a mixture of geranial and neral), geranial, or neral in the presence of an asymmetric hydrogenation catalyst to thereby prepare an optically active citronellal.

[Chem. 21]

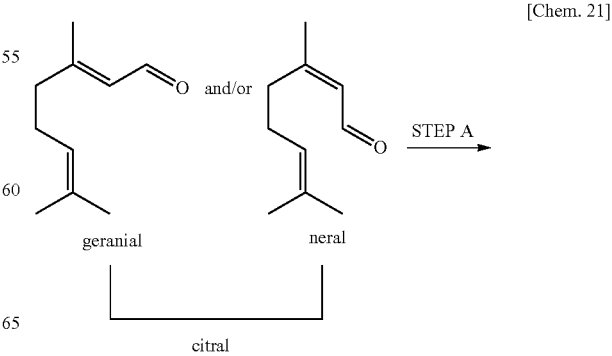

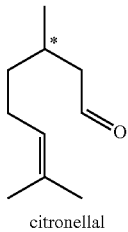

citronellal

Although a mixing ratio of geranial and neral in citral is arbitral and is not particularly limited, a molar ratio of geranial:neral is preferably within a range of from 90:10 to 10:90.

<Step A: Asymmetric Hydrogenation Catalyst>

Next, a description will be made on an asymmetric hydrogenation catalyst preferably used in the asymmetric hydrogenation reaction.

The asymmetric hydrogenation catalyst in the present invention is a catalyst for asymmetrically hydrogenating an α,β-unsaturated carbonyl compound and contains: a powder of at least one metal selected from metals belonging to Group 8 to Group 10 of the Periodic Table or a metal-supported substance in which at least one metal selected from metals belonging to Group 8 to Group 10 of the Periodic Table is supported on a support; an optically active cyclic nitrogen-containing compound; and an acid.

The powder of at least one metal selected from metals belonging to Group 8 to Group 10 of the Periodic Table or the metal-supported substance in which at least one metal selected from metals belonging to Group 8 to Group 10 of the Periodic Table is supported on a support, will next be described.

The metal belonging to Group 8 to Group 10 of the Periodic Table is preferably Ni (nickel), Ru (ruthenium), Rh (rhodium), Ir (iridium), Pd (palladium), and Pt (platinum), particularly preferably Pd.

Examples of the metal powder include Pd black and Pt black.

As the metal-supported substance, those obtained by supporting any of the above-mentioned metals on a support are used. Preferred examples include those obtained by supporting the above-mentioned metals on a support such as carbon, silica, alumina, silica-alumina, zeolite, metal oxide, metal halide, metal sulfide, metal sulfonate, metal nitrate, metal carbonate, or metal phosphate. Of these, the substance obtained by supporting palladium or platinum on the support is preferred.

As the metal-supported substance, illustrative examples thereof include Raney nickel, Ru/C, Rh/C, Pd/C, Ir/C, Pt/C, Pd/C(en) (palladium/carbon-ethylendiamine complex), Pd/Fib (palladium-fibroin), Pd/PEI (palladium-polyethyleneimine), $Pd/Al_2O_3$, $Pd/SiO_2$, $Pd/TiO_2$, $Pd/ZrO_2$, $Pd/CeO_2$, Pd/ZnO, Pd/CdO, $Pd/TiO_2$, $Pd/SnO_2$, Pd/PbO, $Pd/As_2O_3$, $Pd/Bi_2O_3$, $Pd/Sb_2O_5$, $Pd/V_2O_5$, $Pd/Nb_2O_5$, $Pd/Cr_2O_3$, $Pd/MoO_3$, $Pd/WO_3$, Pd/BeO, Pd/MgO, Pd/CaO, Pd/SrO, Pd/BaO, $Pd/Y_2O_3$, $Pd/La_2O_3$, $Pd/Na_2O$, $Pd/K_2O$, Pd/CdS, Pd/ZnS, $Pd/MgSO_4$, $Pd/CaSO_4$, $Pd/SrSO_4$, $Pd/BaSO_4$, $Pd/CuSO_4$, $Pd/ZnSO_4$, $Pd/CdSO_4$, $Pd/Al_2(SO_4)_3$, $Pd/FeSO_4$, $Pd/Fe_2(SO_4)_3$, $Pd/CoSO_4$, $Pd/NiSO_4$, $Pd/Cr_2(SO_4)_3$, $Pd/KHSO_4$, $Pd/K_2SO_4$, $Pd/(NH_4)_2SO_4$, $Pd/Zn(NO_3)_2$, $Pd/Ca(NO_3)_2$, $Pd/Bi(NO_3)_3$, $Pd/Fe(NO_3)_3$, $Pd/Na_2CO_3$, $Pd/K_2CO_3$, $Pd/KHCO_3$, $Pd/KNaCO_3$, $Pd/CaCO_3$, $Pd/SrCO_3$, $Pd/BaCO_3$, $Pd/(NH_4)_2CO_3$, $Pd/Na_2WO_4 \cdot 2H_2O$, Pd/KCN, $Pd/BPO_4$, $Pd/AlPO_4$, $Pd/CrPO_4$, $Pd/FePO_4$, $Pd/Cu_3(PO_4)_2$, $Pd/Zn_3(PO_4)_2$, $Pd/Mg_3(PO_4)_2$, $Pd/Ti_3(PO_4)_4$, $Pd/Zr_3(PO_4)_4$, $Pd/Ni_3(PO_4)_2$, Pd/AgCl, Pd/CuCl, $Pd/CaCl_2$, $Pd/AlCl_3$, $Pd/TiCl_3$, $Pd/SnCl_2$, $Pd/CaF_2$, $Pd/BaF_2$, $Pd/AgClO_4$, $Pd/Mg(ClO_4)_2$, Pd/Zeolite, $Pd/SiO_2$—$Al_2O_3$, $Pd/SiO_2$—$TiO_3$, $Pd/SiO_2$—$ZrO_2$, $Pd/SiO_2$—BeO, $Pd/SiO_2$—MgO, $Pd/SiO_2$—CaO, $Pd/SiO_2$—SrO, $Pd/SiO_2$—BaO, $Pd/SiO_2$—ZnO, $Pd/SiO_2$—$TiO_2$, $Pd/SiO_2$—$ZrO_2$, $Pd/SiO_2$—$Ga_2O_3$, $Pd/SiO_2$—$Y_2O_3$, $Pd/SiO_2$—$La_2O_3$, $Pd/SiO_2$—$MoO_3$, $Pd/SiO_2$—$WO_3$, $Pd/SiO_2$—$V_2O_5$, $Pd/SiO_2$—$ThO_2$, $Pd/Al_2O_3$—MgO, $Pd/Al_2O_3$—ZnO, $Pd/Al_2O_3$—CdO, $Pd/Al_2O_3$—$B_2O_3$, $Pd/Al_2O_3$—$ThO_2$, $Pd/Al_2O_3$—$TiO_2$, $Pd/Al_2O_3$—$ZrO_2$, $Pd/Al_2O_3$—$V_2O_5$, $Pd/Al_2O_3$—$MoO_3$, $Pd/Al_2O_3$—$WO_3$, $Pd/Al_2O_3$—$Cr_2O_3$, $Pd/Al_2O_3$—$Mn_2O_3$, $Pd/Al_2O_3$—$Fe_2O_3$, $Pd/Al_2O_3$—$Co_3O_4$, $Pd/Al_2O_3$—NiO, $Pd/TiO_2$—CuO, $Pd/TiO_2$—MgO, $Pd/TiO_2$—ZnO, $Pd/TiO_2$—CdO, $Pd/TiO_2$—$ZrO_2$, $Pd/TiO_2$—$SnO_2$, $Pd/TiO_2$—$Bi_2O_3$, $Pd/TiO_2$—$Sb_2O_5$, $Pd/TiO_2$—$V_2O_5$, $Pd/TiO_2$—$Cr_2O_3$, $Pd/TiO_2$—$MoO_3$, $Pd/TiO_2$—$WO_3$, $Pd/TiO_2$—$Mn_2O_3$, $Pd/TiO_2$—$Fe_2O_3$, $Pd/TiO_2$—$Co_3O_4$, $Pd/TiO_2$—NiO, $Pd/ZrO_2$—CdO, Pd/ZnO—MgO, Pd/ZnO—$Fe_2O_3$, $Pd/MoO_3$—CoO—$Al_2O_3$, $Pd/MoO_3$—NiO—$Al_2O_3$, $Pd/TiO_2$—$SiO_2$—MgO, $Pd/MoO_3$—$Al_2O_3$—MgO, Pd/(Heteropoly acids), $Pt/SiO_2$, $Pt/Al_2O_3$, Pt/Zeolite, $Rh/Al_2O_3$ and the like.

(Optically Active Cyclic Nitrogen-Containing Compound)

Next, optically active cyclic nitrogen-containing compounds represented by the formula (1) and the formula (2) will be described.

The optically active cyclic nitrogen-containing compounds are, for example, optically active cyclic nitrogen-containing compounds represented by the formula (1).

[Chem. 22]

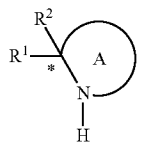

(1)

In the formula (1), ring A is a 3- to 7-membered ring which may have a substituent group and contains at least one atom selected from the group consisting of carbon, nitrogen, sulfur, oxygen, and phosphorus, and preferably consists of the atom(s). The ring A may be a fused ring structure.

$R^1$ and $R^2$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amide group which may have a substituent group, a siloxy group which may have a substituent group, an aromatic heterocyclic group which may have a substituent group, or an aliphatic heterocyclic group which may have a substituent group, with the proviso that $R^1$ and $R^2$ do not represent a same substituent group; either $R^1$ or $R^2$ may be bonded to the ring A to form a ring; and * represents an asymmetric carbon atom]

As basic skeleton of the ring A, for example, aziridine skeleton, azetidine skeleton, pyrrolidine skeleton, pyrroline skeleton, pyrazolidine skeleton, imidazolidine skeleton, imidazolidinone skeleton, pyrazoline skeleton, thiazolidine skeleton, piperidine skeleton, piperazine skeleton, morpholine skeleton, thiomorpholine skeleton and the like can be mentioned. A substituent group may be present in these basic skeletons.

Examples of the basic skeleton of the ring A when it has a ring-fused structure by a benzene ring or the like include indoline skeleton, dihydroquinoxaline skeleton, tetrahydroisoquinoline skeleton, and dihydroquinoxalinone skeleton. These basic skeletons may have a substituent group therein.

Examples of the substituent group include a hydroxyl group, an oxo group, halogen groups, alkyl groups, alkoxy groups, an amino group, alkoxycarbonyl groups, acyl groups, aryl groups, aralkyl groups, aromatic heterocyclic groups, and aliphatic heterocyclic groups. Examples of the alkyl group, alkoxy group, alkoxycarbonyl group, aryl group, aralkyl group, aromatic heterocyclic group, and aliphatic heterocyclic group include those exemplified in the description of $R^1$ and $R^2$. Examples of the halogen atom include fluorine atom, chlorine atom, bromine atom, and iodine atom. Examples of the acyl group include acetyl group, propanoyl group, butanoyl group, octanoyl group, benzoyl group, toluoyl group, xyloyl group, naphthoyl group, phenanthroyl group, and anthranoyl group.

The ring A and the ring-fused ring A are, among those described above, preferably pyrrolidine skeleton which may have a substituent group, imidazolidinone skeleton which may have a substituent group, and dihydroquinoxaline skeleton which may have a substituent group.

Preferred example of the substituent group of the ring A and the ring-fused ring A include an alkyl group which may have a substituent group, an aralkyl group which may have a substituent group, and an aromatic heterocyclic group which may have a substituent group.

Next, as the groups represented by $R^1$ and $R^2$, the alkyl group, cycloalkyl group, alkenyl group, aryl group, aralkyl group, alkoxy group, carboxyl group, alkoxycarbonyl group, amide group, siloxy group, aromatic heterocyclic group, and aliphatic heterocyclic group will be described. These groups may each have a substituent group.

As the alkyl group, examples thereof include a straight chain or branched chain alkyl group having, for example, from 1 to 30 carbon atoms, preferably from 1 to 10 carbon atoms, and illustrative examples thereof include methyl group, ethyl group, n-propyl group, isopropyl group, n-butyl group, 2-butyl group, isobutyl group, tert-butyl group, n-pentyl group, 2-pentyl group, 3-pentyl group, tert-pentyl group, 2-methylbutyl group, 3-methylbutyl group, 2,2-dimethylpropyl group, 1,2-dimethylpropyl group, n-hexyl group, 2-hexyl group, 3-hexyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, henicosyl group, docosyl group and the like.

These alkyl groups may have a substituent group and examples of the substituent group of the alkyl group include alkenyl groups, alkynyl groups, aryl groups, aliphatic heterocyclic groups, aromatic heterocyclic groups, alkoxy groups, trialkylsiloxy groups, alkylenedioxy groups, aryloxy groups, aralkyloxy groups, heteroaryloxy groups, substituted amino group, alkyl halide groups, cycloalkyl groups, hydroxyl group, and halogen atoms.

As the alkenyl group as a substituent group of alkyl group, examples thereof include a straight chain or branched chain alkenyl group having, for example, from 2 to 20 carbon atoms, preferably from 2 to 10 carbon atoms, more preferably from 2 to 6 carbon atoms, and illustrative examples thereof include vinyl group, propenyl group, 1-butenyl group, pentenyl group, hexenyl group and the like.

As the alkynyl group as a substituent group of alkyl group, examples thereof include a straight chain or branched chain alkynyl group having, for example, from 2 to 15 carbon atoms, preferably from 2 to 10 carbon atoms, more preferably from 2 to 6 carbon atoms, and illustrative examples thereof include ethynyl group, 1-propynyl group, 2-propynyl group, 1-butynyl group, 3-butynyl group, pentinyl group, hexynyl group and the like.

Examples of the aryl group as the substituent group of the alkyl group include aryl groups having from 6 to 20 carbon atoms, more specifically, a phenyl group, a tolyl group, an isopropylphenyl group, a xylyl group, a t-butylphenyl group, a cyclohexyl group, a 1-methylcyclohexyl group, an adamantylphenyl group, a trifluoromethylphenyl group, a naphthyl group, an anthranyl group, a phenanthryl group, a biphenyl group, a 4-(2'-p-tolylpropyl)phenyl group, a mesityl group, a methoxyphenyl group, a dimethoxyphenyl group, a 4-(3',4',5',6',7',8',9',10'-heptadecafluorodecyl)phenyl group, and a fluorophenyl group.

As the aliphatic heterocyclic group as a substituent group of alkyl group, examples thereof include a group which has, for example, from 2 to 14 carbon atoms and contains, as heterogeneous atoms, at least one, preferably from 1 to 3 hetero atoms such as nitrogen atom, oxygen atom and sulfur atom. Preferably, a 5- or 6-membered monocyclic aliphatic heterocyclic group and a polycyclic or condensed ring aliphatic heterocyclic group can be mentioned. Illustrative examples of the aliphatic heterocyclic group include 2-oxo-1-pyrrolidinyl group, piperidino group, piperazinyl group, morpholino group, tetrahydrofuryl group, tetrahydropyranyl group, tetrahydrothienyl group and the like.

As the aromatic heterocyclic group as a substituent group of alkyl group, examples thereof include a group which has, for example, from 2 to 15 carbon atoms and contains, as heterogeneous atoms, at least one, preferably from 1 to 3 hetero atoms such as nitrogen atom, oxygen atom and sulfur atom. Preferably, a 5- or 6-membered monocyclic aromatic heterocyclic group and a polycyclic or condensed ring aromatic heterocyclic group can be mentioned. Illustrative examples of the aromatic heterocyclic group include furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

As the alkoxy group as a substituent group of alkyl group, examples thereof include a straight chain or branched chain alkoxy group having, for example, from 1 to 8 carbon atoms, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group and the like.

As the trialkylsiloxy group as a substituent group of alkyl group, examples thereof include trimethylsiloxy group, triethylsiloxy group, dimethyl-tert-butylsiloxy group and the like.

As the alkylenedioxy group as a substituent group of alkyl group, examples thereof include an alkylenedioxy group having, for example, from 1 to 3 carbon atoms, and illustrative examples thereof include methylenedioxy group, ethylenedioxy group, propylenedioxy group, isopropylidenedioxy group and the like.

As the aryloxy group as a substituent group of alkyl group, examples thereof include an aryloxy group having, for example, from 6 to 15 carbon atoms can be mentioned, and illustratively, phenoxy group, naphthyloxy group, anthryloxy group, tolyloxy group, xylyloxy group, 4-phenylphenoxy group, 3,5-diphenylphenoxy group, 4-mesitylphenoxy group, 3,5-bis(trifluoromethyl)phenoxy group and the like.

As the aralkyloxy group as a substituent group of alkyl group, examples thereof include an aralkyloxy group having from 7 to 12 carbon atom, and illustrative examples thereof include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

As the heteroaryloxy group as a substituent group of alkyl group, examples thereof include a heteroaryloxy group which has, for example, from 2 to 14 carbon atoms and contains, as heterogeneous atoms, at least one, preferably from 1 to 3 hetero atoms such as nitrogen atom, oxygen atom and sulfur atom, and illustrative examples thereof include 2-pyridyloxy group, 2-pyrazyloxy group, 2-pyrimidyloxy group, 2-quinolyloxy group and the like.

As the substituted amino group as a substituent group of alkyl group, examples thereof include mono- or di-alkylamino groups such as N-methylamino group, N,N-dimethylamino group, N,N-diethylamino group, N,N-diisopropylamino group, N-cyclohexylamino group, pyrrolidyl group, piperidyl group and morpholyl group; mono- or di-arylamino group such as N-phenylamino group, N,N-diphenylamino group, N-naphthylamino group and N-naphthyl-N-phenylamino group; mono- or di-aralkylamino group such as N-benzylamino group and N,N-dibenzylamino group; and the like.

The alkyl halide group as a substituent group of the alkyl group is preferably a perhalogenoalkyl group. Examples thereof include a trifluoromethyl group, a pentafluoroethyl group, a heptafluoropropyl group, an undecafluoropentyl group, a heptadecafluorooctyl group, an undecafluorohexyl group, and a dichloromethyl group.

Examples of the cycloalkyl group as a substituent group of the alkyl group include a cyclopropyl group, a cyclobutyl group, a cyclopentyl group, and a cyclohexyl group.

As the halogen atom substituting the alkyl group, examples thereof include fluorine atom, chlorine atom, bromine atom, iodine atom and the like.

As the cycloalkyl group, examples thereof include cyclopropyl group, cyclobutyl group, cyclopentyl group, cyclohexyl group and the like.

These cycloalkyl groups may have a substituent group, and as said substituent group, the substituent groups described in the aforementioned description on the substituent group of alkyl group can be mentioned.

As the alkenyl group, examples thereof include a straight or branched chain or cyclic alkenyl group having, for example, from 2 to 20 carbon atoms, preferably from 2 to 10 carbon atoms. Illustrative examples of alkenyl groups include vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 4-methyl-3-pentenyl group, 4,8-dimethyl-3,7-nonadienyl group, 1-cyclohexenyl group, 3-cyclohexenyl group and the like.

These alkenyl groups may have a substituent group, and as said substituent group, the groups described in the aforementioned description on the substituent group of alkyl group can be mentioned.

As the aryl group, examples thereof include aryl groups having from 6 to 20 carbon atoms. Specific examples thereof include a phenyl group, a tolyl group, an isopropylphenyl group, a xylyl group, a t-butylphenyl group, a cyclohexyl group, a 1-methylcyclohexyl group, an adamantylphenyl group, a trifluoromethylphenyl group, a naphthyl group, an anthranyl group, a phenanthryl group, a biphenyl group, a 4-(2'-p-tolylpropyl)phenyl group, a mesityl group, a methoxyphenyl group, a dimethoxyphenyl group, a 4-(3',4',5',6',7',8',9',10'-heptadecafluorodecyl)phenyl group, and a fluorophenyl group.

These aryl groups may have a substituent group and examples of the substituent group include the groups described in the above-mentioned description on the substituent group of the alkyl group.

As the aralkyl group, an aralkyl group having, for example, from 7 to 45 carbon atoms is desirable, and illustrative examples thereof include benzyl group, tolylmethyl group, xylylmethyl group, mesitylmethyl group, 4-phenylphenylmethyl group, 3-phenylphenylmethyl group, 2-phenylphenylmethyl group, 4-mesitylphenylmethyl group, 1-naphthylmethyl group, 2-naphthylmethyl group, 9-anthranylmethyl group, 9-phenanthrylmethyl group, 3,5-diphenylphenylmethyl group, 2-phenylethyl group, 1-phenylpropyl group, 3-naphthylpropyl group, diphenylmethyl group, ditolylmethyl group, dixylylmethyl group, dimesitylmethyl group, di(4-phenylphenyl)methyl group, di(3-phenylphenyl)methyl group, di(2-phenylphenyl)methyl group, di(4-mesitylphenyl)methyl group, di(1-naphthyl)lmethyl group, di(2-naphthyl)methyl group, di(9-anthranyl)methyl group, di(9-phenanthryl)methyl group, bis(3,5-diphenylphenyl)methyl group, triphenylmethyl group, tritolylmethyl group, trixylylmethyl group, trimesitylmethyl group, tri(4-phenylphenyl) methyl group, tri(3-phenylphenyl)methyl group, tri(2-phenylphenyl)methyl group, tri(4-mesitylphenyl)methyl group, tri(1-naphthyl)methyl group, tri(2-naphthy)lmethyl group, tri (9-anthranyl)methyl group, tri(9-phenanthryl)methyl group, tris(3,5-diphenylphenyl)methyl group, trimethylsiloxyphenylmethyl group, trimethylsiloxydiphenyl methyl group, trimethylsiloxyditolyl methyl group, trimethyl siloxydi(4-t-butylphenyl)methyl group, trimethylsiloxydixylylmethyl group, trimethylsiloxydi(2-phenylphenyl)methyl group, trimethylsiloxydi(3-phenylphenyl)methyl group, trimethylsiloxydi(4-phenylphenyl)methyl group, trimethylsiloxybis(3, 5-diphenylphenyl)methyl group, trimethylsiloxydi(4-mesitylphenyl)methyl group, trimethylsiloxybis(3,5-ditrifluoromethylphenyl)methyl group and the like.

These aralkyl groups may have a substituent group, and as said substituent group, the groups described in the description on the substituent group of alkyl group can be mentioned.

As the alkoxy group, an alkoxy group having, for example, from 1 to 30 carbon atoms is desirable, and illustrative examples thereof include methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group, dicyclopentylmethoxy group, dicyclohexylmethoxy group, tricyclopentyl methoxy group, tricyclohexylmethoxy group, phenylmethoxy group, diphenylmethoxy group, triphenylmethoxy group and the like.

These alkoxy groups may have a substituent group, and as said substituent group, the groups described in the description on the substituent group of alkyl group can be mentioned.

As the carboxyl group, a carboxyl group having, for example, from 1 to 30 carbon atoms is desirable, and illustrative examples thereof include acetoxy group, n-propanoyloxy group, isopropanoyloxy group, n-butanoyloxy group, 2-butanoyloxy group, isobutanoyloxy group, tert-butanoyloxy group, n-pentanoyloxy group, 2-methylbutanoyloxy group, 3-methylbutanoyloxy group, 2,2-dimethylpropanoyloxy group, n-hexanoyloxy group, 2-methylpentanoyloxy group, 3-methylpentanoyloxy group, 4-methylpentanoyloxy group, 5-methylpentanoyloxy group, cyclopentanoyloxy group, cyclohexanoyloxy group, dicyclopentylacetoxy group, dicyclohexylacetoxy group, tricyclopentylacetoxy group, tricyclohexylacetoxy group, phenylacetoxy group, diphenylacetoxy group, triphenylacetoxy group, benzoyloxy group, naphthoyloxy group and the like.

These carboxyl groups may have a substituent group, and as said substituent group, the groups described in the description on the substituent group of alkyl group can be mentioned.

As the alkoxycarbonyl group, an alkoxycarbonyl group having, for example, from 1 to 30 carbon atoms is desirable, and illustrative examples thereof include methoxycarbonyl group, ethoxycarbonyl group, n-propoxycarbonyl group, isopropoxycarbonyl group, n-butoxycarbonyl group, 2-butoxycarbonyl group, isobutoxycarbonyl group, tert-butoxycarbonyl group, n-pentyloxycarbonyl group, 2-methylbutoxycarbonyl group, 3-methylbutoxycarbonyl group, 2,2-dimethylpropoxycarbonyl group, n-hexyloxycarbonyl group, 2-methylpentyloxycarbonyl group, 3-methylpentyloxycarbonyl group, 4-methylpentyloxycarbonyl group, 5-methylpentyloxycarbonyl group, cyclopentyloxycarbonyl group, cyclohexyloxycarbonyl group, dicyclopentylmethoxycarbonyl group, dicyclohexylmethoxycarbonyl group, tricyclopentylmethoxycarbonyl group, tricyclohexylmethoxycarbonyl group, phenylmethoxycarbonyl group, diphenylmethoxycarbonyl group, triphenylmethoxycarbonyl group and the like.

These alkoxycarbonyl groups may have a substituent group, and as said substituent group, the groups described in the description on the substituent group of alkyl group can be mentioned.

As the amide group, an amide group having, for example, from 1 to 30 carbon atoms is desirable, and illustrative examples thereof include acetamide group, n-propionamide group, isopropionamide group, n-butanamide group, 2-butanamide group, isobutanamide group, tert-butanamide group, n-pentanamide group, 2-methylbutanamide group, 3-methylbutanamide group, 2,2-dimethyl propionamide group, n-hexanamide group, 2-methylpentanamide group, 3-methylpentanamide group, 4-methylpentanamide group, 5-methylpentanamide group, cyclopentanamide group, cyclohexanamide group, dicyclopentylacetamide group, dicyclohexylacetamide group, tricyclopentylacetamide group, tricyclohexylacetamide group, phenylacetamide group, diphenylacetamide group, triphenylacetamide group, benzamide group, naphthalenamide group and the like.

These amide groups may have a substituent group, and as said substituent group, the groups described in the description on the substituent group of alkyl group can be mentioned.

As the siloxy group, examples thereof include trimethylsiloxy group, triethylsiloxy group, dimethyl-tert-butylsiloxy group and the like.

These siloxy groups may have a substituent group, and as said substituent group, the groups described in the description on the substituent group of alkyl group can be mentioned.

As the aromatic heterocyclic group, examples thereof include groups having from 2 to 15 carbon atoms and having, as a hetero atom, at least one, preferably from 1 to 3 heteroatoms such as nitrogen atom, oxygen atom or sulfur atom. Preferred examples thereof include a 5- or 6-membered monocyclic aromatic heterocyclic group and a polycyclic or ring-fused aromatic heterocyclic group. Specific examples of the aromatic heterocyclic group include a furyl group, a methylfuryl group, a thienyl group, a pyridyl group, a pyrimidinyl group, a pyrazinyl group, a pyridazinyl group, a pyrazolinyl group, an imidazolyl group, an oxazolinyl group, a thiazolinyl group, a benzofuryl group, a benzothienyl group, a quinolyl group, an isoquinolyl group, a quinoxalinyl group, a phthalazinyl group, a quinazolinyl group, a naphthyridinyl group, cinnolinyl group, benzimidazolyl group, a benzoxazolyl group, and a benzothiazolyl group.

These aromatic heterocyclic groups may have a substituent group and examples of the substituent group include the groups as described above in the description on the alkyl group.

As the aliphatic heterocyclic group, examples thereof include groups having from 2 to 14 carbon atoms and having at least one, preferably from 1 to 3 hetero atoms such as a nitrogen atom, an oxygen atom, or a sulfur atom. Preferred examples thereof include 5- or 6-membered monocyclic aliphatic heterocyclic groups and polycyclic or ring-fused aliphatic heterocyclic groups. Specific examples of the aliphatic heterocyclic group include a 2-oxy-1-pyrrolidinyl group, a piperidino group, a piperazinyl group, a morpholino group, a tetrahydrofuryl group, a tetrahydropyranyl group, and a tetrahydrothienyl group. These aliphatic heterocyclic groups may have a substituent group and examples of the substituent group include the groups described above in the description on the alkyl group.

Preferred examples of the group represented by $R^1$ and $R^2$ include hydrogen, alkyl groups which may have a substituent group, and aralkyl groups which may have a substituent group.

It is to be noted that an amino acid does not correspond to the optically active cyclic nitrogen-containing compound of the present invention.

Moreover, examples of the optically active cyclic nitrogen-containing compound include optically active cyclic nitrogen-containing compounds represented by the formula (2).

[Chem. 23]

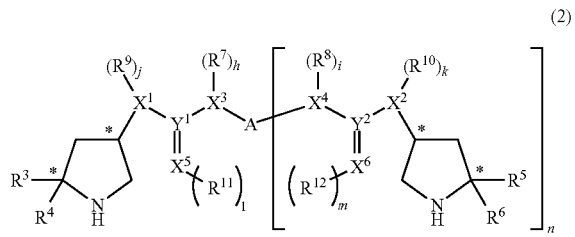

(2)

In the formula (2), $R^3$, $R^4$, $R^5$, $R^6$, $R^7$, $R^8$, $R^9$, $R^{10}$, $R^{11}$, and $R^{12}$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amide group which may have a substituent group, a siloxy group which may have a substituent group, an aromatic heterocyclic group which may have a substituent group, or an aliphatic heterocyclic group which may have a substituent group, with the proviso that $R^3$ and $R^4$ represent substituent groups different from each other and $R^5$ and $R^6$ represent substituent groups different from each other;

h, i, j, k, l, and m each represent an integer of 0 or 1, n represents an integer of from 0 to 3; and * represents an asymmetric carbon atom;

A represents, when n is 0, a hydrogen atom, a hetero atom which may have a substituent group, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amide group which may have a substituent group, an aromatic heterocyclic group which may have a substituent group, an aliphatic heterocyclic group which may have a substituent group, an oligomer chain or a polymer chain; and A represents, when n is 1 to 3, a hetero atom which may have a substituent group, an alkylene group which may have a substituent group, an arylene group-containing alkylene group which may have a substituent group, a cycloalkylene group-containing alkylene group which may have a substituent group, a hetero atom-containing alkylene group which may have a substituent group, a divalent aliphatic hydrocarbon ring group which may have a substituent group, a divalent aliphatic heterocyclic group which may have a substituent group, a divalent aromatic hydrocarbon ring group which may have a substituent group, a divalent aromatic heterocyclic group which may have a substituent group, an oligomer chain or a polymer chain;

$R^7$ and $R^8$, $R^7$ and A, or $R^8$ and A may be bonded to each other to form a ring;

$X^1$, $X^2$, $X^3$, $X^4$, $X^5$, and $X^6$ each independently represent an oxygen atom, a nitrogen atom, a phosphorus atom or a sulfur atom; and $Y^1$ and $Y^2$ each independently represent a carbon atom, a silicon atom or a sulfur atom.

Examples of the alkyl group, cycloalkyl group, alkenyl group, aryl group, aralkyl group, alkoxy group, carboxyl group, alkoxycarbonyl group, amide group, siloxy group, aromatic heterocyclic group, and aliphatic heterocyclic group represented by $R^3$, $R^4$, $R^5$, $R^6$, $R^7$, $R^8$, $R^9$, $R^{10}$, $R^{11}$ and $R^{12}$ include the groups exemplified in the description of $R^1$ and $R^2$ on the optically active cyclic nitrogen-containing compound represented by the formula (1). These groups may each have a substituent group and specific examples of the substituent group include the substituent groups exemplified in the description on the substituent group of the alkyl group represented by $R^1$ or $R^2$.

Of these groups, $R^3$ to $R^6$ each preferably represent a hydrogen atom or an aryl group which may have a substituent group, with a hydrogen atom and a phenyl group which may have a substituent group being particularly preferred.

Of these groups, $R^7$ to $R^{12}$ each preferably represent a hydrogen atom, an alkyl group which may have a substituent group, a cycloalkyl group which may have a substituent group, or an aryl group which may have a substituent group, with a hydrogen atom, a phenyl group which may have a substituent group, or a cyclohexyl group which may have a substituent group being particularly preferred.

Next, the following describes about A.

When n is 0, A represents a hydrogen atom, a hetero atom which may have a substituent group, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amide group which may have a substituent group, an aromatic heterocyclic group which may have a substituent group, an aliphatic heterocyclic group which may have a substituent group, an oligomer chain or a polymer chain.

Examples of the hetero atom include an oxygen atom, a nitrogen atom, and a silicon atom.

These hetero atoms may have a substituent group and examples of the substituent group include a hydrogen atom, alkyl groups, alkenyl groups, alkynyl groups, aryl groups, aliphatic heterocyclic groups, and aromatic heterocyclic groups. Specific examples thereof include the groups exemplified in the description of $R^1$ and $R^2$ and the groups exemplified as the substituent group of the alkyl group in the description of $R^1$ and $R^2$.

Examples of the alkyl group which may have a substituent group, cycloalkyl group which may have a substituent group, alkenyl group which may have a substituent group, aryl group which may have a substituent group, aralkyl group which may have a substituent group, alkoxy group which may have a substituent group, carboxyl group which may have a substituent group, alkoxycarbonyl group which may have a substituent group, amide group which may have a substituent group, aromatic heterocyclic group which may have a substituent group, and aliphatic heterocyclic group which may have a substituent group include those in the description of $R^1$ and $R^2$.

The oligomer chain is usable insofar as it is generally used. Examples thereof include an oligomer chain such as polystyrene, polyethylene glycol, polyacrylate, polymethacrylate, polyester, polyamide, polyethylene, polypropylene, polycarbonate, polyurethane, and polypeptide, and copolymers thereof.

The polymer chain is usable insofar as it is generally used. Examples thereof include polystyrene, polyethylene glycol, polyacrylate, polymethacrylate, polyester, polyamide, polyethylene, polypropylene, polycarbonate, polyurethane, and polypeptide, and copolymers thereof.

Of these, a hydrogen atom, alkyl groups which may have a substituent group, cycloalkyl groups which may have a substituent group, and aryl groups which may have a substituent group are preferred, with a hydrogen atom and alkyl groups which may have a substituent group being particularly preferred.

Next, a description will be made on the hetero atom, alkylene group, arylene group-containing alkylene group, cycloalkylene group-containing alkylene group, hetero atom-containing alkylene group, divalent aliphatic hydrocarbon cyclic group, divalent aliphatic heterocyclic group, divalent aromatic hydrocarbon cyclic group, divalent aromatic heterocyclic group, oligomer chain, and polymer chain as the A when n is 1 to 3. These groups may have a substituent group.

Examples of the hetero atom include an oxygen atom, a nitrogen atom, and a silicon atom.

These hetero atoms may have a substituent group and examples of the substituent group include a hydrogen atom, alkyl groups, alkenyl groups, alkynyl groups, aryl groups, aliphatic heterocyclic groups, and aromatic heterocyclic groups. Specific examples include groups exemplified above in the description of $R^1$ and $R^2$ and groups exemplified above as a substituent group of the alkyl group in the description of $R^1$ and $R^2$.

Examples of the alkylene group include groups obtained by removing one hydrogen atom from linear or branched alkyl groups having from 1 to 30 carbon atoms, preferably from 1 to 10 carbon atoms. Specific examples thereof include groups obtained by removing one hydrogen atom from the alkyl groups described above in the description of $R^1$ and $R^2$.

These alkylene groups may have a substituent group and examples of the substituent group include the substituent groups of the alkyl group in the description of $R^1$ and $R^2$.

Examples of the arylene-containing alkylene group include a group in which an arylene group is included in the above-mentioned alkylene groups. As the arylene group as used herein, examples thereof include a divalent aromatic hydrocarbon cyclic group which will be described later. The arylene group may have a substituent group and examples of the substituent group include the substituent groups of the alkyl group in the description of $R^1$ and $R^2$.

These arylene group-containing alkylene groups may have a substituent group and examples of the substituent group include the substituent groups of the alkyl group in the description of $R^1$ and $R^2$.

Examples of the cycloalkylene group-containing alkylene group include a group in which a cycloalkylene group is included in the above-described alkylene group. As the cycloalkylene group as used herein, examples thereof include a divalent aliphatic hydrocarbon cyclic group which will be described later. The cycloalkylene group may have a substituent group and examples of the substituent group include the substituent groups of the alkyl group in the description of $R^1$ and $R^2$.

The cycloalkylene group-containing alkylene groups may have a substituent group and example of the substituent group include the substituent groups of the alkyl group in the description of $R^3$ to $R^{12}$.

Examples of the hetero atom-containing alkylene group include a group in which a hetero atom is included in the above-mentioned alkylene group. As the hetero atom as used herein, examples thereof include an oxygen atom, a nitrogen atom, and a silicon atom.

These hetero atom-containing alkylene groups may have a substituent group and examples of the substituent group include the substituent groups of the alkyl group in the description of $R^1$ and $R^2$.

Examples of the divalent aliphatic hydrocarbon cyclic group include divalent groups derived from the cycloalkyl groups in the description of $R^1$ and $R^2$.

These divalent aliphatic hydrocarbon cyclic groups may have a substituent group and examples of the substituent group include the substituent groups of the alkyl group in the description of $R^1$ and $R^2$.

Examples of the divalent aliphatic heterocyclic group include divalent groups derived from the aliphatic heterocyclic groups in the description of $R^1$ and $R^2$.

These divalent aliphatic heterocyclic groups may have a substituent group and examples of the substituent group include the substituent groups of the alkyl group in the description of $R^1$ and $R^2$.

Examples of the divalent aromatic hydrocarbon cyclic group include divalent groups derived from the aryl groups in the description of $R^1$ and $R^2$.

These divalent aromatic hydrocarbon groups may have a substituent group and examples of the substituent group include the substituent groups of the alkyl group in the description of $R^1$ and $R^2$.

Examples of the divalent aromatic heterocyclic group include divalent groups derived from the aromatic heterocyclic groups in the description of $R^1$ and $R^2$.

These divalent aromatic heterocyclic groups may have a substituent group and examples of the substituent group include the substituent groups of the alkyl group in the description of $R^1$ and $R^2$.

The divalent aliphatic hydrocarbon cyclic group, divalent aliphatic heterocyclic group, the divalent aromatic hydrocarbon cyclic group, or the divalent aromatic heterocyclic group may have a polycyclic structure.

The A may have, linked thereto, an alkylene group, arylene group-containing alkylene group, cycloalkylene group-containing alkylene group, hetero atom-containing alkylene group, divalent aliphatic hydrocarbon cyclic group, divalent aliphatic heterocyclic group, divalent aromatic hydrocarbon cyclic group, or divalent aromatic heterocyclic group.

When n is 1 to 3, the A is, of the above-described ones, preferably the alkylene group, arylene group-containing alkylene group, cycloalkylene group-containing alkylene group, divalent aliphatic hydrocarbon cyclic group, or divalent aromatic hydrocarbon cyclic group; particularly preferably the alkylene group, cyclohexylene group-containing alkylene group, phenylene group-containing alkylene group, phenylene group, naphthylene group, polycyclic phenylene group, group to which a phenylene group is linked via an alkylene group, and group to which a cyclohexylene group is linked via an alkylene group.

The oligomer chain is usable insofar as it is generally used. Examples thereof include an oligomer chain such as polystyrene, polyethylene glycol, polyacrylate, polymethacrylate, polyester, polyamide, polyethylene, polypropylene, polycarbonate, polyurethane, and polypeptide, and copolymers thereof.

The polymer chain is usable insofar as it is generally used. Examples thereof include polystyrene, polyethylene glycol, polyacrylate, polymethacrylate, polyester, polyamide, polyethylene, polypropylene, polycarbonate, polyurethane, and polypeptide, and copolymers thereof.

Next, a description will be made on $X^1$, $X^2$, $X^3$, $X^4$, $X^5$, and $X^6$. $X^1$, $X^2$, $X^3$, $X^4$, $X^5$, and $X^6$ each independently represent an oxygen atom, a nitrogen atom, a phosphorus atom, or a sulfur atom.

Next, a description will be made on $Y^1$ and $Y^2$. $Y^1$ and $Y^2$ each independently represent a carbon atom, a silicon atom, or a sulfur atom.

Preferred combinations of $X^1$, $Y^1$, $X^5$, and $X^3$ are, for example, shown in the following Table 1.

TABLE 1

|  | $X^1$ | $Y^1$ | $X^5$ | $X^3$ |
| --- | --- | --- | --- | --- |
| Case 1 | O | C | O | N |
| Case 2 | O | C | O | O |
| Case 3 | O | C | O | S |
| Case 4 | O | C | S | O |
| Case 5 | O | C | S | N |
| Case 6 | O | C | N | N |
| Case 7 | N | C | O | N |
| Case 8 | N | C | O | O |
| Case 9 | N | C | O | S |
| Case 10 | N | C | S | O |
| Case 11 | N | C | S | N |
| Case 12 | N | C | N | N |

Of these, Cases 1, 2, 5, 6, 7, 8, 11, and 12 are more preferred, with Case 1 being still more preferred.

Preferred combinations of $X^2$, $Y^2$, $X^6$, and $X^4$ are, for example, shown in the following Table 2.

TABLE 2

|  | $X^2$ | $Y^2$ | $X^6$ | $X^4$ |
| --- | --- | --- | --- | --- |
| Case 13 | O | C | O | N |
| Case 14 | O | C | O | O |
| Case 15 | O | C | O | S |
| Case 16 | O | C | S | O |
| Case 17 | O | C | S | N |
| Case 18 | O | C | N | N |
| Case 19 | N | C | O | N |
| Case 20 | N | C | O | O |
| Case 21 | N | C | O | S |
| Case 22 | N | C | S | O |
| Case 23 | N | C | S | N |
| Case 24 | N | C | N | N |

Specific examples of the optically active cyclic nitrogen-containing compound include the following compounds.

[Chem. 24]

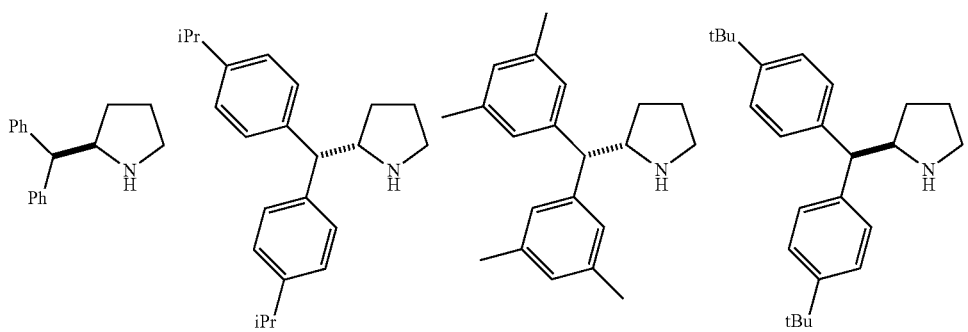

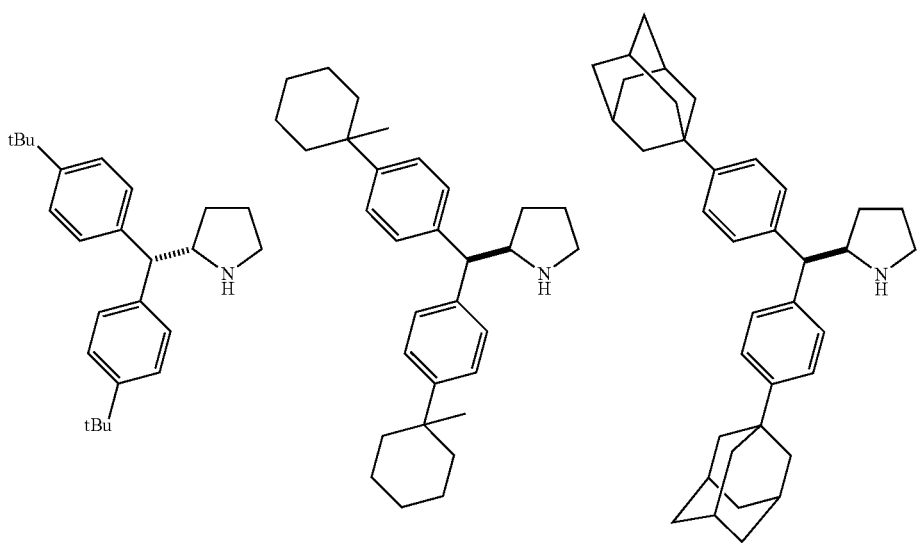

-continued
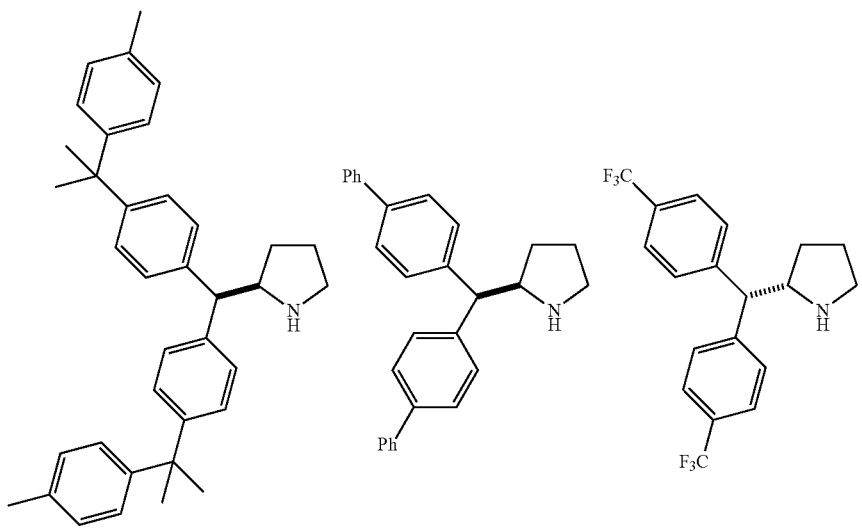
[Chem. 25]
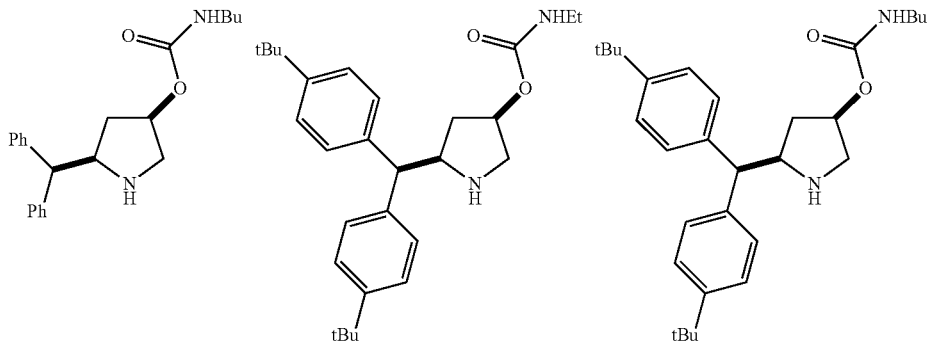
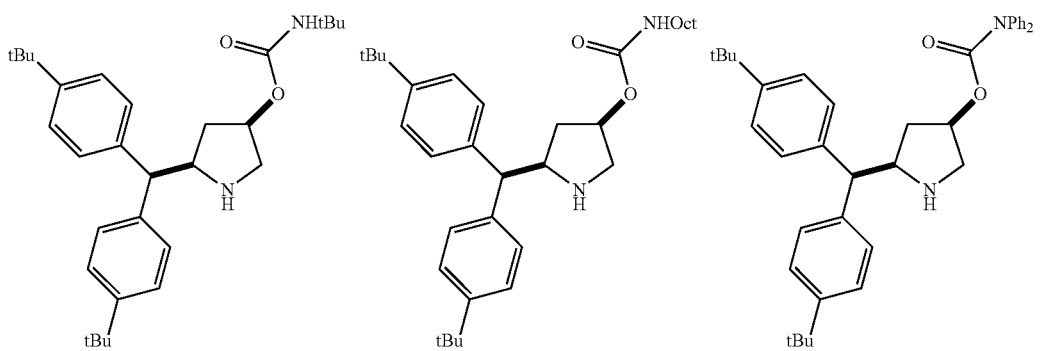
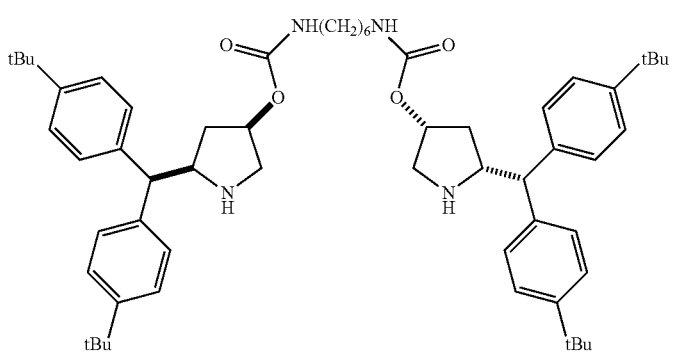

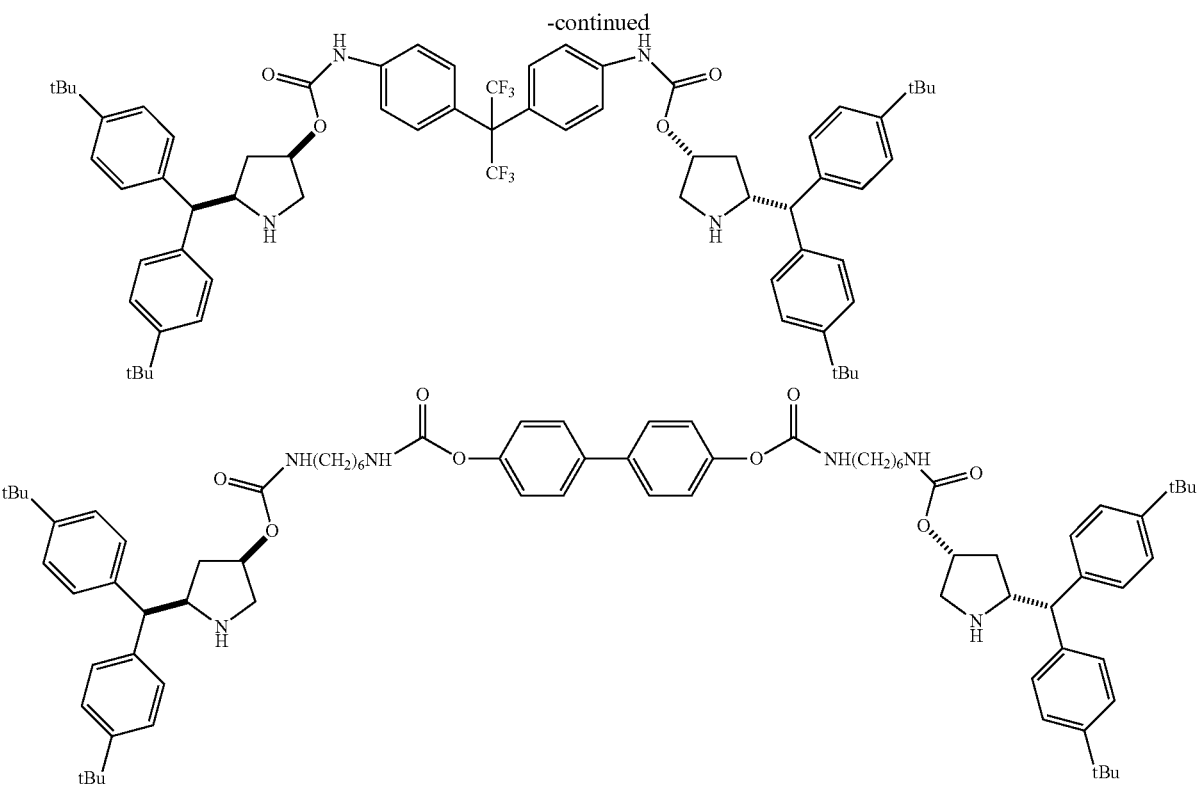

The optically active cyclic nitrogen-containing compound to be used in the present invention may be commercially available or can be synthesized. A method for manufacturing an optically active diarylmethylpyrrolidine compound, among the optically active cyclic nitrogen-containing compounds, will next be described.

The optically active diarylmethylpyrrolidine compound can be synthesized according to the method described, for example, in Tetrahedron 1993, 49, 5127-5132 and Tetrahedron: Asymmetry 1997, 8, 149-153. This method can be represented by the following Schemes 2 and 3.

-continued

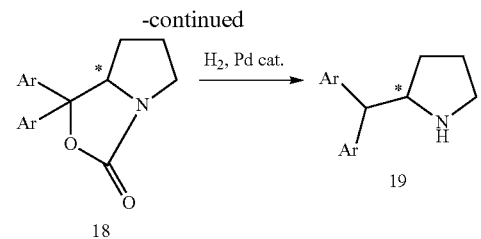

Scheme 2

[Chem. 26]

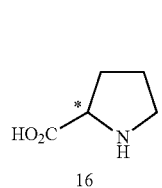

Scheme 3

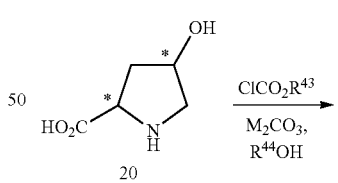

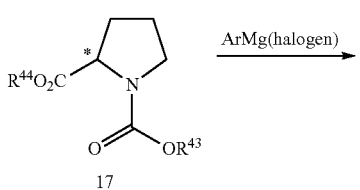

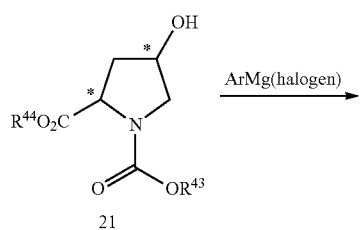

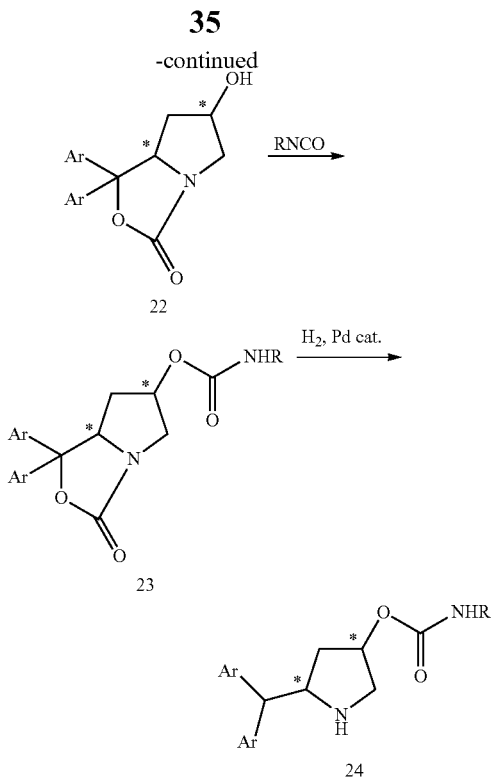

In Schemes 2 and 3, Compound 17 can be synthesized, according to the method described in Tetrahedron 1993, 49, 5127-5132.

Compound 17 can be synthesized by adding dropwise a chlorocarbonate ester compound represented by the formula: $ClCO_2R^{43}$, to a solution, which has been obtained by dissolving (R)- or (S)-proline (Compound 16) and an alkali metal compound represented by the formula: $M_2CO_3$, in an alcohol compound represented by the formula: $R^{44}OH$, in a temperature range of from 0 to 30° C. The used amount (L) of the solvent is, for example, from 1 to 30 times volume [L/kg], preferably from 5 to 20 times volume [L/kg] per weight (kg) of the (R)- or (S)-proline used as a substrate.

Compound 17 thus obtained can be isolated and purified by a generally employed operation such as extraction, recrystallization or various types of chromatography.

Compound 21 can be synthesized by adding dropwise a chlorocarbonate ester compound represented by the formula: $ClCO_2R^{43}$, in a solution, which has been obtained by dissolving (R)- or (S)-hydroxyproline (Compound 20) and an alkali metal compound represented by the formula:$M_2CO_3$, in an alcohol compound represented by the formula: $R^{44}OH$, in a temperature range of from 0 to 30° C. The used amount (L) of the solvent is, for example, from 1 to 30 times volume [L/kg], preferably from 5 to 20 times volume [L/kg] per weight (kg) of the (R)- or (S)-hydroxyproline used as a substrate.

Compound 21 thus obtained can be isolated and purified by a generally employed operation such as extraction, recrystallization or various types of chromatography.

In the chlorocarbonate ester compound represented by the formula: $ClCO_2R^{43}$, examples of the group represented by $R^{43}$ include alkyl groups having from 1 to 8 carbon atoms such as methyl group, ethyl group, propyl group, isopropyl group, butyl group, pentyl group, hexyl group, heptyl group, and octyl group; cyclic alkyl groups having from 1 to 8 carbon atoms such as cyclopropyl group, cyclobutyl group, cyclopentyl group, cycloheptyl group, and cyclooctyl group; and aralkyl groups having from 7 to 10 carbon atoms such as benzyl group and p-methylbenzyl group.

In the alkali metal compound represented by the formula $M_2CO_3$, examples of the metal represented by M include lithium, sodium, potassium, and cesium.

In the alcohol compound represented by the formula $R^{44}OH$, examples of the group represented by $R^{44}$ include alkyl groups exemplified in the description of $R^{43}$.

Compound 18 can be synthesized according to the method described in Tetrahedron: Asymmetry 1997, 8, 149-153.

Compound 18 is synthesized by adding dropwise an ether solution, such as tetrahydrofuran (which will hereinafter be abbreviated as "THF"), of a Grignard compound represented by the formula: ArMg(halogen), to an ether solution, such as THF, of Compound 17 at −5 to 20° C. in an inert gas atmosphere and retaining the reaction temperature, which has been increased to approximately 70° C. in the end, within a range of from 3 to 6 hours. The used amount (L) of the solvent is, for example, from 1 to 40 times volume [L/kg], preferably from 5 to 25 times volume [L/kg] per weight (kg) of Compound 17 used as a substrate.

Compound 18 thus obtained can be isolated and purified by a generally employed operation such as extraction, recrystallization or various types of chromatography.

Compound 22 can be synthesized according to the method described in Tetrahedron: Asymmetry 1997, 8, 149-153.

Compound 22 is synthesized by adding dropwise an ether solution, such as THF, of a Grignard compound represented by the formula: ArMg(halogen), in an ether solution, such as THF, of Compound 21 at −5 to 20° C. in an inert gas atmosphere and retaining the reaction temperature, which has been increased to approximately 70° C. in the end, within a range of from 3 to 6 hours. The used amount (L) of the solvent is, for example, from 1 to 40 times volume [L/kg], preferably from 5 to 25 times volume [L/kg] per weight (kg) of Compound 21 used as a substrate.

Compound 22 thus obtained can be isolated and purified by a generally employed operation such as extraction, recrystallization or various types of chromatography.

Examples of the aryl group represented by Ar in the Grignard compound represented by ArMg(halogen) include aryl groups which have from 6 to 20 carbon atoms and may have a substituent group.

Specific examples of the aryl group include aryl groups exemplified in the description of $R^1$ to $R^{12}$ of the optically active cyclic nitrogen-containing compound represented by the formula (1) or the formula (2).

Specific examples of the substituent group of the aryl group include groups as described in the description of the substituent group of the alkyl group exemplified in the description of $R^1$ to $R^{12}$ of the optically active cyclic nitrogen-containing compound represented by the formula (1) or the formula (2).

Examples of the aryl group include phenyl group, tolyl group, isopropylphenyl group, xylyl group, t-butylphenyl group, cyclohexyl group, 1-methylcyclohexyl group, adamantylphenyl group, trifluoromethylphenyl group, naphthyl group, anthryl group, phenanthryl group, biphenyl group, and 4-(2'-p-tolylpropyl)phenyl group.

In the Grignard compound represented by the formula: ArMg(halogen), examples of the halogen atom represented by "halogen" include chlorine, bromine, and iodine.

Compound 23 can be synthesized easily by a generally employed method such as a method of adding Compound 22 to an isocyanate represented by RNCO.

Compound 23 is synthesized by adding dropwise an isocyanate compound represented by the formula: RNCO, to an aprotic polar solution, such as N,N-dimethylformamide (which will hereinafter be abbreviated as "DMF"), of Compound 22 in the presence of a Lewis acid catalyst such as copper (I) chloride at a temperature near the room temperature in an inert gas atmosphere and stirring the resulting mixture for from 1 to 24 hours. The used amount (L) of the solvent is, for example, from 1 to 20 times volume [L/kg], preferably from 3 to 10 times volume [L/kg] per weight (kg) of Compound 6 used as a substrate.

Compound 23 thus obtained can be isolated and purified by a generally employed operation such as extraction, recrystallization or various types of chromatography.

In the isocyanate compound represented by RNCO, examples of the substituent group represented by R include the substituent groups and polymer chains exemplified in the description of $R^1$ to $R^{12}$ of the optically active cyclic nitrogen-containing compound represented by the formula (1) or the formula (2).

Examples of the substituent group include alkyl groups, cycloalkyl groups, alkenyl groups, aryl groups, aralkyl groups, carboxyl groups, alkoxycarbonyl groups, amide groups, aromatic heterocyclic groups, and aliphatic heterocyclic group. These groups may each have a substituent group.

The optically active diarylmethylpyrrolidine compound represented by Compound 19 can be synthesized according to the method described in Tetrahedron: Asymmetry 1997, 8, 149-153.

Compound 19 is synthesized by debenzylating Compound 18 in the presence of a palladium catalyst in an amount of from 0.1 to 40 wt % based on the amount of Compound 18 in an alcohol solvent represented by $R^{44}OH$ or THF or a mixed solvent thereof at from 20 to 80° C. under a hydrogen atmosphere of from approximately 0.1 MPa to 1 MPa for one day to 10 days. The used amount (L) of the solvent is, for example, from 1 to 50 times volume [L/kg], preferably from 5 to 40 times volume [L/kg] per weight (kg) of Compound 7 used as a substrate.

The optically active diarylmethylpyrrolidine compound represented by Compound 19 thus obtained can be isolated and purified by a generally employed operation such as extraction, recrystallization or various types of chromatography.

Compound 24 is synthesized by debenzylating Compound 23 in the presence of a palladium catalyst in an amount of from 0.1 to 40 wt % based on the amount of Compound 23 in an alcohol solvent represented by $R^{44}OH$ or THF or a mixed solvent thereof at from 20 to 80° C. under a hydrogen atmosphere of from approximately 0.1 MPa to 1 MPa for one day to 10 days. The used amount (L) of the solvent is, for example, from 5 to 50 times volume [L/kg], preferably from 20 to 40 times volume [L/kg] per weight (kg) of Compound 7 used as a substrate.

The optically active diarylmethylpyrrolidine compound represented by Compound 24 thus obtained can be isolated and purified by a generally employed operation such as extraction, recrystallization or various types of chromatography.

The palladium catalyst represented by Pd cat. is selected from debenzylation catalysts such as Pd/C.

In Schemes 2 and 3, * represents an asymmetric carbon atom.

(Acid)

Further, the asymmetric hydrogenation catalyst of citral in the step A of the present invention contains an acid as another catalyst component.

As the acid, either an organic acid or an inorganic acid may be used, but the organic acid is preferred.

Specific examples of the organic acid include acetic acid, chloroacetic acid, difluoroacetic acid, trifluoroacetic acid, trichloroacetic acid, tribromoacetic acid, benzoic acid, 2,4-dinitrobenzoic acid, paratoluenesulfonic acid, methanesulfonic acid, L-lactic acid, DL-tropic acid, DL-malic acid, L-malic acid, D-malic acid, DL-tartaric acid, D-tartaric acid, L-tartaric acid, L-dibenzoyltartaric acid, D-dibenzoyltartaric acid, DL-mandelic acid, L-mandelic acid, D-mandelic acid, and trifluoromethanesulfonic acid.

Specific examples of the inorganic acid include hydrofluoric acid, hydrochloric acid, hydrobromic acid, hydriodic acid, sulfuric acid, perchloric acid, phosphoric acid, and nitric acid.

<Step A: Asymmetric Hydrogenation Reaction>

In the present invention, an optically active citronellal can be obtained by the asymmetric hydrogenation reaction of geranial, neral, or citral in the presence of the above-mentioned catalyst.

Although the amount of the metal powder or metal-supported substance to be used as a component of the asymmetric hydrogenation catalyst of the present invention differs depending on various reaction conditions, the total amount of the metal powder and the total amount of the metal-supported substance are each, for example, from 0.01 to 10 wt %, preferably from 0.02 to 5 wt % based on the amount of the substrate, that is, geranial, neral, or citral.

Although the amount of the optically active cyclic nitrogen-containing compound to be used as a component of the catalyst of the present invention differs depending on various reaction conditions, the amount is, for example, from 0.01 to 20 wt %, preferably from 0.04 to 10 wt % based on the amount of the substrate, that is, geranial, neral, or citral.

Although the amount of the acid to be used as a component of the catalyst of the present invention differs depending on various reaction conditions, it is, for example, from 0.01 to 10 times by mol, preferably from 0.2 to 4 times by mol per the optically active cyclic nitrogen-containing compound.

When preparing an optically active carbonyl compound by the asymmetric hydrogenation of geranial, neral, or citral in the presence of the catalyst of the present invention, the reaction may be conducted either in the presence or absence of a solvent, but it is conducted preferably in the presence of a solvent.

More specifically, the solvent to be used for the preparation is preferably an aliphatic hydrocarbon-based organic solvent such as hexane, heptane or octane; an alicyclic hydrocarbon-based organic solvent such as cyclohexane or methylcyclohexane; an aromatic hydrocarbon-based organic solvent such as benzene, toluene, or xylene; an ether-based organic solvent such as diethyl ether, diisopropyl ether, dimethoxyethane, tetrahydrofuran, dioxane, or dioxolane; water; an alcohol-based organic solvent such as methanol, ethanol, propanol, isopropanol, or tertiary butanol; a halogenated hydrocarbon-based organic solvent such as dichloromethane, dichloroethane, chlorobenzene, or bromotoluene; dimethylformamide, or acetonitrile. Mixtures of these solvents may be used if necessary. Of these solvents, heptane, toluene, tetrahydrofuran, t-butanol, and hydrous t-butanol are particularly preferred.

The used amount (L) of the solvent can be selected as needed depending on the reaction conditions or the like, but it is, for example, from 0 to 20 times volume [(L/kg)], preferably from 0 to 5 times volume [(L/kg)] per weight (kg) of the substrate, that is, geranial, neral, or citral.

In the method of the present invention, a hydrogen gas is used as a hydrogen source and its hydrogen pressure is from 0.01 MPa to 10 MPa, preferably from 0.1 MPa to 1 MPa. The hydrogen gas can also be used in the form of a mixture with an inert gas such as nitrogen, helium, or argon.

The reaction temperature is from −78 to 100° C., preferably from 10 to 70° C. The reaction time is typically from 1 to 30 hours, though depending on the reaction conditions.

The optically active citronellal thus obtained can be isolated and purified by a generally employed operation such as distillation. With regard to the steric configuration of the optically active citronellal thus obtained, either a d-form or an l-form (R-form or S-form) can be prepared by selecting the steric configuration of the optically active cyclic nitrogen-containing compound as needed.

<Step B>

Step B shown in Scheme 1 of the present invention includes ring-closing the optically active citronellal obtained in Step A to thereby prepare an optically active isopulegol.

[Chem. 27]

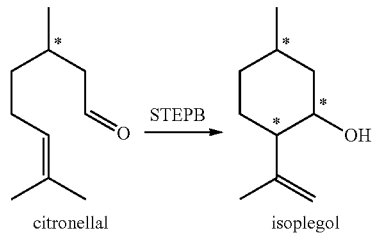

citronellal    isoplegol

<Step B: Ring Closing Catalyst of Optically Active Citronellal>

(Organoaluminum Catalyst)

Step B of Scheme 1: The ring closing catalyst of citronellal is preferably an aluminum catalyst. This aluminum catalyst can be obtained by reacting an organoaluminum compound with a hydroxy compound.

The organoaluminum compound to be used for the preparation of the aluminum catalyst is preferably selected from a trialkylaluminum represented by the formula (3) and at least one organoaluminumoxy compound selected from a branched or unbranched chain aluminoxane represented by the formula (8), a branched or unbranched cyclic aluminoxane represented by the formula (9), and a bis(dialkylaluminumoxy)alkylborane represented by the formula (10).

[Chem. 28]

$$(R^{13})_3Al \quad (3)$$

In the formula (3), $R^{13}$ represents an alkyl group having from 1 to 8 carbon atoms.

Examples of the alkyl group having from 1 to 8 carbon atoms include a methyl group, an ethyl group, an n-propyl group, an isopropyl group, an n-butyl group, an isobutyl group, a sec-butyl group, a tert-butyl group, a pentyl group, a hexyl group, and an octyl group.

[Chem. 29]

 (8)

In the general formula (8), $R^{14}$ represents an alkyl group having from 1 to 6 carbon atoms, an alicyclic group having from 5 to 8 carbon atoms, or an aralkyl group which has from 7 to 12 carbon atoms and may have a substituent group, and a plurality of $R^{14}$ may be the same or different from each other; and o represents an integer of from 0 to 40.

[Chem. 30]

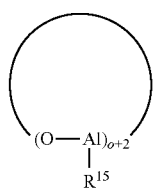

In the general formula (9), $R^{15}$ represents an alkyl group having from 1 to 6 carbon atoms, an alicyclic group having from 5 to 8 carbon atoms, or an aralkyl group which has from 7 to 12 carbon atoms and may have a substituent group; and o represents an integer of from 0 to 40.

[Chem. 31]

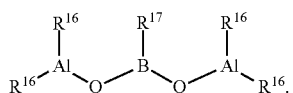 (10)

In the general formula (10), $R^{16}$ represents an alkyl group having from 1 to 6 carbon atoms, an alicyclic group having from 5 to 8 carbon atoms, or an aralkyl group which has from 7 to 12 carbon atoms and may have a substituent group, and a plurality of $R^{16}$ may be the same or different from each other; and $R^{17}$ represents an alkyl group having from 1 to 6 carbon atoms, an alicyclic group having from 5 to 8 carbon atoms, or an aralkyl group which has from 7 to 12 carbon atoms and may have a substituent group.

The following are examples of the predetermined substituent group of the organoaluminumoxy compounds represented by the above formulae (8) to (10).

Examples of the alkyl group having from 1 to 6 carbon atoms include a methyl group, an ethyl group, an n-propyl group, an isopropyl group, an n-butyl group, an isobutyl group, a sec-butyl group, a tert-butyl group, a pentyl group, and a hexyl group.

Examples of the alicyclic group having from 5 to 8 carbon atoms include a cyclopentyl group, a cyclohexyl group, a methylcyclohexyl group, a cycloheptyl group, and a cyclooctyl group.

Examples of the aralkyl group which has from 7 to 12 carbon atoms and may have a substituent group include a benzyl group, a 1-phenylethyl group, a 2-phenylethyl group, an α-naphthylmethyl group, and a β-naphthylmethyl group.

Examples of the substituent group include alkyl groups having from 1 to 6 carbon atoms such as methyl group, ethyl group, n-propyl group, isopropyl group, n-butyl group, isobutyl group, sec-butyl group, tert-butyl group, pentyl group, and hexyl group; alicyclic groups having from 5 to 8 carbon atoms such as cyclopentyl group, cyclohexyl group, and cycloheptyl group; perfluoroalkyl groups having from 1 to 4 carbon atoms such as trifluoromethyl group, pentafluoroethyl group, heptafluoropropyl group, and nonafluorobutyl group; alkoxy groups having from 1 to 4 carbon atoms such as methoxy group, ethoxy group, n-propoxyl group, isopropoxy group, n-butoxy group, isobutoxy group, sec-butoxy group, and tert-butoxy group; halogen atoms such as fluorine atom, chlorine atom, bromine atom, and iodine atom; aralkyl groups having from 7 to 12 carbon atoms such as benzyl group, phenylethyl group, and naphthylmethyl group; tri-$C_{1-6}$-alkylsilyl groups such as trimethylsilyl group, trimethylsilyl group, triisopropylsilyl group, dimethylisopropylsilyl group, diethylisopropylsilyl group, dimethyl(2,3-dimethyl-2-butyl)silyl group, tert-butyldimethylsilyl group, and dimethylhexylsilyl group; and dialkylamino groups having from 2 to 8 carbon atoms such as dimethylamino group, diethylamino group, and dibutylamino group In the above formulae, o represents an integer of from 0 to 40, preferably from 2 to 30.

The organoaluminumoxy compounds represented by the formulae (8) and (9) are compounds also called "aluminoxane". Of the aluminoxanes, methylaluminoxane, ethylaluminoxane, isobutylaluminoxane, and methylisobutylaluminoxane are preferred, with methylaluminoxane being particularly preferred. The above-mentioned aluminoxanes may be used in combination in each group or between groups. The above-mentioned aluminoxanes can be prepared under known various conditions.

The organoaluminumoxy compounds represented by the formula (10) can be obtained by reacting one or two or more trialkylaluminums represented by $(R^{13})_3Al$ with an alkylboronic acid represented by the formula: $R^{17}B(OH)_2$, at a ratio of from 10:1 to 1:1 (molar ratio).

The hydroxy compound to be used for the preparation of the organoaluminum compound is preferably at least one hydroxy compound selected from 2,6-diphenylphenol represented by the formula (4), 2,6,2',6'-tetraphenyl-biphenyl-4,4'-diol represented by the formula (5), 1,1'-binaphthyl-2,2'-diol represented by the formula (6), (2,2-dimethyl-1,3-dioxolane-4,5-diyl)bis(diphenylmethanol) represented by the formula (7), a diarylphenol represented by the following formula (11), a bis(diarylphenol) represented by the formula (12), a biaryldiol represented by the formula (13), a dimethanol represented by the formula (14), and a silanol represented by the formula (15).

[Chem. 32]

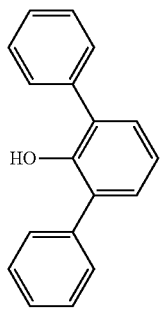

(4)

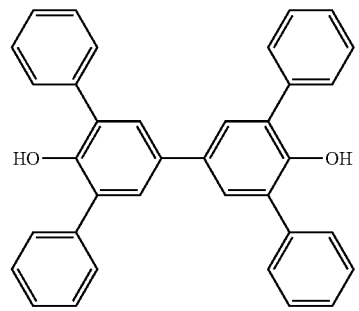

(5)

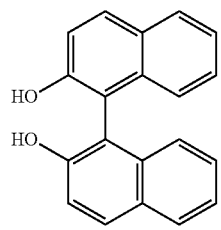

(6)

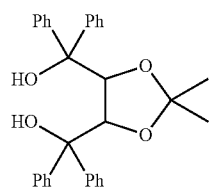

(7)

The 1,1'-binaphthyl-2,2'-diol represented by the formula (6) and the (2,2-dimethyl-1,3-dioxolane-4,5-diyl)bis(diphenylmethanol) represented by the formula (7) may be optically active.

[Chem. 33]

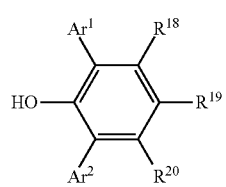

(11)

In the general formula (11), $Ar^1$ and $Ar^e$ each independently represent an aryl group which has from 6 to 15 carbon atoms and may have a substituent group or a heteroaryl group which has from 2 to 15 carbon atoms and may have a substituent group;

$R^{18}$, $R^{19}$, and $R^{20}$ each independently represent a hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group, or a polymer chain; and $R^{18}$ and $R^{19}$, or $R^{19}$ and $R^{20}$ may be bonded to each other to independently form a fused benzene ring, a fused substituted benzene ring, a trimethylene group, a tetramethylene group, a pentamethylene group, a methylenedioxy group, an ethylenedioxy group or a trimethylenedioxy group.

[Chem. 34]

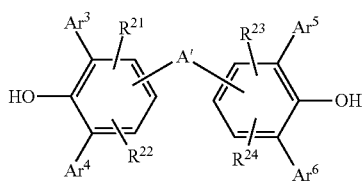

(12)

In the general formula (12), $Ar^3$, $Ar^4$, $Ar^5$, and $Ar^6$ each independently represent an aryl group which has from 6 to 15 carbon atoms and may have a substituent group or a heteroaryl group which has from 2 to 15 carbon atoms and may have a substituent group;

$R^{21}$, $R^{22}$, $R^{23}$ and $R^{24}$ each independently represent a hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group or a polymer chain; and $R^{21}$ and $R^{22}$, or $R^{23}$ and $R^{24}$ may be bonded to each other to independently form a fused benzene ring, a fused substituted benzene ring, a trimethylene group, a tetramethylene group, a pentamethylene group, a methylenedioxy group, an ethylenedioxy group or a trimethylenedioxy group; $R^{21}$ or $R^{22}$ and/or $R^{23}$ or $R^{24}$ may be bonded to A' to form an aromatic ring or a non-aromatic ring;

A' represents (1) a linear or branched and/or cyclic hydrocarbon group having from 1 to 25 carbon atoms, which may have a substituent group and/or an unsaturated bond; (2) an arylene group which has from 6 to 15 carbon atoms and may have a substituent group; (3) a heteroarylene group which has from 2 to 15 carbon atoms and may have a substituent group; or (5) a functional group or hetero element selected from the group consisting of —O—, —S—, —N($R^{25}$)—, —S(O)—, —C(O)—, —S(O)$_2$—, —P($R^{25}$)—, —($R^{25}$)P(O)— and —Si($R^{26}R^{27}$)— (wherein, $R^{25}$ to $R^{27}$ each independently represent an alkyl group having from 1 to 6 carbon atoms, an alicyclic group having from 5 to 8 carbon atoms, an aralkyl group which has from 7 to 12 carbon atoms and may have a substituent group, or an aryl group which has from 6 to 10 carbon atoms and may have a substituent group).

[Chem. 35]

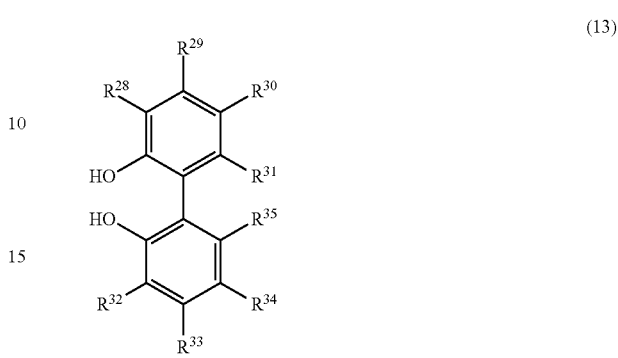

(13)

In the general formula (13), $R^{28}$, $R^{29}$, $R^{30}$, $R^{31}$, $R^{32}$, $R^{33}$, $R^{34}$, and $R^{35}$ each independently represent a hydrogen atom, an alkyl group having from 1 to 8 carbon atoms, a perfluoroalkyl group having from 1 to 4 carbon atoms, an alkoxy group having from 1 to 8 carbon atoms, an alicyclic group having from 5 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group or a polymer chain; and $R^{28}$ and $R^{29}$, $R^{29}$ and $R^{30}$, $R^{30}$ and $R^{31}$, $R^{31}$ and $R^{35}$, $R^{32}$ and $R^{33}$, $R^{33}$ and $R^{34}$, or $R^{34}$ and $R^{35}$ may be bonded to each other to independently form a fused benzene ring, a fused substituted benzene ring, a trimethylene group, a tetramethylene group, a pentamethylene group, a methylenedioxy group, an ethylenedioxy group, or a trimethylenedioxy group.

[Chem. 36]

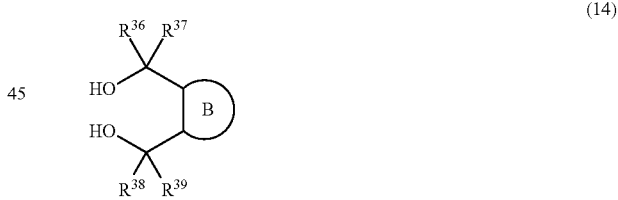

(14)

In the general formula (14), $R^{36}$, $R^{37}$, $R^{38}$, and $R^{39}$ each independently represent a hydrogen atom, an alkyl group having from 1 to 8 carbon atoms, an alicyclic group having from 5 to 8 carbon atoms, a perhalogenoalkyl group having from 1 to 8 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a heteroaryl group which has from 2 to 15 carbon atoms and may have a substituent group, a dialkylamino group having from 2 to 8 carbon atoms, a thioalkoxy group having from 1 to 4 carbon atoms, a nitro group or a polymer chain; and $R^{36}$ and $R^{37}$, and $R^{38}$ and $R^{39}$ may be bonded to each other to independently form a 3- to 9-membered ring which may have a hetero element; and ring B is a 3- to 8-membered ring which may have a hetero element.

[Chem. 37]

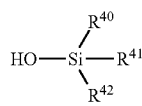

(15)

In the general formula (15), $R^{40}$, $R^{41}$, and $R^{42}$ each independently represent an alkyl group having from 1 to 10 carbon atoms, an alicyclic group having from 5 to 8 carbon atoms, an aralkyl group having from 7 to 12 carbon atoms, an aryl group which has from 6 to 10 carbon atoms and may have a substituent group, a heteroaryl group which has from 2 to 15 carbon atoms and may have a substituent group, or a polymer chain.

The following are examples of the predetermined substituent groups in the hydroxy compounds represented by the above formulae (11) to (15).

Examples of the aryl group which has from 6 to 15 carbon atoms and may have a substituent group include a benzyl group, an α-naphthyl group, and a β-naphthyl group.

Examples of the substituent group include alkyl groups having from 1 to 6 carbon atoms such as methyl group, ethyl group, n-propyl group, isopropyl group, n-butyl group, isobutyl group, sec-butyl group, tert-butyl group, pentyl group, and hexyl group; alicyclic groups having from 5 to 8 carbon atoms such as cyclopentyl group, cyclohexyl group, and cycloheptyl group; perfluoroalkyl groups having from 1 to 4 carbon atoms such as trifluoromethyl group, pentafluoroethyl group, heptafluoropropyl group, and nonafluorobutyl group; alkoxy groups having from 1 to 4 carbon atoms such as methoxy group, ethoxy group, n-propoxy group, isopropoxy group, n-butoxy group, isobutoxy group, sec-butoxy group, and tert-butoxy group; halogen atoms such as fluorine atome, chlorine atome, bromine atome, and iodine atome; aralkyl groups having from 7 to 12 carbon atoms such as benzyl group, phenylethyl group, and naphthylmethyl group; tri-($C_{1-6}$)alkylsilyl groups such as trimethylsilyl group, triethylsilyl group, triisopropylsilyl group, dimethylisopropylsilyl group, diethylisopropylsilyl group, dimethyl(2,3-dimethyl-2-butyl)silyl group, tert-butyldimethylsilyl group, and dimethylhexylsilyl group; and dialkylamino groups having from 2 to 8 carbon atoms such as dimethylamino group, diethylamino group, and dibutylamino group. Additional examples thereof include 6,6-nylon chain, vinyl polymer chain, and styrene polymer chain.

Examples of the heteroaryl group which has from 2 to 15 carbon atoms and may have a substituent group include a furyl group, a thienyl group, a pyronyl group, a benzofuryl group, an isobenzofuryl group, a benzothienyl group, an indolyl group, an isoindolyl group, a carbazoyl group, a pyridyl group, a quinolyl group, an isoquinolyl group, a pyrazyl group, and a ferrocenyl group. Examples of the substituent group include the substituent groups same as those exemplified above as the substituent groups of the aryl group.

Examples of the alkyl group having from 1 to 8 carbon atoms include a methyl group, an ethyl group, an n-propyl group, an isopropyl group, an n-butyl group, an isobutyl group, a sec-butyl group, a tert-butyl group, a pentyl group, a hexyl group, a heptyl group, and an octyl group.

Examples of the alicyclic group having from 5 to 8 carbon atoms include a cyclopentyl group, a cyclohexyl group, a methylcyclohexyl group, a cycloheptyl group, and a cyclooctyl group.

Example of the perfluoroalkyl group having from 1 to 4 carbon atoms include a trifluoromethyl group, a pentafluoroethyl group, a pentafluoropropyl group, and a nonafluorobutyl group.

Examples of the alkoxy group having from 1 to 8 carbon atoms include a methoxy group, an ethoxy group, an n-propoxyl group, an isopropoxy group, an n-butoxy group, an isobutoxy group, a sec-butoxy group, a tert-butoxy group, a pentoxy group, a hexoxy group, a heptoxy group, and octoxy group.

Examples of the aralkyl group which has from 7 to 12 carbon atoms and may have a substituent group include a benzyl group, a 1-phenylethyl group, a 2-phenylethyl group, an α-naphthylmethyl group, and β-naphthylmethyl group. Examples of the substituent group include the substituent groups same as those exemplified above as the substituent groups of the aryl group.

Examples of the halogen atom include a fluorine atom, a chlorine atom, a bromine atom, and an iodine atom.

Examples of the organosilyl group include a tri(substituted)silyl group. It has three substituent groups selected from alkyl groups having from 1 to 6 carbon atoms, aryl groups having from 6 to 18 carbon atoms, and aralkylsilyl groups having from 7 to 19 carbon atoms. They may be the same or different from each other. Examples of the alkyl group having from 1 to 6 carbon atoms include a methyl group, an ethyl group, an isopropyl group, a 2,3-dimethyl-2-butyl group, a hexyl group, and a tert-butyl group. Examples of the aryl group having from 6 to 18 carbon atoms include a phenyl group and a naphthyl group. Examples of the aralkyl group having from 7 to 19 carbon atoms include a benzyl group and a p-xylyl group.

Examples of the organosilyl group include tri(substituted) silyl groups, e.g., tri($C_{1-6}$)alkylsilyl groups such as trimethylsilyl group, trimethylsilyl group, triisopropylsilyl group, dimethylisopropylsilyl group, diethylisopropylsilyl group, dimethyl(2,3-dimethyl-2-butyl)silyl group, tert-butyldimethylsilyl group, and dimethylhexylsilyl group, di-($C_{1-6}$)alkyl-($C_{6-18}$)arylsilyl groups such as dimethylcumylsilyl group, di-($C_{6-18}$)aryl-($C_{1-6}$)alkylsilyl groups such as tert-butyldiphenylsilyl group and diphenylmethylsilyl group, tri-($C_{6-18}$)arylsilyl groups such as triphenylsilyl group, and tri($C_{7-19}$) aralkylsilyl groups such as tribenzylsilyl group and tri-p-xylylsilyl group.

Examples of the dialkylamino group having from 2 to 8 carbon atoms include a dimethylamino group, a diethylamino group, a dipropylamino group, a diisopropylamino group, and a dibutylamino group.

Examples of the thioalkyl group having from 1 to 4 carbon atoms include a methylthio group, an ethylthio group, an n-propylthio group, an isopropylthio group, an n-butylthio group, an isobutylthio group, a sec-butylthio group, and a tert-butylthio group.

Examples of the polymer chain include a 6,6-nylon chain, a vinyl polymer chain, and a styrene polymer chain.

In the formula (11), $R^{18}$ and $R^{19}$, or $R^{19}$ and $R^{20}$ may be bonded to each other to independently form a fused benzene ring, a fused substituted benzene ring, a trimethylene group, a tetramethylene group, pentamethylene group, a methylenedioxy group, an ethylenedioxy group, or a trimethylenedioxy group.

In the formula (12), $R^{21}$ and $R^{22}$, or $R^{23}$ and $R^{24}$ may be bonded to each other to independently form a fused benzene ring, a fused substituted benzene ring, a trimethylene group, a tetramethylene group, a pentamethylene group, a methylenedioxy group, an ethylenedioxy group, or a trimethylenedioxy group.

In the formula (13), $R^{28}$ and $R^{29}$, $R^{29}$ and $R^{30}$, $R^{30}$ and $R^{31}$, $R^{31}$ and $R^{35}$, $R^{32}$ and $R^{33}$, $R^{33}$ and $R^{34}$, or $R^{34}$ and $R^{35}$ may be bonded to each other to independently form a fused benzene ring, a fused substituted benzene ring, a trimethylene group, a tetramethylene group, a pentamethylene group, a methylenedioxy group, an ethylenedioxy group, or a trimethylenedioxy group.

The fused benzene ring, fused substituted benzene ring, trimethylene group, tetramethylene group, pentamethylene group, methylenedioxy group, ethylenedioxy group, or trimethylenedioxy group may have an inert functional group as a substituent group and it may have preferably from 0 to 4 substituent groups. Examples of the substituent group include the substituent groups same as those exemplified above as the substituent groups of the aryl group.

Via a substituent group or carbon chain present in the fused benzene ring, fused substituted benzene ring, trimethylene group, tetramethylene group, pentamethylene group, methylenedioxy group, ethylenedioxy group, or trimethylenedioxy group, at least one compound selected from the hydroxy compounds represented by the formula (11), formula (12), and formula (13) may form a polymer.

In the formula (12), $R^{21}$ or $R^{22}$ and/or $R^{23}$ or $R^{24}$ may form a cyclic aromatic or nonaromatic ring together with A'. In this case, the bis(diarylphenol) represented by the formula (12) to be used in the present invention has a tricyclic basic structure, for example, an anthracene basic structure having the formula (12a) or a basic structure of the formula (12b).

[Chem. 38]

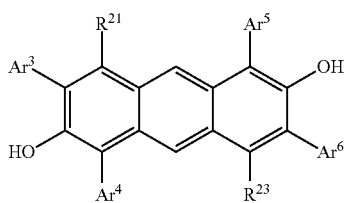

(12a)

[Chem. 39]

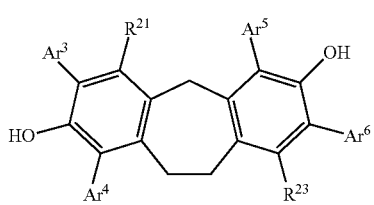

(12b)

The tricyclic basic structure in the formula (12a) or the formula (12b) may have a hetero element in the basic structure.

As described above, in the formula (12), A' represents (1) a linear or branched and/or cyclic hydrocarbon group which has from 1 to 25 carbon atoms and may have a substituent group and/or an unsaturated bond, (2) an aryl group which has from 6 to 15 carbon atoms and may have a substituent group; (3) a heteroaryl group which has from 2 to 15 carbon atoms and may have a substituent group; or (4) a functional group or hetero element selected from the group consisting of —O—, —S—, —N($R^{25}$)—, —S(O)—, —C(O)—, —S(O)$_2$—, —P($R^{25}$)—, —($R^{25}$)P(O)—, and —Si($R^{26}R^{27}$)—, wherein, $R^{25}$ to $R^{27}$ each independently represent an alkyl group having from 1 to 6 carbon atoms, an alicyclic group having from 5 to 8 carbon atoms, an aralkyl group which has from 7 to 12 carbon atoms and may have a substituent group, or an aryl group which has from 6 to 10 carbon atoms and may have a substituent group.

Examples of the linear or branched and/or cyclic hydrocarbon group which has from 1 to 25 carbon atoms and may have a substituent group and/or an unsaturated bond (1) as A' in the formula (12) include the following structures 1 to 44. It is to be noted that the wavy line shows a bonded site to the remaining site of the structure represented by the formula (12) disclosed herein.

[Chem. 40]

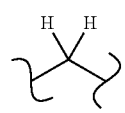
1

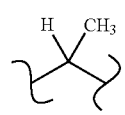
2

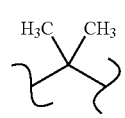
3

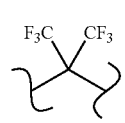
4

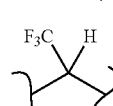
5

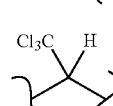
6

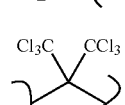
7

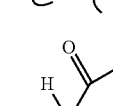
8

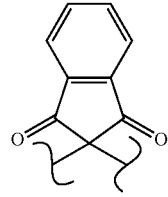
9

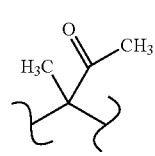
10

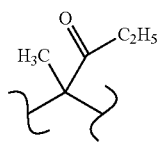
11
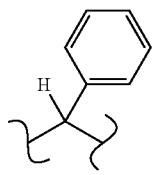
12
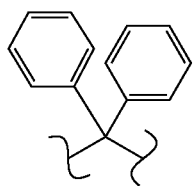
13
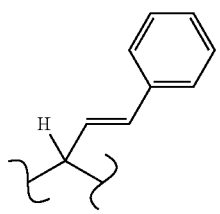
14
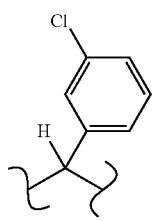
15
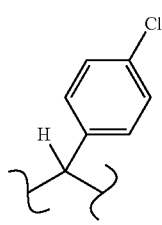
16
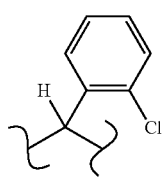
17
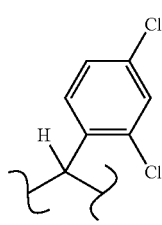
18
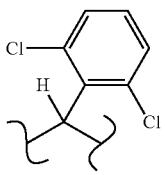
19
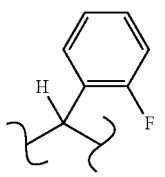
20
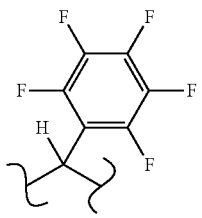
21
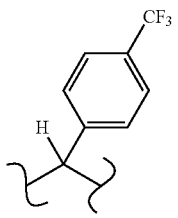
22
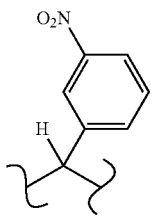
23
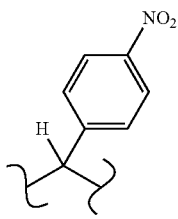
24
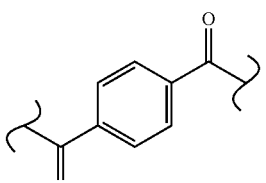
25
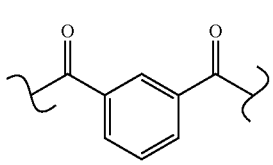
26

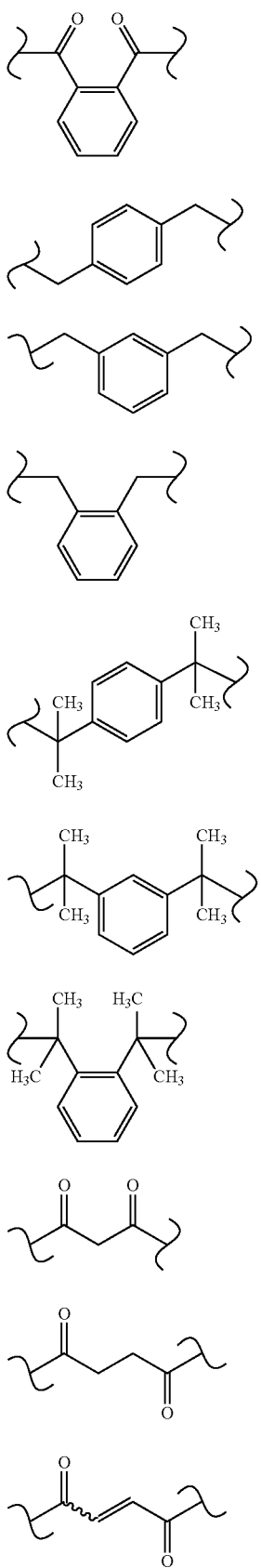

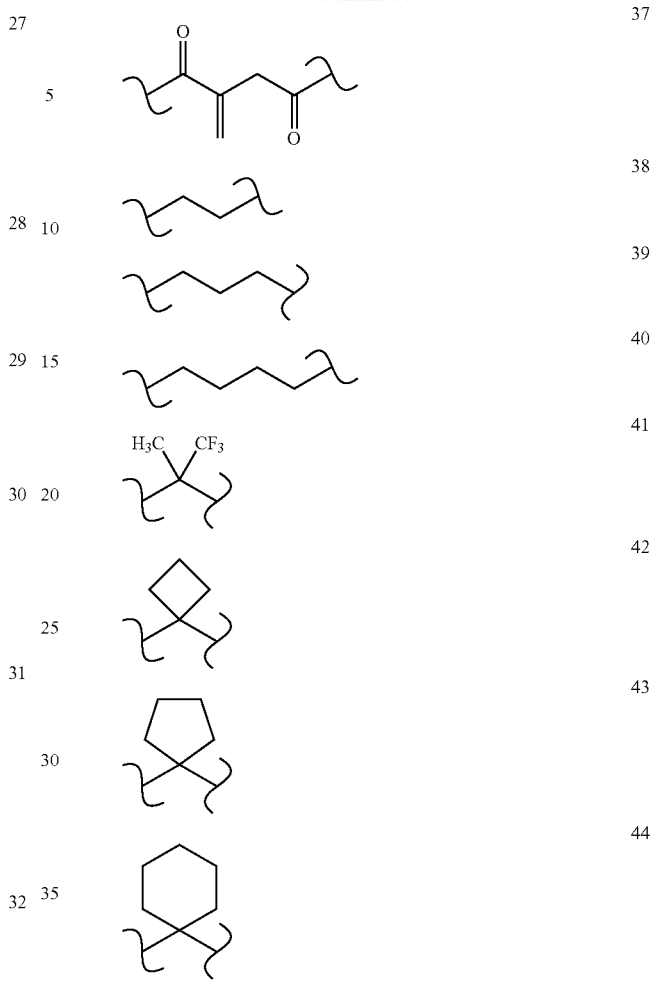

The above structures 1 to 44 may have a substituent group and examples of the substituent group include the substituent groups same as those exemplified above as the substituent groups of the aryl group.

Examples of the (2) arylene group which has from 6 to 15 carbon atoms and may have a substituent group as A' in the formula (12) include a phenylene group, a naphthylene group, and an anthracenylene group.

Examples of the (3) heteroarylene group which has from 2 to 15 carbon atoms and may have a substituent group as A' in the formula (12) include a furylene group, a thienylene group, a pyronylene group, a benzofurylene group, an isobenzofurylene group, a benzothienylene group, an indolylene group, an isoindolylene group, a carbazoylene group, a pyrizylene group, a quinolylene group, an isoquinolylene group, a pyrazylene group, and a ferrocenylene group.

The arylene group and heteroarylene group may have a substituent group, and examples of the substituent group include the substituent groups same as those exemplified above as the substituent groups of the aryl group.

The A' in the formula (12) is (4) a functional group or a hetero element selected from the group consisting of —O—, —S—, —N($R^{25}$)—, —S(O)—, —C(O)—, —S(O)$_2$—, —P($R^{25}$)—, —($R^{25}$)P(O)— and —Si($R^{26}R^{27}$)— [wherein $R^{25}$ to $R^{27}$ each independently represent an alkyl group having from 1 to 6 carbon atoms, an alicyclic group having from 5 to 8 carbon atoms, an aralkyl group which has from 7 to 12 carbon atoms and may have a substituent group or an aryl group which has from 6 to 10 carbon atoms and may have a substituent group]. The A' is preferably —O—, —S—, —S(O)—, —S(O)$_2$— or —Si($R^{26}R^{27}$)—.

In the formula (14), $R^{36}$ and $R^{37}$, and $R^{38}$ and $R^{39}$ may be bonded to each other to form a 3- to 9-membered ring which may have a hetero element. In this case, examples of the hetero element include oxygen, nitrogen, phosphorus, sulfur, boron, and silicon and metal elements capable of forming a metallocycle. The ring B may have a plurality of the hetero elements, and in this case, the hetero elements may be the same or different from each other. The ring B may have a substituent group or the hetero element may have a substituent group.

Specific examples of the 3- to 9-memtered ring which may have a hetero element include a cyclopropane ring, a cyclobutane ring, a cyclopentane ring, a cyclohexane ring, a cycloheptane ring, a cyclooctane ring, a benzene ring, a naphthalene ring, a norbornane ring, a norbornene ring, a decalin ring, a furan ring, a tetrahydrofuran ring, a dioxolane ring, a dioxane ring, a dioxacycloheptane ring, a trioxacycloheptane ring, a lactone ring, a lactam ring, a morpholine ring, a pyrropidine ring, a piperidine ring, a pyrazine ring, a thiophene ring, and a tetrahydrothiophene ring.

Examples of the substituent group include the substituent groups same as those exemplified above as the substituent groups of the aryl group.

The hydroxy compound represented by the formula (14) may form a polymer via the substituent group or carbon chain present in the 3- to 9-membered ring formed.

In the formula (14), the ring B is a 3- to 8-membered ring which may have a hetero element. In this case, examples of the hetero element include oxygen, nitrogen, phosphorus, sulfur, boron, silicon, and a metal element capable of forming a metallocycle. The ring B may have a plurality of the hetero elements, and in this case, the hetero elements may be the same or different from each other. The ring B may have a substituent group or the hetero element may have a substituent group.

Specific examples of the ring B include a cyclopropane ring, a cyclobutane ring, a cyclopentane ring, a cyclohexane ring, a cycloheptane ring, a cyclooctane ring, a benzene ring, a naphthalene ring, a norbornane ring, a norbornene ring, a decalin ring, a furan ring, a tetrahydrofuran ring, a dioxolane ring, a dioxane ring, a dioxacycloheptane ring, a trioxacycloheptane ring, a lactone ring, a lactam ring, a morpholine ring, a pyrropidine ring, a piperidine ring, a pyrazine ring, a thiophene ring, and a tetrahydrothiophene ring.

Examples of the substituent group include the substituent groups same as those exemplified above as the substituent group of the aryl group.

The hydroxy compound represented by the formula (14) may form a polymer via the substituent group or carbon chain present in the ring B.

The diarylphenol represented by the formula (11) are described, for example, in Patent Document 7.

Preferred examples of the diarylphenol represented by the formula (11) include 2,6-diphenylphenol, 2,6-di(4-fluorophenyl)phenol, 2,6-di(3,4-difluorophenyl)phenol, 2,6-di(3,4,5-trifluorophenyl)phenol, 2,6-diphenyl-4-methylphenol, 2,6-diphenyl-3,5-dimethylphenol, 2,6-di(2-methylphenyl)-3,5-dimethylphenol, 2,6-di(2-isopropylphenyl)-3,5-dimethylphenol, 2,6-di(α-naphthyl)-3,5-dimethylphenol, 3-phenyl-1,1'-binaphthyl-2-ol, 3-(4-fluorophenyl)-1,1'-binaphthyl-2-ol, 1,3-diphenyl-2-naphthol, and 3,3',5,5'-tetraphenylbiphenyl-4,4'-diol.

The bis(diarylphenol) represented by the formula (12) are described, for example, in Patent Document 8 [which is incorporated herein by reference].

In the bis(diarylphenol) represented by the formula (12), preferred examples of $R^{21}$, $R^{22}$, $R^{23}$, and $R^{24}$ include a hydrogen atom, a methyl group, an ethyl group, an isopropyl group, a halogen atom (fluorine atom, chlorine atom), a trifluoromethyl group, a phenyl group, a methoxy group, and a nitro group. More preferably, $R^{21}$, $R^{22}$, $R^{23}$, and $R^{24}$ are the same and particularly preferably, they represent a hydrogen atom.

Preferred examples of $Ar^3$, $Ar^4$, $Ar^5$, and $Ar^6$ include a phenyl group, a naphthyl group, a 4-fluorophenyl group, a 4-chlorophenyl group, a 3-chlorophenyl group, a 3,5-dichlorophenyl group, a 4-methylphenyl group, a 3-trifluoromethylphenyl group, and a 4-trifluoromethylphenyl group. More preferably, $Ar^3$, $Ar^4$, $Ar^5$, and $Ar^6$ are the same and particularly preferably, they represent a phenyl group.

Preferred examples of the A' include a single bond and the above-mentioned structures 1 to 44, with the above-mentioned structures 1 to 5 being more preferred.

The biaryldiol represented by the formula (13) are described, for example, in Patent Document 8 [which is incorporated herein by reference].

Preferred examples of the diarylphenol represented by the formula (13) include, but not limited to, the following compounds.

[Chem. 41]

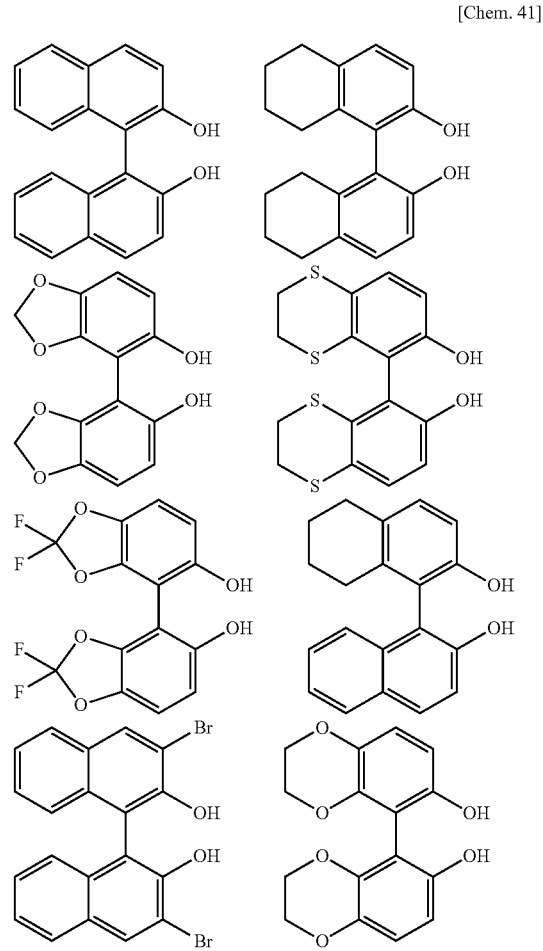

-continued
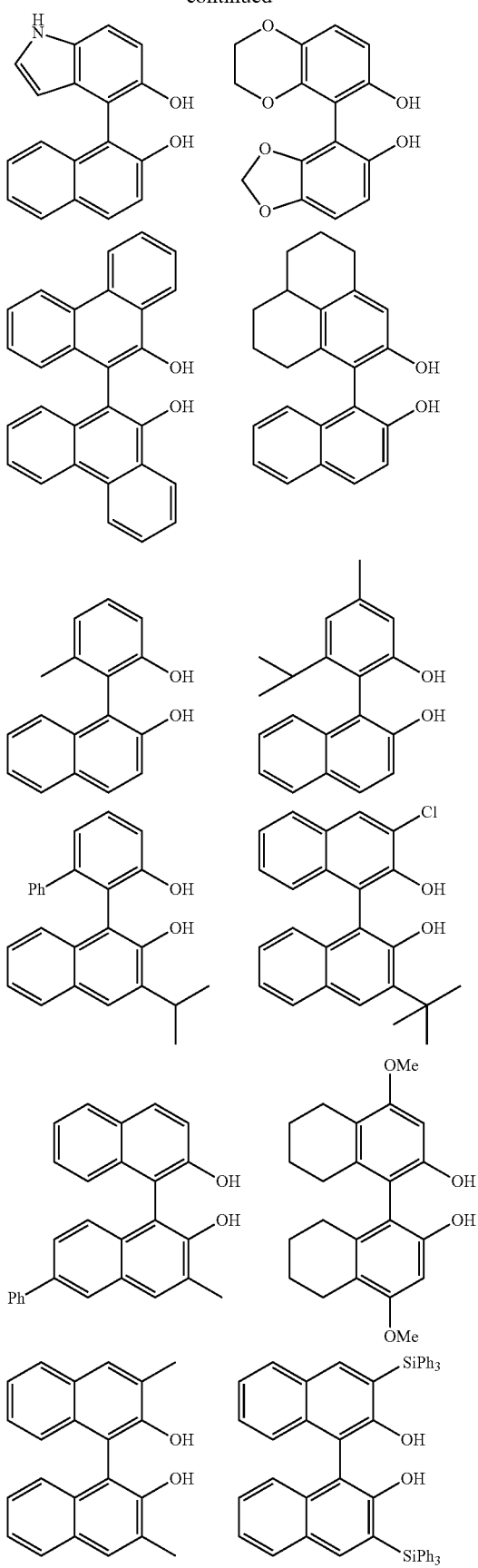
-continued
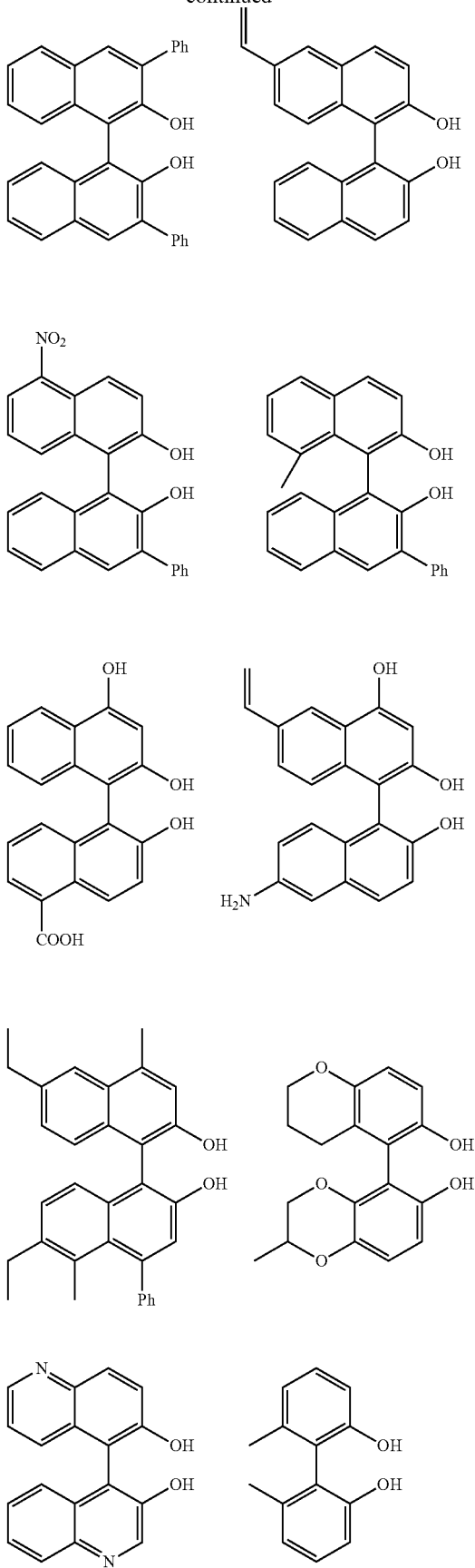

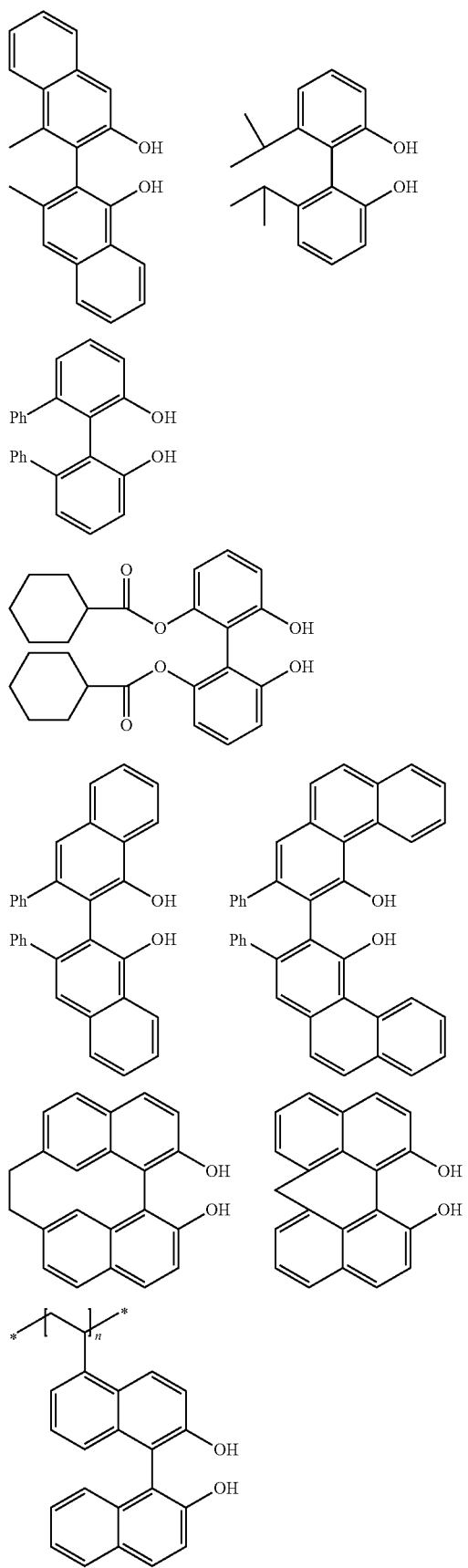
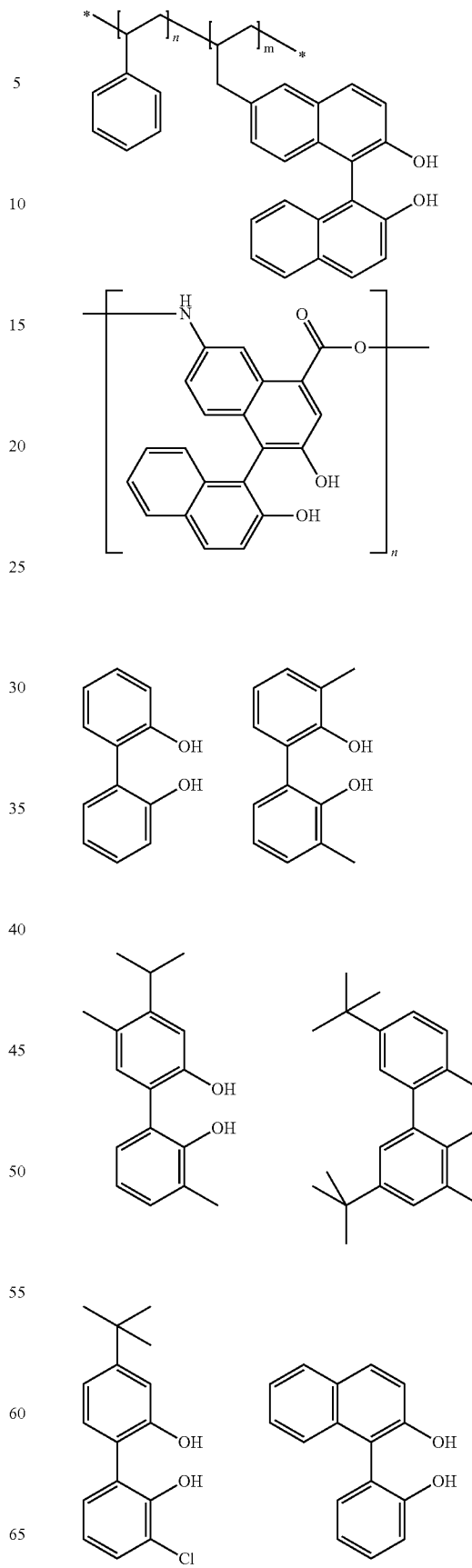
[Chem. 42]

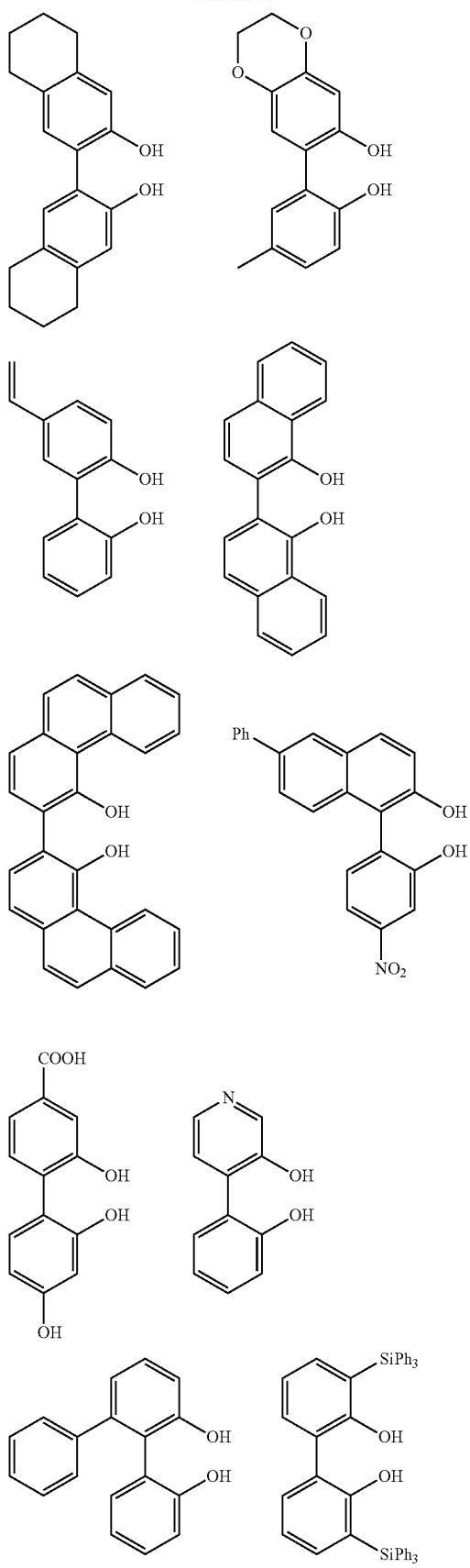
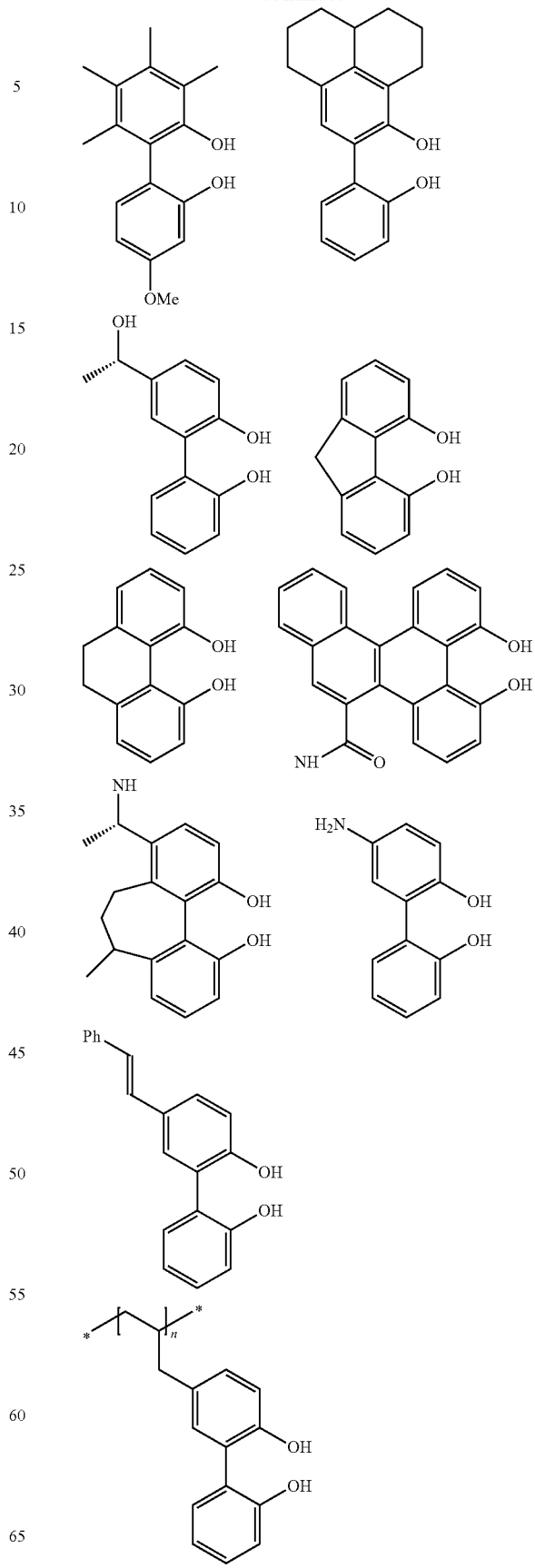

-continued

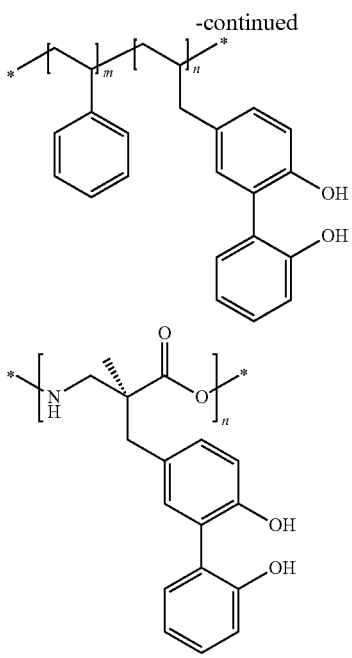

The dimethanol represented by the formula (14) are described, for example, in U.S. Pat. No. 6,166,260, and Synlett, 1998, pp. 1291-1293; Tetrahedron: Asymmetry, 1991, Vol. 2, No. 12, pp. 1295-1304; CROATIA CHEMICA ACTA, 1996, 69, pp. 459-484; and Russian Chemical Bulletin, 2000, 49, pp. 460-465 [which is incorporated herein by reference].

Preferred examples of the dimethanol represented by the formula (14) include, but not limited to, 2,2-dimethyl-α,α,α', α'-tetraphenyl-1,3-dioxolane-4,5-dimethanol (TADDOL) and 2,2-dimethyl-α,α,α',α'-tetra(1-naphthyl)-1,3-dioxolane-4,5-dimethanol (NAPHTADDOL).

The silanol represented by the formula (15) are described, for example, in WO 2007/039342 and WO 2007/039366 [which is incorporated here by reference].

Examples of the preferred silanol represented by the formula (15) include, but not limited to, trimethylsilanol, triethylsilanol, tert-butyldimethylsilanol, triphenylsilanol, and tri-naphthylsilanol.

The organoaluminum catalyst to be used in Step B of the present invention is obtained by reacting at least one compound selected from the trialkylaluminum represented by the formula (3) and the organoaluminumoxy compounds represented by the formulae (8) to (10) with at least one compound selected from the hydroxy compounds represented by the formulae (4) to (7) and (11) to (15).

In this case, with at least one compound selected from the trialkylaluminum represented by the formula (3) and the organoaluminumoxy compounds represented by the formulae (8) to (10), at least one compound selected from the hydroxy compounds represented by the formulas (4) to (7) and (11) to (15) is reacted in a ratio (ratio of aluminum atom:compound) of preferably from 0.25 to 10 equivalents, more preferably from 0.5 to 4 equivalents, in an inert gas atmosphere.

The above-mentioned reaction can be conducted in the presence of an inert solvent. Examples of the solvent include aliphatic hydrocarbons (such as hexane, heptane, and octane), alicyclic hydrocarbons (such as cyclohexane and methylcyclohexane), aromatic hydrocarbons (such as benzene, toluene, and xylene), ethers (such as diethyl ether, diisopropyl ether, dimethoxyethane, methyl tert-butyl ether, tetrahydrofuran, dioxane, and dioxolane), and halogenated hydrocarbons (such as dichloromethane, dichloroethane, and chlorobenzene). Of those, the preferred solvent is an organic solvent such as toluene, heptane, and dichloromethane. These solvents are preferably pre-dried or anhydrous ones.

The used amount (L) of the solvent is preferably from 1 to 10000 times volume [L/kg], more preferably from 20 to 400 times volume [L/kg] per weight (kg) of the hydroxy compound. The degree of polymerization of aluminoxane is preferably 2 or greater.

The reaction temperature is preferably from about −60 to 100° C., more preferably from about −30 to 50° C., particularly preferably from about −5 to 30° C. The reaction is conducted for preferably from about 0.25 to 30 hours, more preferably from about 0.5 to 10 hours, while keeping the above temperature. This enables smooth preparation of the organoaluminum catalyst.

The organoaluminum catalyst of the present invention has an excellent effect as a catalyst in conducting the ring-closure reaction of citronellal.

<Step B: Ring-Closure Reaction of Optically Active Citronellal>

In the present invention, a ring-closure reaction of an optically active citronellal is conducted in the presence of the above-mentioned catalyst to thereby obtain an optically active isopulegol.

As a raw material compound, an optically active citronellal prepared in Step A is used.

An amount of the organoaluminum catalyst to be used as a catalyst in the ring-closure reaction of the optically active citronellal in Step B is preferably within a range of from about 0.05 to 10 mol %, more preferably from about 0.1 to 2 mol %, based on citronellal.

With regard to the catalyst to be used in the ring-closure reaction of citronellal in the present invention, the following methods: a) preliminarily mixing, in a reaction system, at least one compound selected from organoaluminum compounds represented by the formulae (3) and (8) to (10) and at least one compound selected from the hydroxy compounds represented by the formulae (4) to (7) and (11) to (15), particularly those selected from the formulae (4) to (7), to thereby prepare a catalyst (organoaluminum compound) and then adding citronellal; and b) separately adding an organoaluminum catalyst prepared in advance by mixing the organoaluminum compound and the hydroxy compound and citronellal during the ring-closure reaction can be used, and similar effects can be achieved by using either of these methods.

The ring-closure reaction of citronellal is conducted preferably within a temperature range of from about −60 to 100° C., more preferably from about −30 to 50° C., particularly preferably from −5 to 20° C. Isopulegol shown in Step B of Scheme 1 can be prepared smoothly by reacting for preferably from about 0.25 to 30 hours, more preferably from 0.5 to 20 hours while keeping the above-mentioned temperature.

The ring-closure reaction of citronellal in the present invention can be conducted under solventless conditions or in the presence of an inert solvent.

Although no particular limitation is imposed on the solvent to be used for the ring-closure reaction insofar as it does not markedly inhibit the reaction, examples thereof include aliphatic hydrocarbons (such as hexane, heptane, and octane), alicyclic hydrocarbons (such as cyclohexane and methylcyclohexane), aromatic hydrocarbons (such as benzene, toluene, and xylene), ethers (such as diethyl ether, diisopropyl ether, dimethoxyethane, methyl tert-butyl ether, tetrahydrofuran, dioxane, and dioxolane), and halogenated hydrocarbons (such as dichloromethane, dichloroethane, and chlorobenzene). Of those, organic solvents such as toluene, heptane, and dichloromethane are preferred. These solvents are preferably pre-dried or anhydrous ones.

The used amount (L) of the solvent is preferably from about 0 to 20 times volume [L/kg], more preferably from 0.5 to 7 times volume [L/kg] per weight (kg) of citronellal.

In order to suppress the side reaction during the ring-closure reaction, any of vinyl ethers, ketones, aldehydes, acid compounds, or basic compounds may be added.

Specific examples of the vinyl ethers include methyl vinyl ether, ethyl vinyl ether, isobutyl vinyl ether, and 3,4-dihydro-2H-pyran. Specific examples of the ketones include 1,1,1-trifluoroacetone, 1,1,1-trifluoroacetophenone, hexafluoroacetone, methyl pyruvate, and ethyl pyruvate. Specific examples of the aldehydes include acetaldehyde, propionaldehyde, and chloral (trichloroacetaldehyde).

Specific examples of the ketones include 1,1,1-trifluoroacetone, 1,1,1-trifluoroacetophenone, methyl pyruvate, ethyl pyruvate, and hexafluoroacetone.

Specific examples of the aldehydes include acetaldehyde, propionaldehyde, and chloral.

Specific examples of the acid compound include mineral acids (such as phosphoric acid, hydrochloric acid, and sulfuric acid), organic acids (such as formic acid, acetic acid, propionic acid, decanoic acid, citronellic acid, geranic acid, and nerylic acid), and organic acid anhydrides (such as acetic anhydride, propionic anhydride, pivalic anhydride, maleic anhydride, succinic anhydride, pivaloyl anhydride, and benzoic anhydride). Specific examples of the basic compounds include inorganic bases (such as lithium hydroxide, sodium hydroxide, potassium hydroxide, lithium carbonate, sodium carbonate, and potassium carbonate) and organic bases (such as trimethylamine and triethylamine).

The vinyl ethers, ketones, aldehydes, acid compounds, or basic compounds may be added in an amount of from 0.01 to 5 mol %, more preferably from 0.05 to 2 mol % based on the amount of citronellal (mol).

The ring-closure reaction is conducted preferably in an inert gas atmosphere such as nitrogen gas or argon gas. This enables smooth progress of the ring-closure reaction.

After completion of the reaction, general after-treatments may be conducted. A high-purity optically active isopulegol can be obtained by purifying the optically active isopulegol obtained in Step B of Scheme 1 by simple distillation or deep cooling crystallization.

On the other hand, when the organoaluminum catalyst of the present invention sparingly soluble in a solvent is used, it is possible to conduct the ring-closure reaction continuously by subjecting the solution which has finished the reaction to decantation to remove the isopulegol thus obtained and adding citronellal therein. Alternatively, such a catalyst is filtered off after completion of the ring-closure reaction and then, provided for the subsequent ring-closure reaction.

When the organoaluminum catalyst is partially deactivated, an amount of the catalyst corresponding to the deactivated portion is added to the reaction solution and the resulting mixture is then provided for the subsequent ring-closure reaction.

The ligand of all the organoaluminum compounds can be used again as a catalyst by treating the catalyst layer with an acid or alkali after catalyst deactivation and recovering it by recrystallization.

<Step D>
Steps D-3, 4, 7, 8, 11, 12, 15, and 16 shown in Scheme 1 of the present invention includes crystallizing the optically active isopulegol obtained in Step B at low temperatures (deep cooling crystallization) to thereby prepare an optically active isopulegol with higher chemical purity and optical purity.

[Chem. 43]

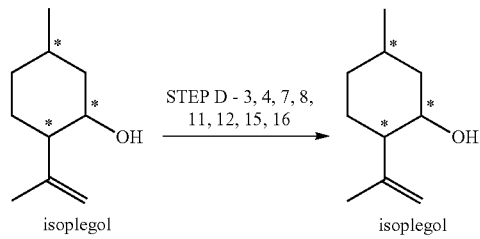

<Steps D-3, 4, 7, 8, 11, 12, 15, and 16: Deep Cooling Crystallization of Optically Active Isopulegol>

The deep cooling crystallization of the optically active isopulegol is described, for example, in Japanese Patent No. 3241542 [which is incorporated herein by reference].

A solution of the optically active isopulegol obtained in Step B dissolved in an organic solvent is crystallized at low temperatures (deep cooling crystallization) to thereby obtain an optically active isopulegol having a chemical purity and an optical purity of 99.7% or greater.

The deep cooling crystallization of the optically active isopulegol is conducted preferably at a temperature range of from about −60 to −20° C., particularly preferably a temperature range of from about −50 to −25° C. While gradually decreasing the temperature, crystals of an optically active isopulegol having a chemical purity and an optical purity, each 99.7% or greater, are precipitated, stirred and aged. In order to increase the precipitation rate of crystals, a small amount of crystals of the optically active isopulegol having a chemical purity and an optical purity, each 99.7% or greater, may be added.

The crystallization time is preferably for from about 1 to 30 hours, more preferably from about 10 to 20 hours. Then, the high-purity isopulegol thus precipitated is filtered using a centrifuge to thereby prepare a high-purity optically active isopulegol represented by Step D-3, 4, 7, 8, 11, 12, 15, and 16 of Scheme 1.

Although no particular limitation is imposed on the solvent to be used for the crystallization, examples thereof include aliphatic hydrocarbons (such as hexane, heptane, octane, and petroleum ether), alicyclic hydrocarbons (such as cyclohexane and methylcyclohexane), aromatic hydrocarbons (such as benzene, toluene, and xylene), ethers (such as diethyl ether, diisopropyl ether, dimethoxyethane, methyl tert-butyl ether, tetrahydrofuran, dioxane, and dioxolane), alcohols (such as methanol, ethanol, and isopropanol), and ketones (such as acetone and methyl ethyl ketone), and mixed solvents thereof. Of those, organic solvents such as heptane, petroleum ether, and acetone are preferred. These solvents are preferably pre-dried or anhydrous ones.

The used amount (L) of the solvent is preferably from about 0.5 to 5 times volume [L/kg], more preferably from 1 to 3 times volume [L/kg] per weight (kg) of isopulegol (kg).

A high-purity optically active isopulegol which is odorless and provides only refresh feeling can be industrialized by precision distillation with from 5 to 50 theoretical stages. When the optically active isopulegol is subjected to precision distillation prior to deep cooling crystallization, a high-purity optically active isopulegol which is odorless and provides only refresh feeling can be produced by simple distillation after deep cooling crystallization.

<Step C and Step E>

Step C-1, 2, 5, 6, 9, 10, 13, 14 and Step E-3, 4, 7, 8, 11, 12, 15, 16 shown in Scheme 1 of the present invention includes hydrogenating the optically active isopulegol obtained in Step B or Step D in the presence of a catalyst to thereby prepare an optically active menthol.

[Chem. 44]

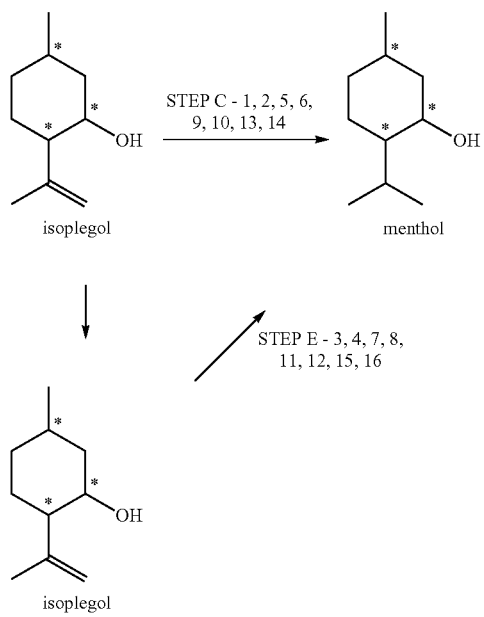

<Step C-1, 2, 5, 6, 9, 10, 13, 14 and Step E-3, 4, 7, 8, 11, 12, 15, 16: Hydrogenation Reaction of Optically Active Isopulegol>

A carbon-carbon double pond portion of the optically active isopulegol can be hydrogenated by a general process. More specifically, an optically active menthol can be prepared by adding a catalyst having hydrogenating ability such as Raney nickel or Pd/C in an autoclave and hydrogenating the optically active isopulegol in a solventless manner or applying a hydrogen pressure in the presence of a solvent.

The optically active isopulegol is hydrogenated at a temperature range of preferably from about 0 to 80° C., particularly preferably from about 20 to 60° C. The reaction time is preferably from about 1 to 30 hours, more preferably from about 3 to 15 hours. The optically active menthol thus obtained is then filtered and distilled to thereby complete the production method of an optically active menthol.

Although no particular limitation is imposed on the solvent used for the above reaction, examples thereof include aliphatic hydrocarbons (such as hexane, heptane, octane, and petroleum ether), alicyclic hydrocarbons (such as cyclohexane and methylcyclohexane), aromatic hydrocarbons (such as benzene, toluene, and xylene), ethers (such as diethyl ether, diisopropyl ether, dimethoxyethane, methyl tert-butyl ether, tetrahydrofuran, dioxane, and dioxolane), alcohols (such as methanol, ethanol, and isopropanol), and ketones (such as acetone and methyl ethyl ketone), and mixed solvents thereof. Of those, organic solvents such as heptane, petroleum ether, and acetone are preferred. These solvents are preferably pre-dried or anhydrous ones.

The used amount (L) of the solvent is preferably from about 0 to 5 times volume [L/kg], more preferably from 0 to 3 times volume [L/kg] per weight (kg) of an optically active menthol (kg).

As described above, according to the production method of the present invention, an optically active menthol can be obtained by a) using a predetermined metal powder or metal-supported substance, a predetermined optically active cyclic nitrogen-containing compound, and an acid and thereby asymmetrically hydrogenating citral (mixture of geranial and neral in any ratio) under a hydrogen pressure as low as about atmospheric pressure without taking out high-purity geranial or high-purity neral to thereby obtain a corresponding optically active citronellal; b) ring-closing the resulting optically active citronellal in the presence of a predetermined aluminum catalyst to thereby obtain an optically active isopulegol or subjecting the optically active isopulegol thus obtained to deep cooling crystallization to thereby obtain a high-purity optically active isopulegol, and c) hydrogenating the resulting product. This means that an optically active menthol can be produced in fewer steps from citral.

EXAMPLES

The present invention will hereinafter be described specifically by Examples and Comparative Examples. It should however be borne in mind that the present invention is not limited to or by them.

Measurement of products was conducted using gas chromatography (GLC). It was conducted under the following conditions:

Analyzer used: GC-2010 gas chromatograph manufactured by Shimadzu Corp.

Column:

Measurement of conversion ratio of citral: DB-WAX (0.25 mm×30 m), manufactured by Agilent Corp.

Measurement of optical purity of citronellal: β-DEX-225 (0.25 mm×30 m), manufactured by SUPELCO Corp.

Measurement of optical purity of isopulegol: β-DEX-325 (0.25 mm×30 m), manufactured by SUPELCO Corp.

Detector: FID $^1$H-NMR: 300 MHz, manufactured by Varian Inc.

Of the optically active cyclic nitrogen-containing compounds represented by the formula (1), compounds used in Examples 1 to 27 except Example 10 were synthesized in the following process. In Example 10, a compound manufactured by Aldrich was used.

Scheme 2

[Chem. 45]

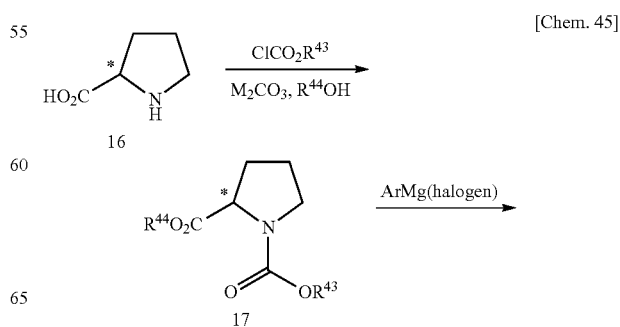

-continued

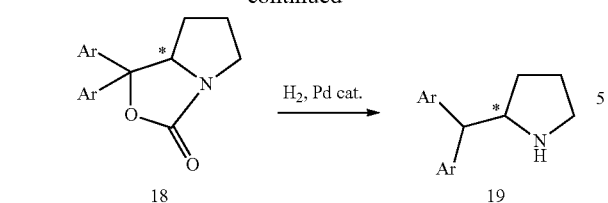

Scheme 3

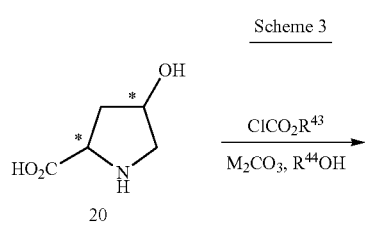

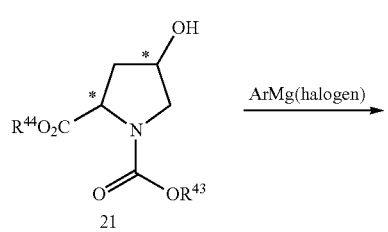

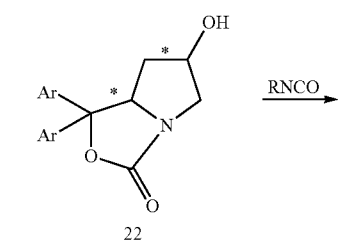

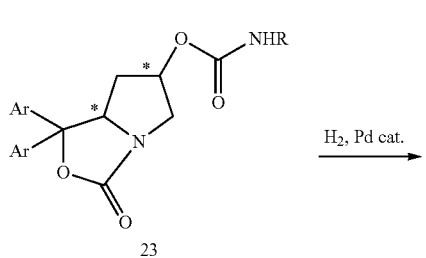

Synthesis Example 1

Synthesis of (R)-proline-N-ethyl carbamate methyl ester

[Chem. 46]

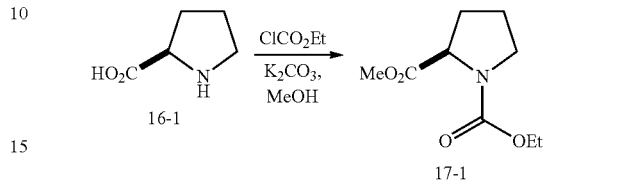

The synthesis was conducted according to the synthesis process described in Tetrahedron, Vol. 49, No. 23, 5127-5132.

In a 2 L four-necked flask were added 35.54 g (0.3 mol) of (R)-proline, 600 mL of anhydrous methanol, and 41.46 g of potassium carbonate, followed by stirring. Under ice cooling, 71.62 g (0.66 mmol) of ethyl chlorocarbonate was added dropwise to the reaction mixture at 25° C. or less and the resulting mixture was stirred at 0° C. for 12 hours. Then, the methanol was distilled off and 300 mL of water was added in the residue. The mixture was extracted with 450 mL of chloroform. Then, the aqueous layer was extracted twice with 450 mL of chloroform. The organic layer thus obtained was washed with saturated saline, dried over anhydrous magnesium sulfate, and filtered. Then, the solvent was distilled off to obtain 52.85 g of the intended product in a yield of 87.5%.

Synthesis Example 2

Synthesis of (S)-proline-N-ethyl carbamate methyl ester

[Chem. 47]

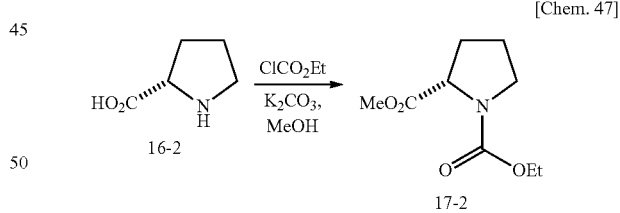

The synthesis was conducted according to the synthesis process described in Tetrahedron, Vol. 49, No. 23, 5127-5132.

In a 1 L four-necked flask were added 23.03 g (0.2 mol) of (S)-proline, 400 mL of anhydrous methanol, and 27.64 g of potassium carbonate, followed by stirring. Under ice cooling, 47.75 g (0.44 mmol) of ethyl chlorocarbonate was added dropwise to the reaction mixture at 25° C. or less and the resulting mixture was stirred at 0° C. for 12 hours. Then, the methanol was distilled off and 200 mL of water was added in the residue. The resulting mixture was extracted with 300 mL of chloroform. Then, the aqueous layer was extracted twice with 300 mL of chloroform. The organic layer thus obtained was washed with saturated saline, dried over anhydrous magnesium sulfate, and filtered. Then, the solvent was distilled off to obtain 35.85 g of the intended product in a yield of 89.1%.

Synthesis Example 3

Synthesis of (R)-2-(bis-(4'-t-butylphenyl)methyl) pyrrolidine (Synthesis of Optically Active Cyclic Nitrogen-Containing Compounds of Examples 1 to 6)

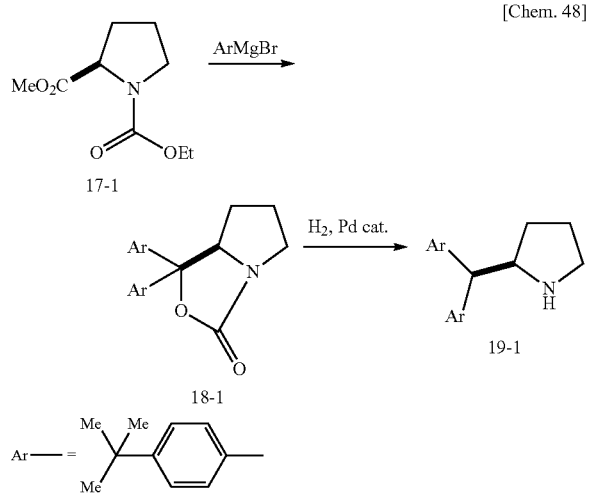

The synthesis was conducted according to the synthesis process of (S)-2-(diphenylmethyl)pyrrolidine described in Tetrahedron: Asymmetry, Vol. 8, No. 1, 149-153.

In a 1-L reaction flask purged with nitrogen were added 12.55 g (469 mmol) of magnesium and 50 mL of anhydrous THF in a nitrogen gas stream and the resulting mixture was stirred. At room temperature, a THF (500 mL) solution of 100 g (469 mmol) of 4-t-butylphenylbromobenzene was added dropwise to the reaction mixture, followed by stirring at room temperature for one hour (synthesis of a Grignard compound).

Next, the reaction mixture thus obtained was cooled to 5° C. or less and a THF (200 mL) solution of 47.2 g (235 mmol) of (R)-Proline-N-ethyl carbamate methyl ester obtained in Synthesis Example 1 was added dropwise at 10° C. or less to cause a reaction therebetween. Then, the reaction mixture was heated under reflux for 3 hours and cooled. The reaction mixture was added in 500 mL of a saturated aqueous solution of ammonium chloride. Then, 500 mL of toluene for extraction was added, followed by stirring for one hour. The reaction mixture was transferred to a separatory funnel. The organic layer was separated. The aqueous layer was re-extracted twice with 500 mL of toluene. The organic layers were combined and washed twice with saturated saline. The organic layer was dried over anhydrous sodium sulfate and then distilled to remove the solvent. The crystals thus obtained were dissolved in 1.2 L of toluene by heating. After cooling, the crystals thus obtained were collected by filtration and dried under reduced pressure to obtain 65.8 g of (5R)-[3,3,0]-1-aza-2-oxo-3-oxa-4,4-bis-(4'-t-butylphenyl)-bicyclooctane.

In the (5R)-[3,3,0]-1-aza-2-oxo-3-oxa-4,4-bis-(4'-t-butylphenyl)-bicyclooctane thus obtained were added 460 mL of methanol, 460 mL of THF, and 2.63 g of 10 wt % Pd/C. The resulting mixture was stirred, followed by hydrogen purging. After reaction at room temperature for 10 days in the same atmosphere, the Pd/C was filtered off, the residue was concentrated, and the concentrate was purified by silica gel column chromatography to obtain 43.6 g of the intended product in the form of colorless crystals in a yield of 74.3%.

$^1$H-NMR (CD$_3$OD): δ=1.10 to 1.50, m, 19H δ=1.60 to 1.85, m, 3H δ=2.65 to 2.80, m, 1H δ=2.80 to 2.95, m, 1H δ=3.65, d, 1H δ=3.70 to 3.85, m, 1H δ=7.10 to 7.35, m, 8H

Synthesis Example 4

Synthesis of (S)-2-(bis-(4'-t-butylphenyl)methyl) pyrrolidine (Synthesis of the Optically Active Cyclic Nitrogen-Containing Compound in Example 7)

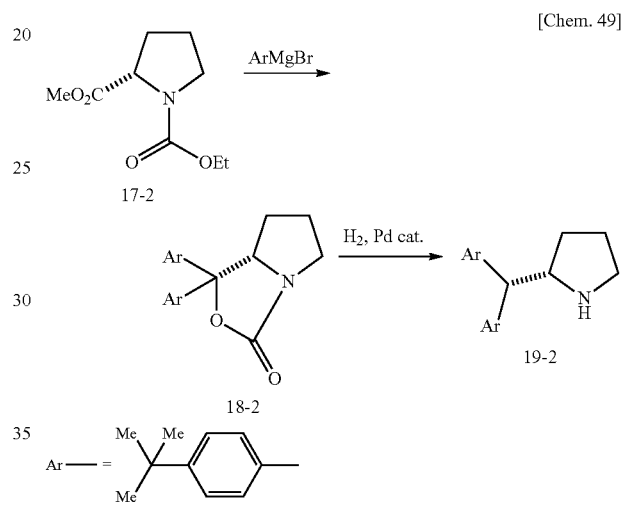

The synthesis was conducted according to the synthesis process of (S)-2-(diphenylmethyl)pyrrolidine described in Tetrahedron: Asymmetry, Vol. 8, No. 1, 149-153.

In a 300-mL reaction flask purged with nitrogen, were added 2.55 g (105 mmol) of magnesium and 50 mL of anhydrous THF in a nitrogen gas stream and the resulting mixture was stirred. A THF (30 mL) solution of 21.31 g (100 mmol) of 4-t-butylphenylbromobenzene was added dropwise to the reaction mixture at room temperature and the resulting mixture was stirred at room temperature for one hour (synthesis of a Grignard compound).

Next, the reaction mixture thus obtained was cooled to 5° C. or less and 10.05 g (50 mmol) of (S)-proline-N-ethyl carbamate methyl ester obtained in Synthesis Example 2 was added dropwise at 10° C. or less to cause a reaction therebetween. Then, the reaction mixture was heated under reflux for 3 hours and cooled. The reaction mixture was added in 100 mL of a saturated aqueous solution of ammonium chloride, 100 mL of toluene for extraction was added, and the resulting mixture was stirred for one hour. The reaction mixture was transferred to a separatory funnel and the organic layer was separated. The aqueous layer was re-extracted twice with 100 mL of toluene. The organic layers were combined and washed twice with saturated saline. After the organic layer was dried over anhydrous sodium sulfate, the solvent was distilled off. The crystals thus obtained were dissolved in 140 mL of ethyl acetate by heating. After cooling, the crystals thus obtained were collected by filtration and dried under reduced pressure to obtain 9.13 g of (5S)-[3,3,0]-1-aza-2-oxo-3-oxa-4,4-bis-(4'-t-butylphenyl)-bicyclooctane.

In the (5S)-[3,3,0]-1-aza-2-oxo-3-oxa-4,4-bis-(4'-t-butylphenyl)-bicyclooctane thus obtained were added 100 mL of methanol, 100 mL of THF, and 365 mg of 10 wt % Pd/C. The resulting mixture was stirred, followed by hydrogen purging. After reaction at room temperature for 4 days in the same atmosphere, the Pd/C was filtered off, the residue was concentrated, and the concentrate was purified by silica gel column chromatography to obtain 3.48 g of the intended product in the form of colorless crystals in a yield of 19.93%.

$^1$H-NMR (CD$_3$OD): δ=1.10 to 1.50, m, 19H δ=1.60 to 1.85, m, 3H δ=2.65 to 2.80, m, 1H δ=2.80 to 2.95, m, 1H δ=3.65, d, 1H δ=3.70 to 3.85, m, 1H δ=7.10 to 7.35, m, 8H

Synthesis Example 5

Synthesis of (S)-2-(bis-(4'-1-propylphenyl)methyl) pyrrolidine (Example 8 of Optically Active Cyclic Nitrogen-Containing Compound)

sulfate and then the solvent was distilled off to obtain 16.22 g of (5S)-[3,3,0]-1-aza-2-oxo-3-oxa-4,4-bis-(4'-1-propylphenyl)-bicyclooctane.

In the (5S)-[3,3,0]-1-aza-2-oxo-3-oxa-4,4-bis-(4'-1-propylphenyl)-bicyclooctane thus obtained were added 100 mL of methanol, 50 mL of THF, and 650 mg of 10 wt % Pd/C. The resulting mixture was stirred, followed by purging with hydrogen. The reaction was continued in the same atmosphere at room temperature for 4 days. Then, the Pd/C was filtered off, the residue was concentrated, and the concentrate was purified by silica gel column chromatography to obtain 2.71 g of the intended product in the form of colorless crystals in a yield of 16.86%.

$^1$H-NMR (CD$_3$OD): δ=1.05 to 1.20, m, 12H δ=1.20 to 1.35, m, 1H δ=1.60 to 1.80, m, 3H δ=2.65 to 2.95, m, 4H δ=3.60, d, 1H δ=3.70 to 3.85, m, 1H δ=7.00 to 7.30, m, 8H

Synthesis Example 6

Synthesis of (R)-2-(bis-(4'-(1''-methylcyclohexyl)phenyl)methyl)pyrrolidine (Synthesis of Optically Active Cyclic Nitrogen-Containing Compound of Example 9)

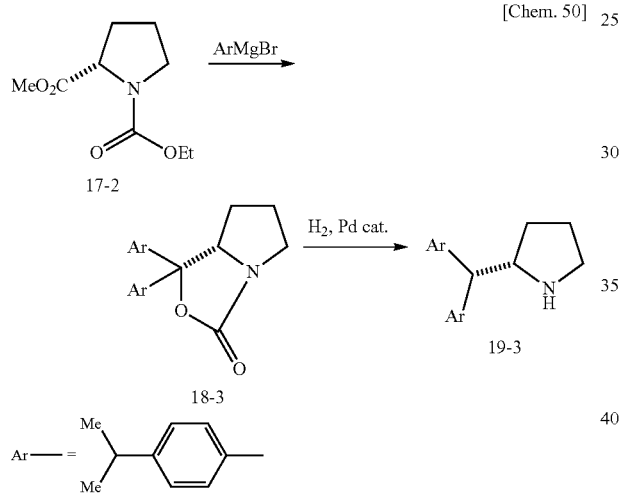

[Chem. 50]

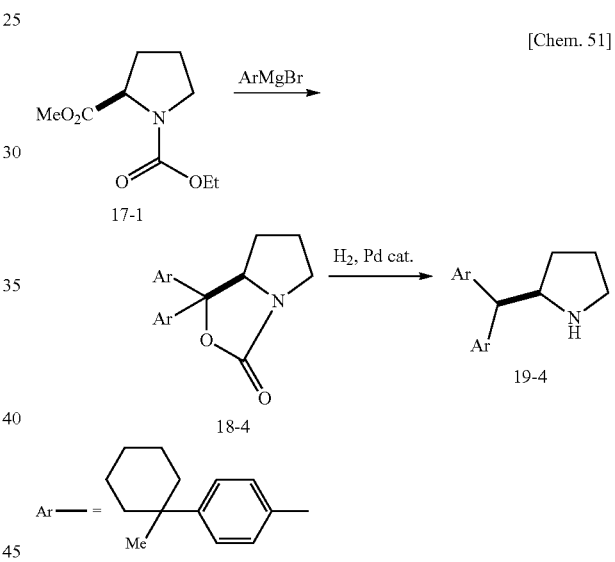

[Chem. 51]

The synthesis was conducted according to the synthesis process of (S)-2-(diphenylmethyl)pyrrolidine described in Tetrahedron: Asymmetry, Vol. 8, No. 1, 149-153.

In a 300-mL reaction flask purged with nitrogen were added 2.55 g (105 mmol) of magnesium and 50 mL of anhydrous THF in a nitrogen gas stream and the resulting mixture was stirred. To the reaction mixture was added dropwise a THF (300 ml) solution of 19.91 g (100 mmol) of 4-i-propylphenylbromobenzene at room temperature. The resulting mixture was stirred at room temperature for one hour (synthesis of a Grignard compound).

Next, the reaction mixture thus obtained in Synthesis Example 2 was cooled to 5° C. or less and 10.05 g (50 mmol) of the (S)-proline-N-ethyl carbamate methyl ester was added dropwise at 10° C. or less to cause a reaction therebetween. After heating under reflux for 3 hours, the reaction mixture was cooled. The reaction mixture was added in 100 mL of a saturated aqueous solution of ammonium chloride. Then, 100 mL of toluene for extraction was added and the mixture was stirred for one hour. The reaction mixture was transferred to a separatory funnel and the organic layer was separated. The organic layer thus obtained was washed twice with saturated saline. The organic layer was dried over anhydrous sodium

Synthesis Example 6-1

Synthesis of 1-methylcyclohexylbenzene

A mixed solution of 75.0 mL (632 mmol) of 1-methyl-1-cyclohexene and 56.4 mL (632 mmol) of benzene was added dropwise to 225.6 mL (2.53 mol) of a benzene solution of 231 g (2.36 mol) of sulfuric acid at 0° C. over 1.5 hours. The resulting mixture was stirred at 0° C. for 1.5 hours. The reaction mixture was quenched with 300 mL of water to separate the aqueous layer. The resulting organic layer thus obtained was washed with 100 mL of a saturated aqueous solution of sodium bicarbonate, 100 mL of water, and 100 mL of saturated saline and dried over anhydrous sodium sulfate. After the desiccant was filtered off, the filtrate was concentrated to obtain crude 1-methylcyclohexylbenzene. The resulting crude 1-methylcyclohexylbenzene was purified by distillation under reduced pressure (110 to 113° C./10 mmHg) to obtain 40.2 g of the intended product. Yield: 36.5%.

$^1$H-NMR (CDCl$_3$): δ=1.20, s, 3H δ=1.30 to 1.70, m, 8H δ=1.90 to 2.10, m, 2H δ=7.10 to 7.40, m, 5H

Synthesis Example 6-2

Synthesis of 4-(1'-methylcyclohexyl)bromobenzene

To 20.0 g (115 mmol) of the 1-methylcyclohexylbenzene obtained above (Synthesis Example 6-1) were added 279 mg (5.00 mmol) of iron and 198 mg (0.78 mmol) of iodine. At 0° C., 17.8 g (111 mmol) of bromine was slowly added dropwise over 1.5 hours to the resulting mixture. The reaction mixture was stirred for 1.5 hours at the temperature and for 20 hours at room temperature. The reaction mixture was cooled, quenched with 30 mL of a saturated aqueous solution of sodium sulfite, and then extracted three times with 50 mL of hexane. The combined organic layers were washed with 30 mL of an aqueous solution of sodium sulfide and 30 mL of water and then dried over anhydrous sodium sulfate. After the desiccant was filtered off, the solvent was collected under reduced pressure to obtain 27.9 g of crude bromide. The crude bromide thus obtained was purified by distillation under reduced pressure (117 to 120° C./2 mmHg) to obtain the intended product in a yield of 80.3%.

$^1$H-NMR (CDCl$_3$): δ=1.15, s, 3H δ=1.30 to 1.70, m, 8H δ=1.90 to 2.10, m, 2H 2H δ=7.15 to 7.50, m, 4H

Synthesis Example 6-3

Synthesis of (R)-2-(bis-(4'-(1''-methylcyclohexyl)phenyl)methyl)pyrrolidine

The synthesis was conducted according to the synthesis process of (S)-2-(diphenylmethyl)pyrrolidine described in Tetrahedron: Asymmetry, Vol. 8, No. 1, 149-153.

In a 100-mL reaction flask purged with nitrogen were added 535 mg (22.0 mmol) of magnesium and 4 mL of anhydrous THF in a nitrogen gas stream. The resulting mixture was stirred. A THF (25 mL) solution of 5.06 g (20 mmol) of the 4-(1'-methylcyclohexyl)bromobenzene obtained above (Synthesis Example 6-2) was added dropwise at room temperature and the resulting mixture was stirred at room temperature for 1 hour (synthesis of Grignard compound).

Next, the reaction mixture was cooled to 5° C. or less. To the reaction mixture was added dropwise a THF (16 mL) solution of 2.01 g (10 mmol) of the (R)-proline-N-ethyl carbamate methyl ester obtained in Synthesis Example 1 at 10° C. or less to cause a reaction therebetween. Then, after heating under reflux for 3 hours, the reaction mixture was cooled and added in 25 mL of a saturated aqueous solution of ammonium chloride. Then 50 mL of chloroform for extraction was added. The resulting mixture was stirred for one hour. The reaction mixture was transferred to a separatory funnel. The organic layer thus separated was washed twice with saturated saline. The organic layer was dried over anhydrous sodium sulfate and the solvent was distilled off to obtain 4.76 g of a concentrate. The concentrate was recrystallized from ethyl acetate to obtain 2.37 g of (5R)-[3,3,0]-1-aza-2-oxo-3-oxa-4,4-bis-(4'-(1''-methylcyclohexyl)phenyl)-bicyclooctane.

In the (5R)-[3,3,0]-1-aza-2-oxo-3-oxa-4,4-bis-(4'-(1''-methylcyclohexyl)phenyl)-bicyclooctane thus obtained were added 35 mL of methanol, 35 mL of THF, and 1.10 g of 10 wt % Pd/C. The resulting mixture was stirred, followed by purging with hydrogen. After reaction at 50° C. for 7.5 hours, the Pd/C was filtered off, the residue was concentrated, and the concentrate was purified by silica gel column chromatography to obtain 1.50 g of the intended product in the form of colorless crystals in a yield of 35.0%.

$^1$H-NMR (CDCl$_3$): δ=1.10 to 1.20, s, 6H δ=1.25 to 2.20, m, 24H δ=2.70 to 3.00, m, 2H δ=3.70 to 3.95, m, 2H δ=7.10 to 7.40, m, 8H

Synthesis Example 7

Synthesis of (R)-2-(bis-(p-1'-adamantylphenyl)methyl)pyrrolidine (Synthesis of Optically Active Cyclic Nitrogen-Containing Compound of Example 11)

[Chem. 52]

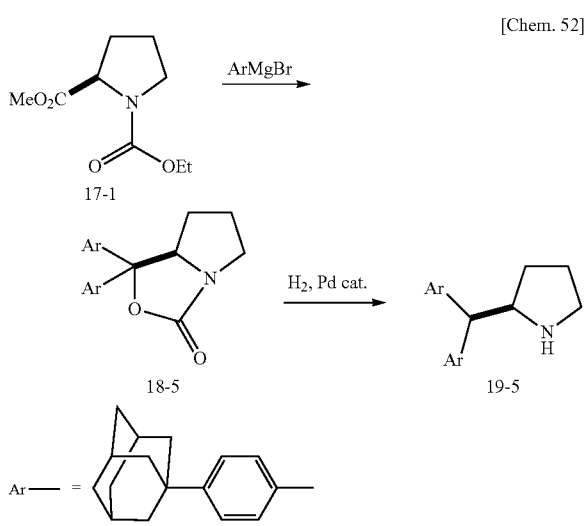

The synthesis was conducted according to the synthesis process of (S)-2-(diphenylmethyl)pyrrolidine described in Tetrahedron: Asymmetry, Vol. 8, No. 1, 149-153.

In a 200-mL reaction flask purged with nitrogen were added 0.591 g (24.3 mmol) of magnesium and 10 mL of anhydrous THF in a nitrogen gas stream, followed by stirring. To the reaction mixture was added dropwise a THF (30 mL) solution of 5.00 g (20.3 mmol) of p-1-adamantylphenylchlorobenzene and the resulting mixture was stirred at room temperature for one hour (synthesis of a Grignard compound).

Next, the resulting solution was cooled to 5° C. or less and 2.04 g (10.1 mmol) of the (R)-proline-N-ethyl carbamate methyl ester obtained in Synthesis Example 1 was added dropwise to the solution at 10° C. or less to cause a reaction therebetween. Then, after heating under reflux for 3 hours, the reaction mixture was cooled and added in 100 mL of a saturated aqueous solution of ammonium chloride. Then, 300 mL of THF for extraction was added. The resulting mixture was stirred for one hour. The reaction mixture was transferred to a separatory funnel and the organic layer thus separated was washed once with saturated saline. After the organic layer was dried over anhydrous sodium sulfate, the solvent was distilled off to obtain 2.37 g of (5R)-[3,3,0]-1-aza-2-oxo-3-oxa-4,4-bis-(p-1'-adamantylphenyl)-bicyclooctane.

In the resulting (5R)-[3,3,0]-1-aza-2-oxo-3-oxa-4,4-bis-(p-1'-adamantylphenyl)-bicyclooctane were added 36 mL of methanol, 36 mL of THF, and 1.18 g of 10 wt % Pd/C. The resulting mixture was stirred, followed by purging with hydrogen. After reaction at from 50 to 60° C. for 70 hours, the Pd/C was filtered off, the residue was concentrated, and the concentrate was purified by alumina column chromatography to obtain 1.45 g of the intended product in the form of colorless crystals in a yield of 31.6%.

$^1$H-NMR (CDCl$_3$): δ=1.40 to 2.20, m, 30H δ=2.60 to 2.80, br, 1H δ=3.05 to 3.90, m, 2H δ=4.10 to 4.90, m, 2H δ=7.00 to 7.50, m, 8H

Synthesis Example 8

Synthesis of (R)-2-(bis-(4'-(2"-p-tolylpropyl)phenyl)methyl)pyrrolidine (Synthesis of Optically Active Cyclic Nitrogen-Containing Compound of Example 12)

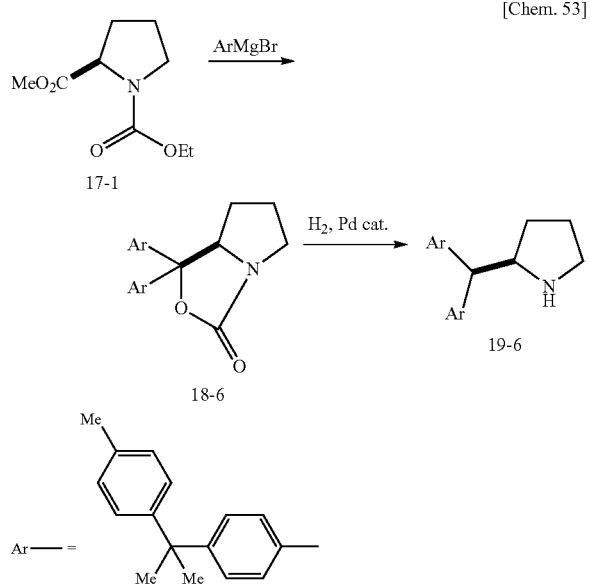

Synthesis Example 8-1

Synthesis of 4-(2'-p-tolylpropyl)chlorobenzene

A mixed solution of 21.5 mL (150 mmol) of p-chloromethylstyrene and 20 mL (280 mmol) of toluene was added dropwise to 59.9 mL (470 mmol) of a toluene solution of 44.1 g (450 mmol) of sulfuric acid over one hour and the resulting mixture was stirred at 0° C. for 2.0 hours. The reaction mixture was quenched with 100 mL of water, and the aqueous layer was separated. The organic layer thus obtained was washed with 50 mL of a saturated aqueous solution of sodium bicarbonate and 50 mL of water and dried over anhydrous sodium sulfate. The desiccant was filtered off and the filtrate was concentrated to obtain crude chloride. The crude chloride thus obtained was purified by distillation under reduced pressure (120 to 130° C./1 mmHg) to obtain 31.8 g of the intended product. Yield: 86.7%.

$^1$H-NMR (CDCl$_3$): δ=1.80, s, 6H δ=2.45, s, 3H δ=7.20 to 7.45, m, 8H

Synthesis Example 8-2

Synthesis of (R)-2-(bis-(4'-(2"-p-tolylpropyl)phenyl)methyl)pyrrolidine

The synthesis was conducted according to the synthesis process of (S)-2-(diphenylmethyl)pyrrolidine described in Tetrahedron: Asymmetry, Vol. 8, No. 1, 149-153.

In a 100-mL reaction flask purged with nitrogen were added 535 mg (22.0 mmol) of magnesium and 4 mL of anhydrous THF in a nitrogen gas stream, followed by stirring. To the reaction mixture was added dropwise a THF (20 mL) solution of 4.90 g (20 mmol) of the 4-(2'-p-tolylpropyl)chlorobenzene obtained above (Synthesis Example 8-1) slowly under reflux conditions at room temperature. The mixture was stirred for 6 hours under reflux conditions (synthesis of a Grignard compound).

Next, the reaction mixture was cooled to 5° C. or less and a THF (16 mL) solution of 2.01 g (10 mmol) of the (R)-proline-N-ethyl carbamate methyl ester obtained in Synthesis Example 1 was added dropwise at 10° C. or less to cause a reaction therebetween. After heating under reflux for 3 hours, the reaction mixture was cooled and added in 25 mL of a saturated aqueous solution of ammonium chloride. Then, 50 mL of chloroform for extraction was added and the resulting mixture was stirred for one hour. The reaction mixture was transferred to a separatory funnel. The organic layer thus separated was washed twice with saturated saline and dried over anhydrous sodium sulfate. The solvent was then distilled off to obtain a concentrate containing the intended product. The concentrate was recrystallized from a hexane/ethyl acetate mixed solvent to obtain 2.90 g of (5R)-[3,3,0]-1-aza-2-oxo-3-oxa-4,4-bis-(4'-(2"-p-tolylpropyl)phenyl)-bicyclooctane.

In the (5R)-[3,3,0]-1-aza-2-oxo-3-oxa-4,4-bis-(4'-(2"-p-tolylpropyl)phenyl)-bicyclooctane thus obtained were added 29 mL of methanol, 29 mL of THF, and 1.45 g of 10 wt % Pd/C. The resulting mixture was stirred, followed by purging with hydrogen. After reaction at 50° C. for 15 hours, the Pd/C was filtered off, the residue was concentrated, and the concentrate was purified by silica gel column chromatography to obtain 1.86 g of the intended product in the form of colorless crystals in a yield of 24.7%.

$^1$H-NMR (CDCl$_3$): δ=1.30 to 2.00, m, 4H δ=1.60, s, 12H δ=2.30, s, 6H δ=2.70 to 3.00, m, 2H δ=3.75 to 3.90, m, 2H δ=7.00 to 7.30, m, 16H

Synthesis Example 9

Synthesis of (S)-2-(bis-(4'-trifloromethylphenyl)methyl)pyrrolidine (Synthesis of Optically Active Cyclic Nitrogen Compound of Example 13)

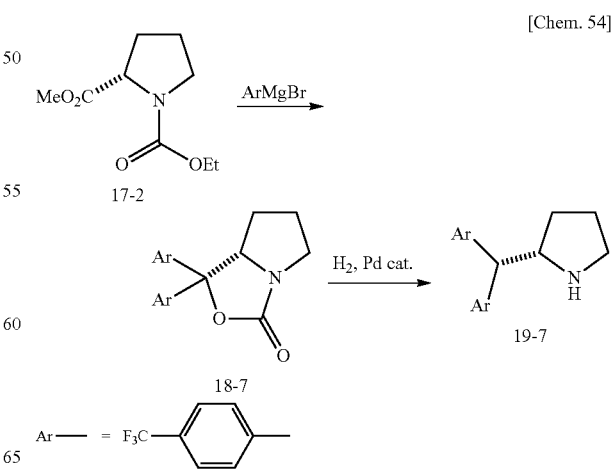

The synthesis was conducted according to the synthesis process of (S)-2-(diphenylmethyl)pyrrolidine described in Tetrahedron: Asymmetry, Vol. 8, No. 1, 149-153.

In a 300-mL reaction flask purged with nitrogen were added 2.55 g (105 mmol) of magnesium and 50 mL of anhydrous THF under a nitrogen gas stream, followed by stirring. A THF (30 mL) solution of 22.5 g (100 mmol) of 4-trifluoromethylphenylbromobenzene was added dropwise to the reaction mixture at room temperature and the resulting mixture was stirred for one hour at room temperature (synthesis of a Grignard compound).

Next, the reaction mixture was cooled to 5° C. or less. To the reaction mixture was added dropwise 10.05 g (50 mmol) of the (S)-proline-N-ethyl carbamate methyl ester obtained in Synthesis Example 2 at 10° C. or less to cause a reaction therebetween. After heating under reflux for 3 hours, the reaction mixture was cooled and then, added in 100 mL of a saturated aqueous solution of ammonium chloride. Then, 100 mL of toluene for extraction was added and the resulting mixture was stirred for one hour. The reaction mixture was transferred to a separatory funnel. The organic layer thus separated was washed twice with saturated saline. After the organic layer was dried over anhydrous sodium sulfate, the solvent was distilled off to obtain 12.87 g of (5S)-[3,3,0]-1-aza-2-oxo-3-oxa-4,4-bis-(4'-trifloromethylphenyl)-bicyclooctane.

In the (5S)-[3,3,0]-1-aza-2-oxo-3-oxa-4,4-bis-(4'-trifloromethylphenyl)-bicyclooctane thus obtained were added 130 mL of methanol and 514 mg of 10 wt % Pd/C. The resulting mixture was stirred, followed by purging with hydrogen. After the reaction was continued in the same atmosphere at room temperature for 4 days, the Pd/C was filtered off, the residue was concentrated, and the concentrate was purified by silica gel column chromatography to obtain 6.74 g of the intended product in the form of a light yellow oil in a yield of 36.11%.

$^1$H-NMR (CD$_3$OD): δ=1.25 to 1.50, m, 1H δ=1.70 to 1.95, m, 3H δ=2.80 to 2.90, m, 1H δ=2.90 to 3.05, m, 1H δ=3.90 to 4.05, m, 1H δ=7.45 to 7.65, m, 8H

Synthesis Example 10

Synthesis of (S)-2-(bis-(p-biphenyl)methyl)pyrrolidine (Synthesis of Optically Active Cyclic Nitrogen-Containing Compound of Example 14)

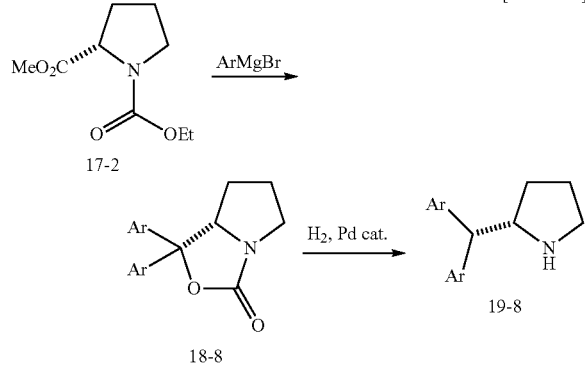

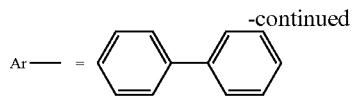

The synthesis was conducted according to the synthesis process of (S)-2-(diphenylmethyl)pyrrolidine described in Tetrahedron: Asymmetry, Vol. 8, No. 1, 149-153.

In a 300-mL reaction flask purged with nitrogen were added 2.13 g (87.5 mmol) of magnesium and 10 mL of anhydrous THF under a nitrogen gas stream, followed by stirring. A THF (54 mL) solution of 19.1 g (81.9 mmol) of p-bromobiphenyl was added dropwise to the reaction mixture at room temperature and the resulting mixture was stirred for one hour at room temperature (synthesis of a Grignard compound).

Next, the reaction mixture was cooled to 5° C. or less and 8.00 g (39.8 mmol) of (S)-proline-N-ethyl carbamate methyl ester obtained in Synthesis Example 2 was added dropwise to the reaction mixture at 10° C. or less to cause a reaction therebetween. After heating under reflux for 3 hours, the reaction mixture was cooled and then added in 100 mL of a saturated aqueous solution of ammonium chloride. Then, 100 mL of toluene for extraction was added. The resulting mixture was stirred for one hour. The reaction mixture was transferred to a separatory funnel and the organic layer thus separated was washed twice with saturated saline. After the organic layer was dried over anhydrous sodium sulfate, the solvent was distilled off to obtain 6.71 g of (5S)-[3,3,0]-1-aza-2-oxo-3-oxa-4,4-bis-(p-biphenyl)-bicyclooctane.

In the (5S)-[3,3,0]-1-aza-2-oxo-3-oxa-4,4-bis-(p-biphenyl)-bicyclooctane thus obtained were added 130 mL of methanol and 335 mg of 10 wt % Pd/C. The resulting mixture was stirred, followed by purging with hydrogen. After the reaction was continued in the same atmosphere at room temperature for 4 days, the Pd/C was filtered off, the residue was concentrated, and the concentrate was purified by silica gel column chromatography to obtain 1.52 g of the intended product in the form of colorless crystals in a yield of 25.1%.

$^1$H-NMR (CDCl$_3$): δ=1.43 to 1.89, m, 5H δ=2.86 to 3.12, m, 2H δ=3.85 to 3.89, m, 2H δ=7.25 to 7.56, m, 18H

Synthesis Example 11

Synthesis of (2R,4R)-4-hydroxyproline-N-ethyl carbamate methyl ester

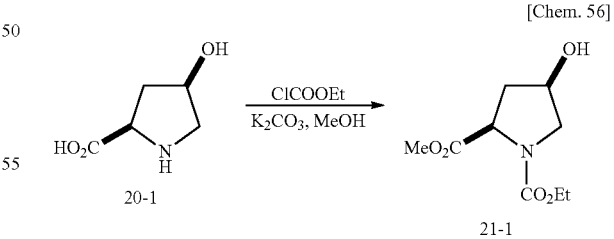

The synthesis was conducted according to the synthesis process described in Tetrahedron, Vol. 49, No. 23, 5127-5132.

In a 300-mL four-necked flask were added 25.0 g (191 mmol) of (2R,4R)-hydroxyproline (product of Watanabe Chemical Industries), 150 mL of anhydrous methanol, and 26.4 g (191 mmol) of potassium carbonate, followed by stirring. Under ice cooling, 40.2 mL (420 mmol) of ethyl chlorocarbonate was added dropwise to the reaction mixture at 25° C. or less and the resulting mixture was stirred at 0° C. for 24 hours. After filtration of the reaction mixture, the methanol was distilled off and 150 mL of water was added in the residue. The mixture was extracted with 150 mL of chloroform. Then, the aqueous layer was extracted twice with 150 mL of chloroform.

The organic layer thus obtained was washed with saturated saline, dried over anhydrous magnesium sulfate and filtered. The solvent was then distilled off to obtain 36.5 g of the intended product in a yield of 94.0%.

Synthesis Example 12

Synthesis of (5R,7R)-[3,3,0]-1-aza-2-oxo-3-oxa-4,4-bis-(4'-t-butylphenyl)-7-hydroxybicyclooctane

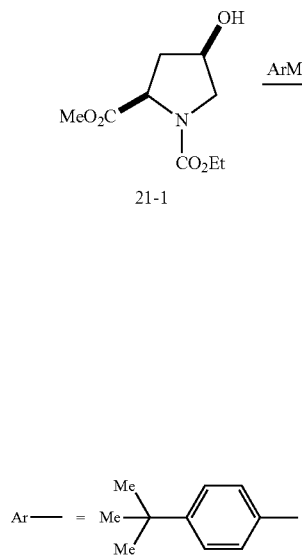

The synthesis was conducted according to the synthesis process of (S)-2-(diphenylmethyl)pyrrolidine described in Tetrahedron: Asymmetry, Vol. 8, No. 1, 149-153.

In a 500-mL reaction flask purged with nitrogen were added 2.41 g (99 mmol) of magnesium and 15 mL of anhydrous THF in a nitrogen gas stream, followed by stirring. To the reaction mixture was added dropwise a THF (75 mL) solution of 19.2 g (90 mmol) of 4-t-butylphenylbromobenzene at room temperature. The mixture was stirred for 1 hour at room temperature (synthesis of a Grignard compound).

Next, the reaction mixture was cooled to 5° C. or less and a THF (125 mL) solution of 6.10 g (30 mmol) of the (2R,4R)-4-hydroxyproline-N-ethyl carbamate methyl ester obtained in Synthesis Example 11 was added dropwise at 10° C. or less to cause a reaction therebetween. After heating under reflux for 3 hours, the reaction mixture was cooled and added in 100 mL of a saturated aqueous solution of ammonium chloride. After collection of the THF, the concentrate was extracted twice with 200 mL of ethyl acetate. The combined organic layers were washed twice with saturated saline and dried over anhydrous sodium sulfate. The solvent was then distilled off.

The concentrate thus obtained was recrystallized from ethyl acetate•hexane to obtain 8.24 g of the intended product.

Synthesis Example 13

Synthesis of (5R,7R)-[3,3,0]-1-aza-2-oxo-3-oxa-4,4-bis-(4'-t-butylphenyl)-7-(butylcarbamoyloxy)bicyclooctane

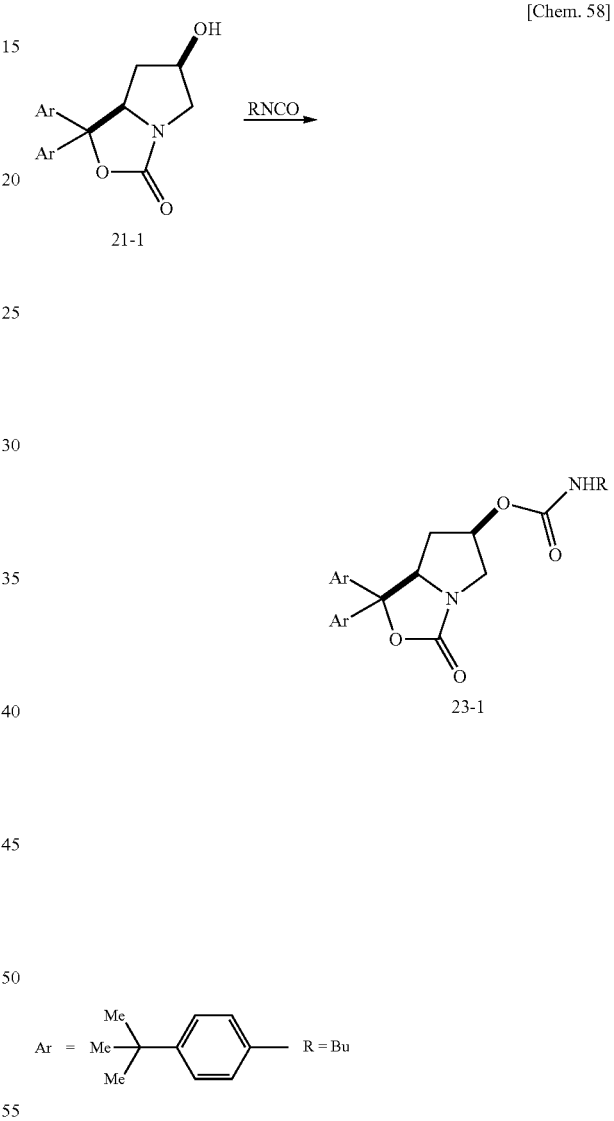

In a 50-mL four-necked flask were added 900 mg (2.21 mmol) of the (5R,7R)-[3,3,0]-1-aza-2-oxo-3-oxa-4,4-bis-(4'-t-butylphenyl)-7-hydroxybicyclooctane obtained in Synthesis Example 2, 9 mL of anhydrous DMF, and 110 mg (1.11 mmol) of copper (I) chloride, followed by stirring. To the reaction mixture was added dropwise 0.37 mL (3.32 mmol) of n-butyl isocyanate at room temperature and the resulting mixture was stirred at room temperature for 4 hours. The reaction mixture was extracted with water and toluene and the combined organic layers were washed with water and saturated saline. After the solvent was distilled off, the residue was purified by silica gel column chromatography to obtain 1.10 g of the intended product in the form of a colorless oil in a yield of 98.2%.

Synthesis Example 14

Synthesis of (2R,4R)-2-(bis-(4'-t-butylphenyl)methyl)-4-(butylcarbamoyloxy)pyrrolidine (synthesis of optically active cyclic nitrogen-containing compound used in examples 15, 20, and 26)

$^1$H-NMR (CD$_3$OD): δ=0.80 to 0.95, t, 3H δ=1.20 to 1.30, s, 18H δ=1.15 to 1.55, m, 6H δ=2.05 to 2.20, m, 1H δ=2.90 to 3.10, m, 4H δ=3.70 to 3.95, m, 2H δ=4.90 to 5.05, bs, 1H δ=7.10 to 7.35, m, 8H

Synthesis Example 15

Synthesis of (5R,7R)-[3,3,0]-1-aza-2-oxo-3-oxa-4,4-bis-(4'-t-butylphenyl)-7-(t-butylcarbamoyloxy)bicyclooctane

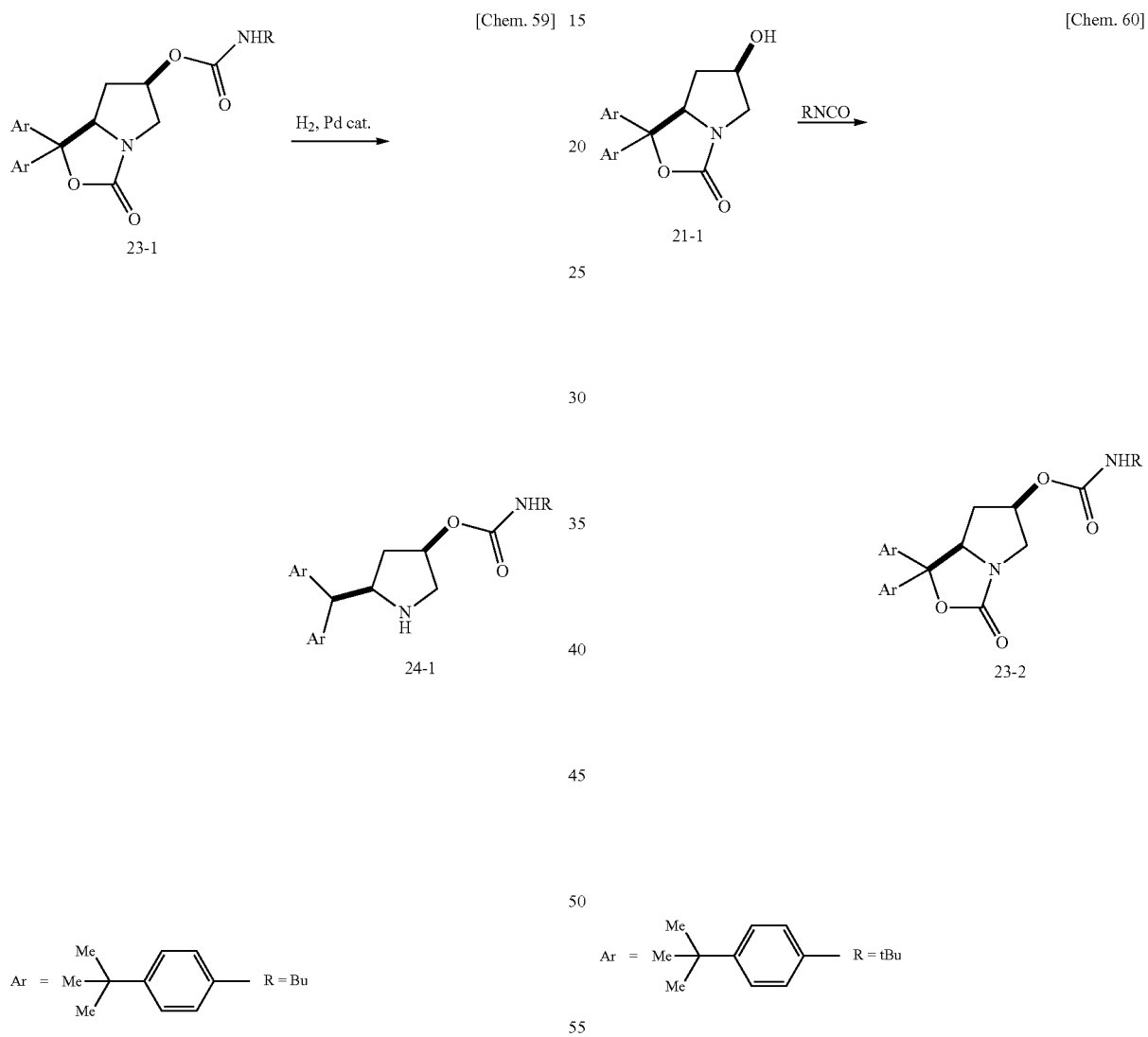

In 1.08 g (2.13 mmol) of the (5R,7R)-[3,3,0]-1-aza-2-oxo-3-oxa-4,4-bis-(4'-t-butylphenyl)-7-(butylcarbamoyloxy)bicyclooctane obtained in Synthesis Example 13 were added 10.8 mL of methanol, 10.8 mL of THF, and 135 mg of 10 wt % Pd/C. The resulting mixture was stirred, followed by purging with hydrogen. After reaction at room temperature for 3 days under a hydrogen atmosphere, the Pd/C was filtered off, the residue was concentrated, and the concentrate was purified by silica gel column chromatography to obtain 720 mg of the intended product in the form of a colorless oil in a yield of 72.7%.

In a 50-mL four-necked flask were added 900 mg (2.21 mmol) of the (5R,7R)-[3,3,0]-1-aza-2-oxo-3-oxa-4,4-bis-(4'-t-butylphenyl)-7-hydroxybicyclooctane obtained in Synthesis Example 12, 9 mL of anhydrous DMF, and 110 mg (1.11 mmol) of copper (I) chloride, followed by stirring. To the resulting reaction mixture was added dropwise 0.39 mL (3.32 mmol) of t-butyl isocyanate at room temperature and the resulting mixture was then stirred at room temperature for 4 hours. The reaction mixture was then extracted with water and toluene. The combined organic layers were washed with water and unsaturated saline. After the solvent was distilled off, the residue was purified by silica gel column chromatography to obtain 1.09 g of the intended product in the form of a colorless oil in a yield of 97.3%.

Synthesis Example 16

Synthesis of (2R,4R)-2-(bis-(4'-t-butylphenyl)methyl)-4-(t-butylcarbamoyloxy)pyrrolidine (synthesis of optically active cyclic nitrogen-containing compound used in examples 21 and 27)

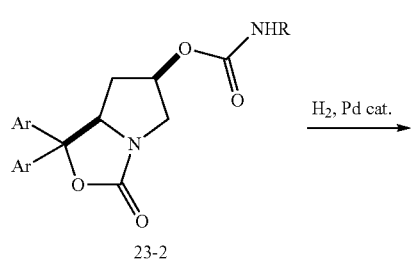

23-2

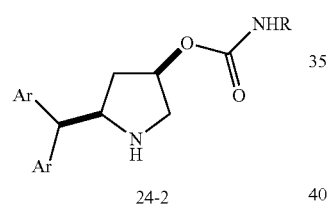

24-2

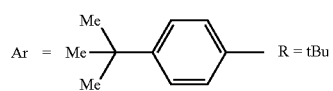

In 1.08 g (2.13 mmol) of the (5R,7R)-[3,3,0]-1-aza-2-oxo-3-oxa-4,4-bis-(4'-t-butylphenyl)-7-(t-butylcarbamoyloxy) bicyclooctane obtained in Synthesis Example 15 were added 10.8 mL of methanol, 10.8 mL of THF, and 135 mg of 10 wt % Pd/C. The resulting mixture was stirred, followed by purging with hydrogen. After reaction at room temperature for 3 days under a hydrogen atmosphere, the Pd/C was filtered off, the residue was concentrated, and the concentrate was purified by silica gel column chromatography to obtain 690 mg of the intended product in the form of a colorless oil in a yield of 60.1%.

$^1$H-NMR (CD$_3$Cl$_3$): δ=1.20, s, 9H δ=1.22, s, 9H δ=1.25, s, 9H δ=1.20 to 1.30, m, 1H δ=1.50 to 1.65, m, 1H δ=2.10 to 2.30, m, 1H δ=2.90 to 3.00, m, 2H δ=3.70 to 3.40, m, 2H δ=5.00 to 5.20, bs, 1H S=7.10 to 7.40, m, 8H

Synthesis Example 17

Synthesis of (5R,7R)-[3,3,0]-1-aza-2-oxo-3-oxa-4,4-bis-(4'-t-butylphenyl)-7-(ethylcarbamoyloxy)bicyclooctane

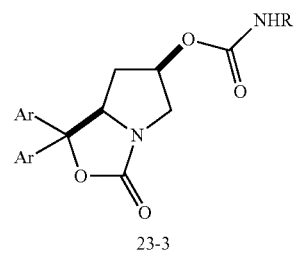

22-1

23-3

Ar = Me—C(Me)(Me)—C$_6$H$_4$— R = Et

In a 50-mL four-necked flask were added 900 mg (2.21 mmol) of the (5R,7R)-[3,3,0]-1-aza-2-oxo-3-oxa-4,4-bis-(4'-t-butylphenyl)-7-hydroxybicyclooctane obtained in Synthesis Example 12, 9 mL of anhydrous DMF, and 110 mg (1.11 mmol) of copper (I) chloride, followed by stirring. To the reaction mixture was added dropwise 0.26 mL (3.32 mmol) of ethyl isocyanate at room temperature and the resulting mixture was stirred at room temperature for 4 hours. The reaction mixture was extracted with water and toluene. The combined organic layers were washed with water and saturated saline. After the solvent was distilled off, the residue was purified by silica gel column chromatography to obtain 680 mg of the intended product in the form of a colorless oil in a yield of 64.3%.

Synthesis Example 18

Synthesis of (2R,4R)-2-(bis-(4'-t-butylphenyl)methyl)-4-(ethylcarbamoyloxy)pyrrolidine (synthesis of the optically active cyclic nitrogen-containing compound to be used in examples 16 and 22)

[Chem. 63]

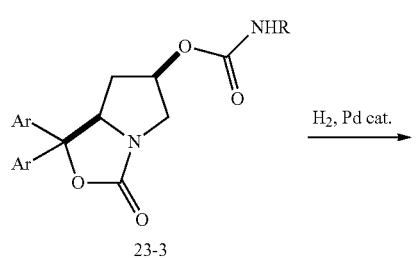

23-3

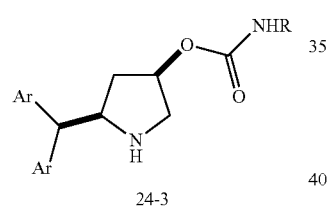

24-3

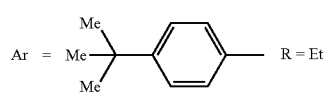

In 1.08 g (2.13 mmol) of the (5R,7R)-[3,3,0]-1-aza-2-oxo-3-oxa-4,4-bis-(4'-t-butylphenyl)-7-(ethylcarbamoyloxy)bicyclooctane obtained in Synthesis Example 17 were added 10.8 mL of methanol, 10.8 mL of THF, and 135 mg of 10 wt % Pd/C. The resulting mixture was stirred, followed by purging with hydrogen. After reaction at room temperature for 3 days in a hydrogen atmosphere, the Pd/C was filtered off, the residue was concentrated, and the concentrate was purified by silica gel column chromatography to obtain 480 mg of the intended product in the form of a colorless oil in a yield of 80.8%.

$^1$H-NMR (CD$_3$Cl$_3$): δ=1.05 to 1.20, t, 3H δ=1.25, s, 18H δ=1.30 to 1.60, m, 2H δ=2.15 to 2.30, m, 1H δ=2.95 to 3.25, m, 4H δ=3.80, bs, 2H δ=4.60, bs, 1H δ=5.10, bs, 1H δ=7.10 to 7.30, m, 8H

Synthesis Example 19

Synthesis of (5R,7R)-[3,3,0]-1-aza-2-oxo-3-oxa-4,4-bis-(4'-t-butylphenyl)-7-(octylcarbamoyloxy)bicyclooctane

[Chem. 64]

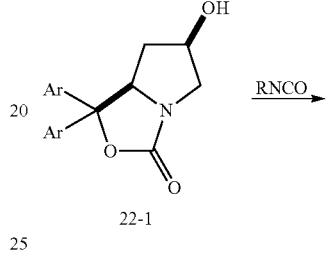

22-1

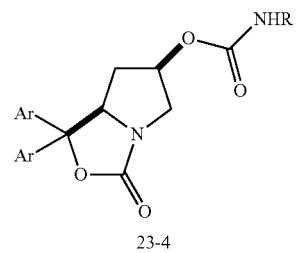

23-4

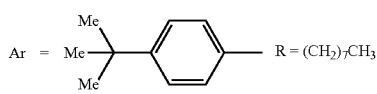

In a 50-L four-necked flask were added 900 mg (2.21 mmol) of the (5R,7R)-[3,3,0]-1-aza-2-oxo-3-oxa-4,4-bis-(4'-t-butylphenyl)-7-hydroxybicyclooctane obtained in Synthesis Example 12, 9 mL of anhydrous DMF, and 110 mg (1.11 mmol) of copper (I) chloride, followed by stirring. To the reaction mixture was added dropwise 0.59 mL (3.32 mmol) of octyl isocyanate at room temperature. The resulting mixture was stirred at room temperature for 4 hours. The reaction mixture was extracted with water and toluene. The combined organic layers were washed with water and saturated saline. After the solvent was distilled off, the residue was purified by silica gel column chromatography to obtain 1.08 g of the intended product in the form of a colorless oil in a yield of 86.8%.

Synthesis Example 20

Synthesis of (2R,4R)-2-(bis-(4'-t-butylphenyl)methyl)-4-(octylcarbamoyloxy)pyrrolidine (synthesis of optically active cyclic nitrogen-containing compound used in examples 17 and 23)

[Chem. 65]

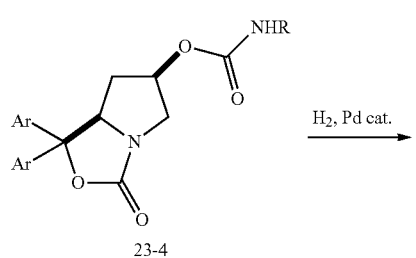

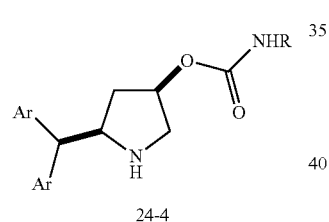

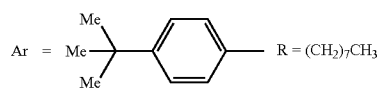

In 1.08 g (2.13 mmol) of the (5R,7R)-[3,3,0]-1-aza-2-oxo-3-oxa-4,4-bis-(4'-t-butylphenyl)-7-(octylcarbamoyloxy)bicyclooctane obtained in Synthesis Example 19 were added 10.8 mL of methanol, 10.8 mL of THF, and 135 mg of 10 wt % Pd/C. The resulting mixture was stirred, followed by purging with hydrogen. After reaction at room temperature for 3 days in a hydrogen atmosphere, the Pd/C was filtered off and the residue was concentrated. The concentrate was purified by silica gel column chromatography to obtain 540 mg of the intended product in the form of a colorless oil in a yield of 58.3%.

$^1$H-NMR (CD$_3$OD): δ=0.80 to 0.95, t, 3H δ=1.00 to 1.60, m, 14H δ=1.10, s, 18H δ=2.00 to 2.20, m, 1H δ=2.90 to 3.20, m, 4H δ=3.70 to 4.00, m, 2H δ=5.00 to 5.10, bs, 1H δ=7.10 to 7.40, m, 8H

Synthesis Example 21

Synthesis of (5R,7R)-[3,3,0]-1-aza-2-oxo-3-oxa-4,4-bis-(4'-t-butylphenyl)-7-(diphenylcarbamoyloxy)bicyclooctane

[Chem. 66]

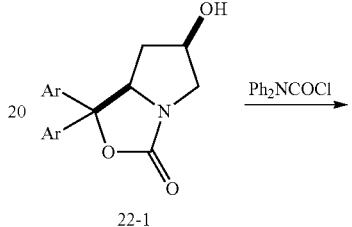

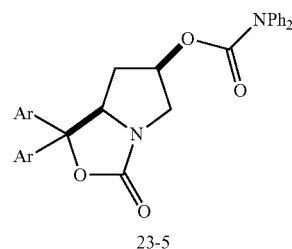

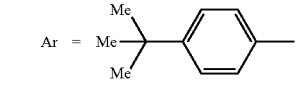

In a 50-mL four-necked flask were added 1.00 g (2.45 mmol) of the (5R,7R)-[3,3,0]-1-aza-2-oxo-3-oxa-4,4-bis-(4'-t-butylphenyl)-7-hydroxybicyclooctane obtained in Synthesis Example 12, 10 mL of anhydrous DMF, and 118 mg (4.90 mmol) of sodium hydride, followed by stirring. In the reaction mixture was added 626 mg (2.70 mmol) of diphenylcarbamoyl chloride under ice cooling and the resulting mixture was stirred at room temperature for 2 hours. The reaction mixture was extracted with water and toluene. The combined organic layers were washed with water and saline. After the solvent was distilled off, the residue was purified by silica gel column chromatography to obtain 920 mg of the intended product in the form of a colorless oil in a yield of 62.3%.

Synthesis example 22

Synthesis of (2R,4R)-2-(bis-(4'-t-butylphenyl)methyl)-4-(diphenylcarbamoyloxy)pyrrolidine (synthesis of optically active cyclic nitrogen-containing compound used in examples 18 and 24)

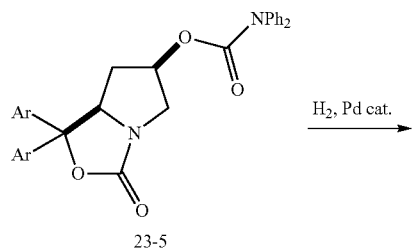

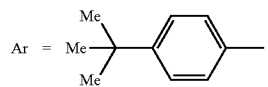

In 920 mg (1.53 mmol) of the (5R,7R)-[3,3,0]-1-aza-2-oxo-3-oxa-4,4-bis-(4'-t-butylphenyl)-7-(diphenylcarbamoyloxy)bicyclooctane obtained in Synthesis Example 21 were added 18.4 mL of methanol, 18.4 mL of THF, and 115 mg of 10 wt % Pd/C. The resulting mixture was stirred, followed by purging with hydrogen. After reaction at room temperature for 5 days in a hydrogen atmosphere, the Pd/C was filtered off and the residue was concentrated. The concentrate was purified by silica gel column chromatography to obtain 680 mg of the intended product in the form of a colorless oil in a yield of 79.3%.

$^1$H-NMR (CD$_3$OD): δ=1.20 to 1.35, s, 18H δ=1.45 to 1.60, m, 1H δ=2.00 to 2.20, m, 1H δ=2.90 to 3.00, m, 1H δ=3.10 to 3.20, m, 1H δ=3.35 to 3.45, m, 1H δ=3.85 to 4.00, m, 1H δ=5.15 to 5.25, m, 1H δ=6.90 to 7.50, m, 18H

Synthesis Example 23

Synthesis of (5R,7R)-[3,3,0]-1-aza-2-oxo-3-oxa-4,4-diphenyl-7-hydroxybicyclooctane

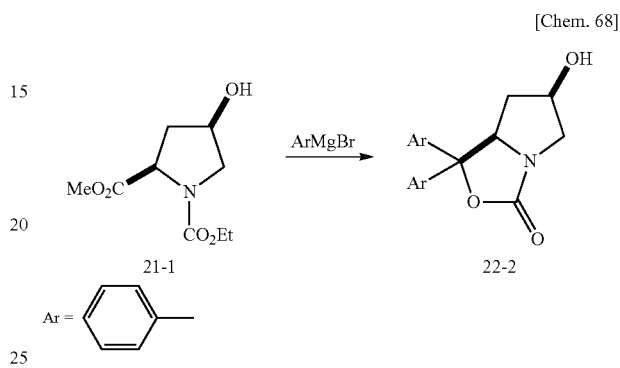

The synthesis was conducted according to the synthesis process of (S)-2-(diphenylmethyl)pyrrolidine described in Tetrahedron: Asymmetry, Vol. 8, No. 1, 149-153.

In a 500-mL reaction flask purged with nitrogen was added a THF (50 mL) solution of 5.10 g (23 mmol) of the (2R,4R)-4-hydroxyproline-N-ethyl carbamate methyl ester obtained in Synthesis Example 11 under a nitrogen gas stream, followed by cooling to 10° C. or less. To the solution was added dropwise 64 mL of a 1.08 mol/L THF solution of phenylmagnesium bromide from a dropping funnel to cause a reaction therebetween. After heating under reflux for 3 hours, the reaction mixture was cooled and added in 100 mL of a saturated aqueous solution of ammonium chloride. The THF was collected and the concentrate was extracted twice with 200 mL of ethyl acetate. The combined organic layers were washed twice with saturated saline and dried over anhydrous magnesium sulfate. Then, the solvent was distilled off. The concentrate thus obtained was isolated and purified by silica gel column chromatography to obtain 3.43 g of the intended product.

Synthesis example 24

Synthesis of (5R,7R)-[3,3,0]-1-aza-2-oxo-3-oxa-4,4-diphenyl-7-(butylcarbamoyloxy)bicyclooctane

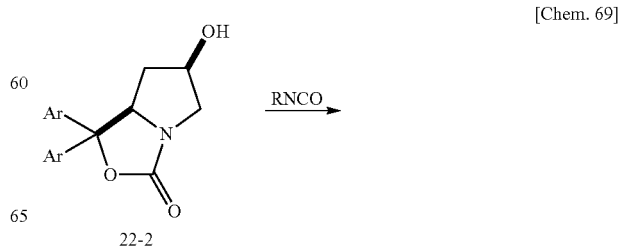

-continued

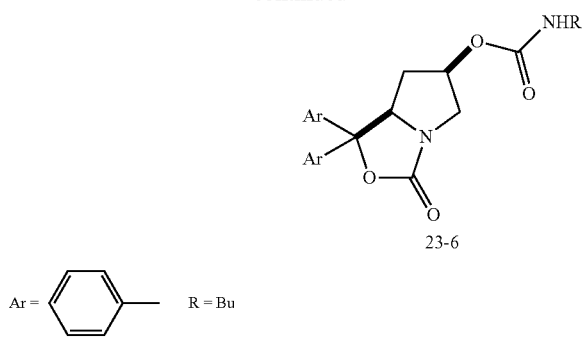

23-6

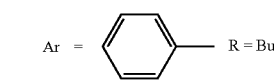

In a 100-mL four-necked flask were added 3.43 g (11.6 mmol) of the (5R,7R)-[3,3,0]-1-aza-2-oxo-3-oxa-4,4-bis-diphenyl-7-hydroxybicyclooctane obtained in Synthesis Example 23, 17 mL of anhydrous DMF, and 115 mg (1.16 mmol) of copper (I) chloride. The resulting mixture was stirred. To the reaction mixture was added dropwise 1.55 mL (1.39 mmol) of n-butyl isocyanate at room temperature, followed by stirring at room temperature for 4 hours. The reaction mixture was extracted with water and toluene. The combined organic layers were washed with water and saturated saline. After the solvent was distilled off, the residue was purified by silica gel column chromatography to obtain 1.91 g of the intended product in the form of a colorless oil in a yield of 41.9%.

Synthesis Example 25

Synthesis of (2R,4R)-2-diphenylmethyl-4-(butylcarbamoyloxy)pyrrolidine (synthesis of optically active cyclic nitrogen-containing compound used in examples 19 and 25)

[Chem. 70]

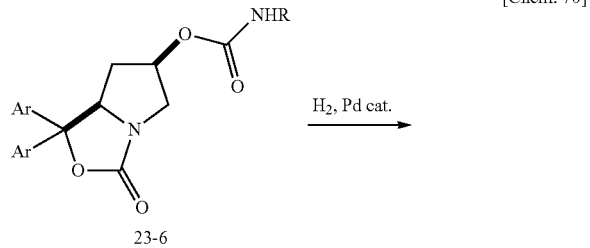

In 1.91 g (4.87 mmol) of the (5R,7R)-[3,3,0]-1-aza-2-oxo-3-oxa-4,4-diphenyl-7-(butylcarbamoyloxy)bicyclooctane obtained in Synthesis Example 24 were added 19 mL of methanol and 95.6 mg of 10 wt % Pd/C. The resulting mixture was stirred, followed by purging with hydrogen. After reaction at 40° C. for three days in a hydrogen atmosphere, the Pd/C was filtered off, the residue was concentrated, and the concentrate was purified by silica gel column chromatography to obtain 690 mg of the intended product in the form of a colorless oil in a yield of 40.3%.

$^1$H-NMR (CD$_3$OD): δ=0.90 to 0.96, t, 3H δ=1.30 to 1.59, m, 5H δ=2.10 to 2.21, qui, 1H δ=3.00 to 3.11, m, 4H δ=3.86 to 4.05, m, 2H δ=5.00 to 5.05, m, 1H δ=7.14 to 7.41, m, 10H

Example 1

In a 10-mL reaction flask were added 2 g (13.14 mmol) of citral, 25 mg (1.25 wt % based on the citral) of 5 wt % Pd/barium sulfate, 80 mg of (0.23 mmol; 4.0 wt. % based on the citral) of (R)-2-(bis-(4'-t-butylphenyl)methyl)pyrrolidine, 26.1 mg (0.23 mmol) of trifluoroacetic acid, and 4 mL of 10 wt % hydrous t-BuOH. The resulting mixture was stirred and the atmosphere was changed to a hydrogen atmosphere (0.1 MPa (atmospheric pressure)). After stirring at 40° C. for 21 hours, the catalyst was filtered off. As a result of analyzing the residue by using gas chromatography, it was found that a conversion ratio from citral to citronellal was 51%, the citronellal thus obtained was a d-form, and it had an optical purity of 84.9% e.e.

The citral used had a mixing ratio of geranial:neral=50:50 (molar ratio) (which will equally apply to Examples described below).

Examples 2 to 14

In each of these examples, a reaction was conducted under similar conditions to Example 1 except that the reaction was conducted at 25° C. in Example 2, the reaction was conducted at 50° C. in Example 3, the reaction was conducted at 60° C. in Example 4, and the reaction was conducted in toluene at 25° C. in Example 14, while changing the optically active cyclic nitrogen-containing compound and the acid. It is to be noted that in the reaction, the optically active cyclic nitrogen-containing compound was used in an amount of 80 mg and the acid was used in an equimolar amount to the optically active cyclic nitrogen-containing compound. The results are shown in Tables 3 to 6.

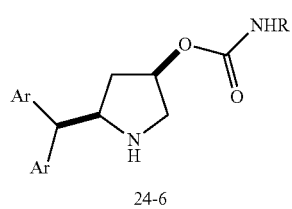

24-6

TABLE 3

| Ex. | Optically active cyclic nitrogen-containing compound | Acid | Conversion (%) | Steric configuration of citronellal | Optical purity (% e.e.) |
|---|---|---|---|---|---|
| 1 | (4-tBu-C6H4)(4-tBu-C6H4)CH-pyrrolidine | TFA | 51.36 | d | 84.9 |
| 2 | (4-tBu-C6H4)(4-tBu-C6H4)CH-pyrrolidine | TFA | 25.90 | d | 73.0 |
| 3 | (4-tBu-C6H4)(4-tBu-C6H4)CH-pyrrolidine | TFA | 98.66 | d | 80.4 |
| 4 | (4-tBu-C6H4)(4-tBu-C6H4)CH-pyrrolidine | TFA | 99.71 | d | 83.8 |

TABLE 4

| Ex. | Optically active cyclic nitrogen-containing compound | Acid | Conversion (%) | Steric configuration of citronellal | Optical purity (% e.e.) |
|---|---|---|---|---|---|
| 5 | (4-tBu-C6H4)(4-tBu-C6H4)CH-pyrrolidine | L-mandelic acid | 100 | d | 69.3 |
| 6 | (4-tBu-C6H4)(4-tBu-C6H4)CH-pyrrolidine | D-mandelic acid | 100 | d | 71.5 |

TABLE 4-continued

| Ex. | Optically active cyclic nitrogen-containing compound | Acid | Conversion (%) | Steric configuration of citronellal | Optical purity (% e.e.) |
|---|---|---|---|---|---|
| 7 | (di-4-tert-butylphenyl pyrrolidine structure) | TFA | 39.85 | l | 83.7 |
| 8 | (di-4-isopropylphenyl pyrrolidine structure) | TFA | 35.90 | l | 83.7 |

TABLE 5

| Ex. | Optically active cyclic nitrogen-containing compound | Acid | Conversion (%) | Steric configuration of citronellal | Optical purity (% e.e.) |
|---|---|---|---|---|---|
| 9 | (di-4-(1-methylcyclohexyl)phenyl pyrrolidine structure) | TFA | 91.77 | d | 83.2 |
| 10 | (di-3,5-dimethylphenyl pyrrolidine structure) | TFA | 66.72 | l | 76.9 |

TABLE 5-continued

| Ex. | Optically active cyclic nitrogen-containing compound | Acid | Conversion (%) | Steric configuration of citronellal | Optical purity (% e.e.) |
|---|---|---|---|---|---|
| 11 | (adamantyl-phenyl-phenyl-adamantyl pyrrolidine structure) | TFA | 11.44 | d | 73.4 |

TABLE 6

| Ex. | Optically active cyclic nitrogen-containing compound | Acid | Conversion (%) | Steric configuration of citronellal | Optical purity (% e.e.) |
|---|---|---|---|---|---|
| 12 | (bis(4-(2-(p-tolyl)propan-2-yl)phenyl) pyrrolidinylmethane structure) | TFA | 22.41 | d | 82.8 |
| 13 | (bis(4-(trifluoromethyl)phenyl) pyrrolidinylmethane structure) | TFA | 71.49 | l | 76.2 |

TABLE 6-continued

| Ex. | Optically active cyclic nitrogen-containing compound | Acid | Conversion (%) | Steric configuration of citronellal | Optical purity (% e.e.) |
|---|---|---|---|---|---|
| 14 | (structure: pyrrolidine with bis-(4-biphenyl)methyl substituent) | TFA | 28.24 | l | 68.8 |

Example 15

In a 50-mL reaction flask were added 2 g (13.14 mmol) of citral, 25 mg (2.5 wt % based on the citral) of 5 wt % Pd/barium sulfate, 110 mg (0.24 mmol; 5.5 wt % based on the citral) of (2R,4R)-2-(bis-(4'-t-butylphenyl)methyl)-4-(butyl-carbamoyloxy)pyrrolidine, 27.0 mg (0.24 mmol) of trifluoroacetic acid, and 2 mL of 10 wt % hydrous t-butanol. The resulting mixture was stirred and the atmosphere was changed to a hydrogen atmosphere. After stirring at 50° C. for 21 hours, the catalyst was filtered off. The residue was analyzed by gas chromatography. As a result, it was found that a conversion ratio from citral to citronellal was 78.0% and the citronellal thus obtained was a d-form and had an optical purity of 90.3% e.e.

Examples 16 to 19

In each of these examples, a reaction was conducted in a similar manner to Example 15 except that the optically active cyclic nitrogen-containing compound was changed. The optically active cyclic nitrogen-containing compound was used in an amount of 110 mg and the acid was used in an equimolar amount to the optically active cyclic nitrogen-containing compound. The results are shown in Table 7.

TABLE 7

| Ex. | Optically active cyclic nitrogen-containing compound | Acid | Conversion (%) | Steric configuration of citronellal | Optical purity (% e.e.) |
|---|---|---|---|---|---|
| 15 | (2R,4R)-2-(bis-(4'-t-butylphenyl)methyl)-4-(butylcarbamoyloxy)pyrrolidine | TFA | 78.0 | d | 90.3 |

TABLE 7-continued

| Ex. | Optically active cyclic nitrogen-containing compound | Acid | Conversion (%) | Steric configuration of citronellal | Optical purity (% e.e.) |
|---|---|---|---|---|---|
| 16 | | TFA | 98.8 | d | 89.8 |
| 17 | | TFA | 86.9 | d | 90.2 |
| 18 | | TFA | 80.3 | d | 89.4 |
| 19 | | TFA | 100 | d | 82.1 |

Example 20

In a 50-mL reaction flask were added 2 g (13.14 mmol) of citral, 25 mg (2.5 wt % based on the citral) of 5 wt % of Pd/barium sulfate, 110 mg (0.24 mmol; 5.5 wt % based on the citral) of (2R,4R)-2-(bis-(4'-t-butylphenyl)methyl)-4-(butyl-carbamoyloxy)pyrrolidine, 27.0 mg (0.24 mmol) of trifluoroacetic acid, and 2 mL of 10 wt. % hydrous t-butanol. The resulting mixture was stirred and the atmosphere was changed to a hydrogen atmosphere. After stirring at 60° C. for 21 hours, the catalyst was filtered. The residue was analyzed using gas chromatography. As a result, it was found that a conversion ratio from citral to citronellal was 100% and the citronellal thus obtained was a d-form and had an optical purity of 89.6% e.e.

Examples 21 to 25

In each of Examples, a reaction was conducted in a similar manner to Example 20 except for the change of the optically active cyclic nitrogen-containing compound. The optically active cyclic nitrogen-containing compound was used in an amount of 110 mg and the acid was used in an equimolar amount to the optically active cyclic nitrogen-containing compound. The results are shown in Tables 8 and 9.

TABLE 8

| Ex. | Optically active cyclic nitrogen-containing compound | Acid | Conversion (%) | Steric configuration of citronellal | Optical purity (% e.e.) |
|---|---|---|---|---|---|
| 20 | | TFA | 100 | d | 89.6 |
| 21 | | TFA | 100 | d | 89.2 |
| 22 | | TFA | 100 | d | 90.7 |

TABLE 9

| Ex. | Optically active cyclic nitrogen-containing compound | Acid | Conversion (%) | Steric configuration of citronellal | Optical purity (% e.e.) |
|---|---|---|---|---|---|
| 23 | (2R,4R)-2-(bis-(4'-t-butylphenyl)methyl)-4-(octylcarbamoyloxy)pyrrolidine (NHOct) | TFA | 100 | d | 89.9 |
| 24 | (2R,4R)-2-(bis-(4'-t-butylphenyl)methyl)-4-(diphenylcarbamoyloxy)pyrrolidine (NPh₂) | TFA | 100 | d | 89.7 |
| 25 | (2R,4R)-2-(diphenylmethyl)-4-(butylcarbamoyloxy)pyrrolidine (NHBu) | TFA | 100 | d | 82.1 |

Example 26

In a 50-mL reaction flask were added 2 g (13.14 mmol) of citral, 25 mg (2.5 wt % based on the citral) of 5 wt % Pd/barium sulfate, 50 mg (0.11 mmol, 2.5 wt % based on the citral) of (2R,4R)-2-(bis-(4'-t-butylphenyl)methyl)-4-(butylcarbamoyloxy)pyrrolidine, 12.3 mg (0.11 mmol) of trifluoroacetic acid, and 2 mL of 10 wt % hydrous t-butanol. The resulting mixture was stirred and the atmosphere was changed to a hydrogen atmosphere. After stirring at 60° C. for 21 hours, the catalyst was filtered off and the residue was analyzed using gas chromatography. As a result, it was found that a conversion rate from citral to citronellal was 98.9% and the citronellal thus obtained was d-form and had an optical purity of 90.5% e.e.

Example 27

A reaction was conducted in a similar manner to Example 26 except for the change of the optically active cyclic nitrogen-containing compound. The optically active cyclic nitrogen-containing compound was used in an amount of 50 mg and the acid was used in an equimolar amount to the optically active cyclic nitrogen-containing compound. The results are shown in Table 10.

TABLE 10

| Ex. | Optically active cyclic nitrogen-containing compound | Acid | Conversion (%) | Steric configuration of citronellal | Optical purity (% e.e.) |
|---|---|---|---|---|---|
| 26 | (R,R)-pyrrolidine with bis(4-tert-butylphenyl)methyl substituent and O-C(=O)NHBu carbamate | TFA | 98.9 | d | 90.5 |
| 27 | (R,R)-pyrrolidine with bis(4-tert-butylphenyl)methyl substituent and O-C(=O)NHtBu carbamate | TFA | 96.1 | d | 88.4 |

Example 28-1

Preparation of Organoaluminum Catalyst

In a nitrogen atmosphere, 493 mg (2.0 mmol) of 2,6-diphenylphenol was added in a 50-mL Schlenk flask and after purging with nitrogen, 10 mL of heptane and 0.58 mL (10 wt %, 1.00 mmol) of a methylaluminoxane-toluene solution were added successively. The resulting mixture was stirred overnight at room temperature. The solvent was then distilled off to obtain a white solid.

Figure 2:
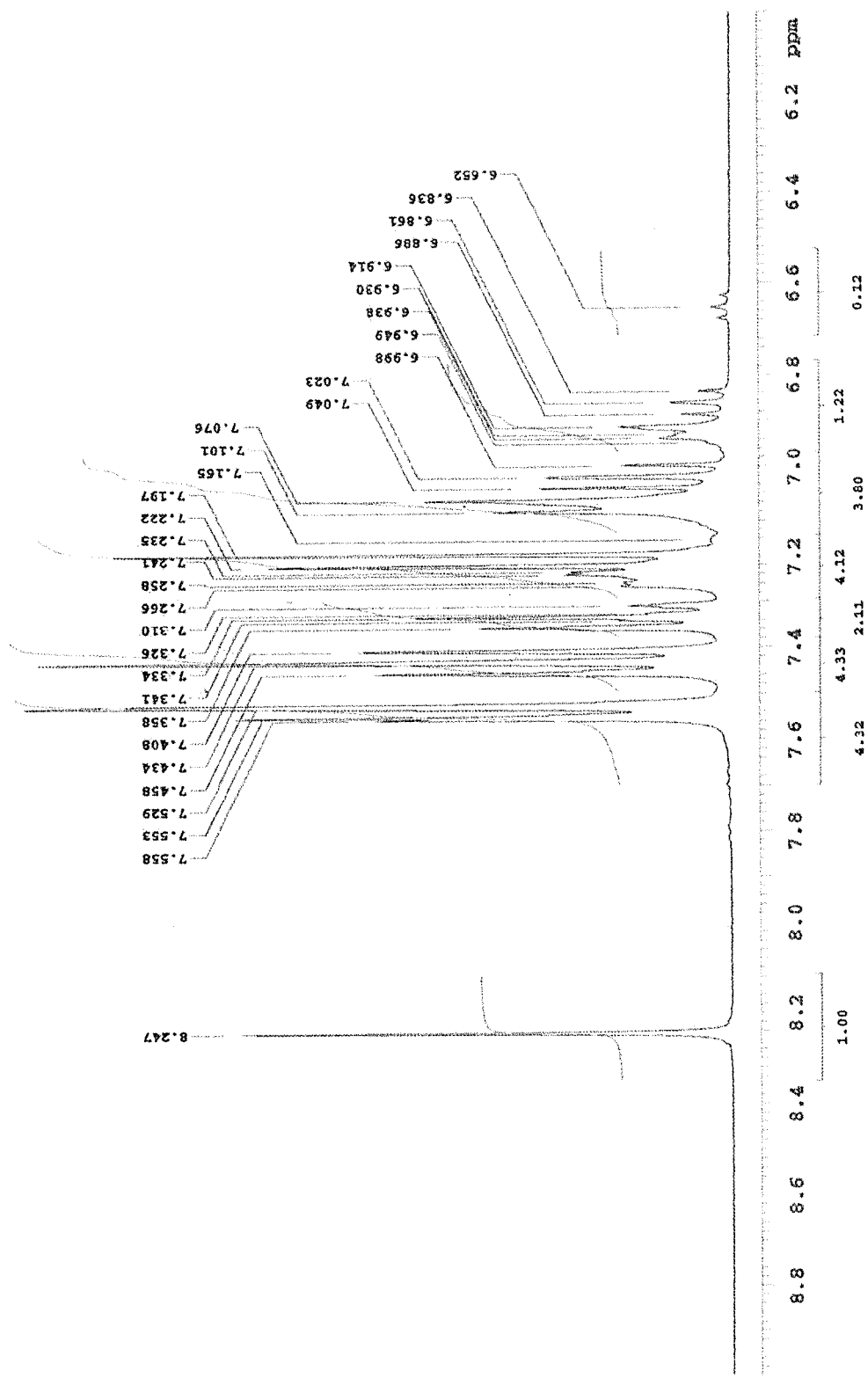
FIG. 2 is an enlarged view of a low magnetic field side of the $^1$H-NMR spectrum of a reaction product of 2,6-diphenylphenol and methylaluminoxane.
Figure 3:
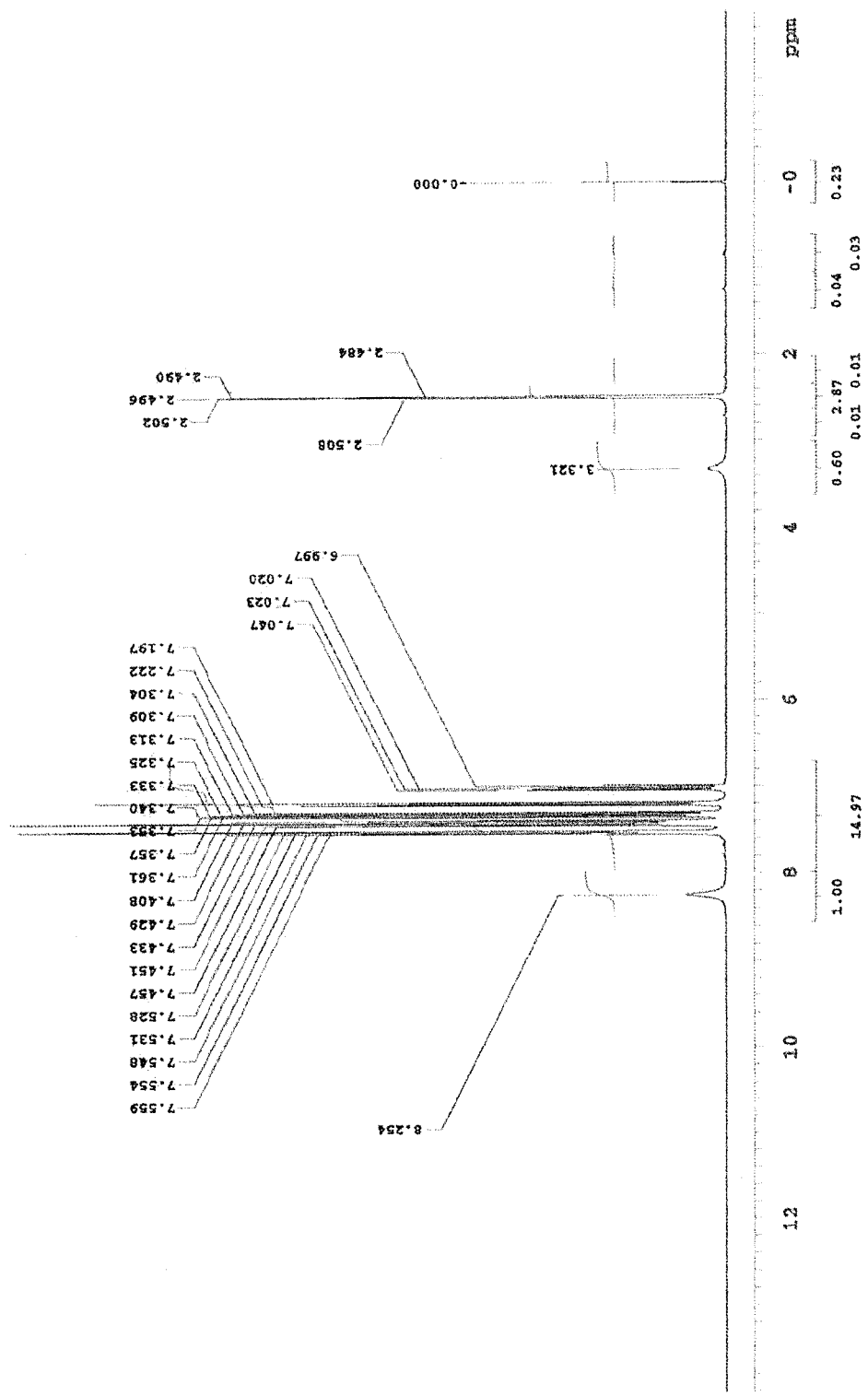
FIG. 3 is a chart showing the $^1$H-NMR spectrum of 2,6-diphenylphenol.
Figure 4:
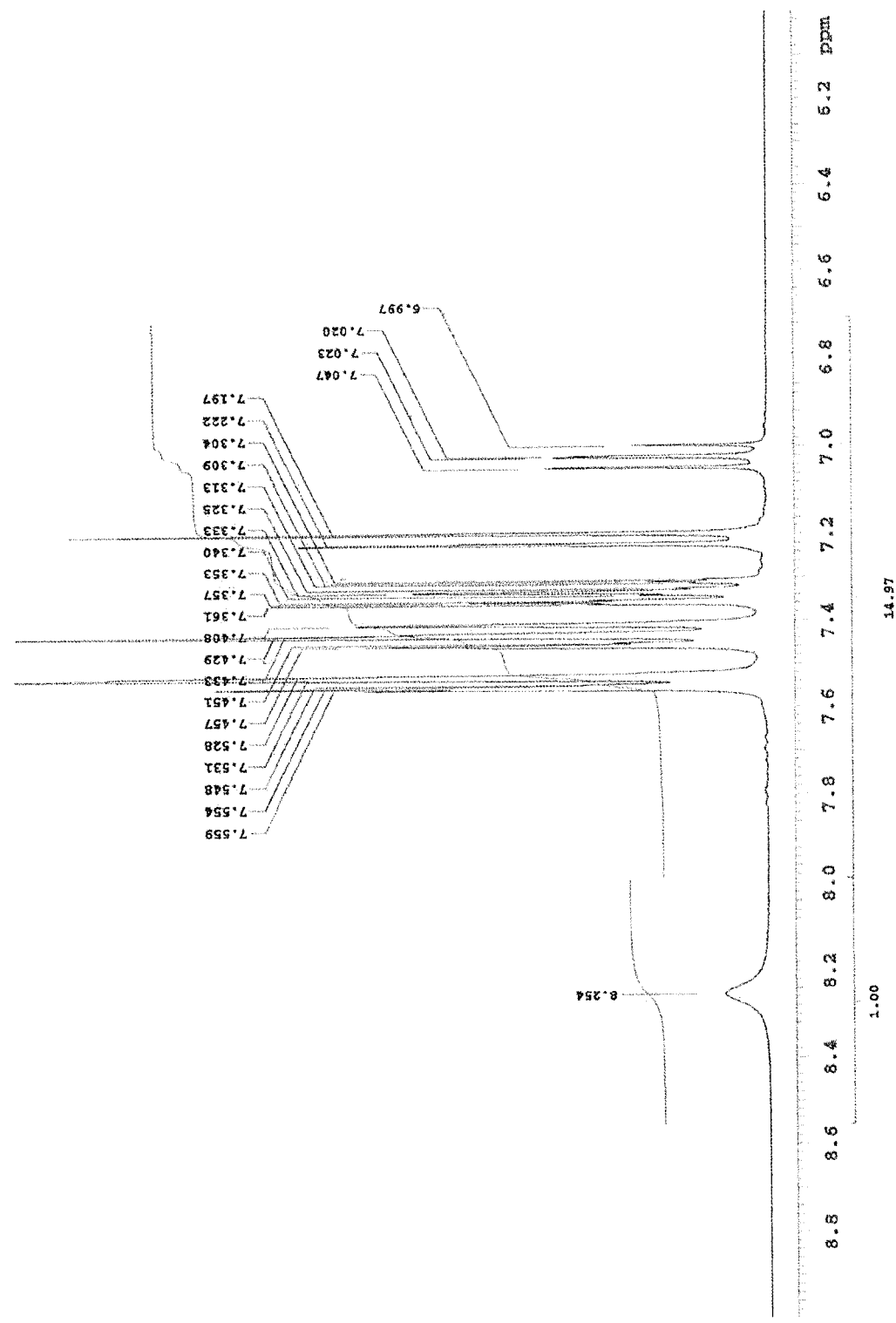
FIG. 4 is an enlarged view of a low magnetic field side of the $^1$H-NMR spectrum of 2,6-diphenylphenol.

FIG. 1 shows an $^1$H-NMR spectrum of 2,6-diphenylphenol and methylaluminoxane; FIG. 2 is an enlarged view of the low magnetic field side of the $^1$H-NMR spectrum of FIG. 1; FIG. 3 shows an $^1$H-NMR spectrum of 2,6-diphenylphenol; and FIG. 4 is an enlarged view of the low magnetic field side of the $^1$H-NMR spectrum of FIG. 3.

Example 28-2

Synthesis of 1-isopulegol ((1R,2S,5R)-isopulegol)

To the organoaluminum compound synthesized according to Example 28-1 was added 4.6 mL of toluene in a nitrogen atmosphere. The temperature in the system was cooled to from 0 to 5° C. and 1.54 g (10 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 70.5%, an isopulegol selectivity was 82.4%, and an 1-n-isopulegol:(the other isomers) ratio was 97.1:2.9.

Example 29-1

Preparation of Organoaluminum Catalyst

In a 50-mL Schlenk flask was added 197 mg (0.80 mmol) of 2,6-diphenylphenol. After purging with nitrogen, 9.3 mL of toluene and 0.12 mL (10 wt %, 0.20 mmol) of a methylaluminoxane•toluene solution were added successively. The resulting mixture was stirred at room temperature for one hour to obtain a catalyst solution.

Example 29-2

Synthesis of 1-isopulegol

After the catalyst solution obtained in Example 29-1 was cooled to from 0 to 5° C., 3.09 g (20.0 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 59.7%, an isopulegol selectivity was 87.0%, and an 1-n-isopulegol:(the other isomers) ratio was 98.1:1.9.

Example 30-1

Preparation of Organoaluminum Catalyst

In a 50-mL Schlenk flask was added 197 mg (0.60 mmol) of 2,6-diphenylphenol. After purging with nitrogen, 4.6 mL of toluene and 0.17 mL (10 wt %, 0.30 mmol) of a methylaluminoxane•toluene solution were added successively. The resulting mixture was stirred at room temperature for one hour to obtain a catalyst solution.

Example 30-2

Synthesis of 1-isopulegol

After the catalyst solution obtained in Example 30-1 was cooled to from 0 to 5° C., 1.54 g (10.0 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 82.2%, an isopulegol selectivity was 71.5%, and an 1-n-isopulegol:(the other isomers) ratio was 95.5:4.5.

Example 31-1

Preparation of Organoaluminum Catalyst

In a 50-mL Schlenk flask was added 370 mg (1.50 mmol) of 2,6-diphenylphenol. After purging with nitrogen, 4.6 mL of toluene and 0.17 mL (10 wt %, 0.30 mmol) of a methylaluminoxane•toluene solution were added successively. The resulting mixture was stirred at room temperature for one hour to obtain a catalyst solution.

Example 31-2

Synthesis of 1-isopulegol

After the catalyst solution obtained in Example 31-1 was cooled to from 0 to 5° C., 1.54 g (10.0 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 81.9%, an isopulegol selectivity was 82.0%, and an 1-n-isopulegol:(the other isomers) ratio was 96.5:3.5.

Example 32-1

Preparation of Organoaluminum Catalyst

In a 50-mL Schlenk flask was added 148 mg (0.60 mmol) of 2,6-diphenylphenol. After purging with nitrogen, 4.6 mL of toluene and 0.17 mL (10 wt %, 0.30 mmol) of a methylaluminoxane•toluene solution were added successively. The resulting mixture was stirred overnight at 40° C. to obtain a catalyst solution.

Example 32-2

Synthesis of 1-isopulegol

After the catalyst solution obtained in Example 32-1 was cooled to from 0 to 5° C., 1.54 g (10.0 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 64.8%, an isopulegol selectivity was 84.8%, and an 1-n-isopulegol:(the other isomers) ratio was 98.1:1.9.

Example 33-1

Preparation of Organoaluminum Catalyst

In a 50-mL Schlenk flask was added 370 mg (1.50 mmol) of 2,6-diphenylphenol. After purging with nitrogen, 4.6 mL of toluene and 0.17 mL (10 wt %, 0.30 mmol) of a methylaluminoxane•toluene solution were added successively. The resulting mixture was stirred overnight at 40° C. to obtain a catalyst solution.

Example 33-2

Synthesis of 1-isopulegol

After the catalyst solution obtained in Example 33-1 was cooled to from 0 to 5° C., 1.54 g (10.0 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 22.3%, an isopulegol selectivity was 84.2%, and an 1-n-isopulegol:(the other isomers) ratio was 97.6:2.4.

Example 34-1

Preparation of Organoaluminum Catalyst

In a 50-mL Schlenk flask was added 148 mg (0.60 mmol) of 2,6-diphenylphenol. After purging with nitrogen, 4.6 mL of toluene and 0.17 mL (10 wt %, 0.30 mmol) of a methylaluminoxane•toluene solution were added successively. The resulting mixture was stirred at room temperature for one hour to obtain a catalyst solution.

Example 34-2

Synthesis of d-isopulegol ((1S,2R,5S)-isopulegol)

After the catalyst solution obtained in Example 34-1 was cooled to from 0 to 5° C., 1.54 g (10.0 mmol, optical purity: 96.6% e.e.) of l-citronellal ((S)-citronellal) was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 89.2%, an isopulegol selectivity was 88.1%, and a d-n-isopulegol:(the other isomers) ratio was 96.9:3.1.

Example 35-1

Preparation of Organoaluminum Catalyst

In a 50-mL Schlenk flask was added 148 mg (0.60 mmol) of 2,6-diphenylphenol. After purging with nitrogen, 4.6 mL of methylene chloride and 0.17 mL (10 wt %, 0.30 mmol) of a methylaluminoxane•toluene solution were added successively. The resulting mixture was stirred overnight at 40° C. to obtain a catalyst solution.

Example 35-2

Synthesis of 1-isopulegol

After the catalyst solution obtained in Example 35-1 was cooled to from 0 to 5° C., 1.54 g (10.0 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 98.8%, an isopulegol selectivity was 93.3%, and an 1-n-isopulegol:(the other isomers) ratio was 98.2:1.8.

Example 36-1

Preparation of Organoaluminum Catalyst

In a 50-mL Schlenk flask was added 400 mg (0.60 mmol) of (S,S)-2,2-dimethyl-α,α,α',α'-tetra(1-naphthyl)-1,3-dioxolan-4,5-dimethanol (which may also be called hereinafter "(S,S)-1-naphthyl-TADDOL" or "(S,S)-1-NAPHTADDOL"). After purging with nitrogen, 9.3 mL of toluene and 0.35 mL (10 wt %, 0.60 mmol) of a methylaluminoxane•toluene solution were added successively. The resulting mixture was stirred at room temperature for one hour to obtain a catalyst solution.

Example 36-2

Synthesis of 1-isopulegol

After the catalyst solution obtained in Example 36-1 was cooled to from 0 to 5° C., 3.09 g (20.0 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 94.8%, an isopulegol selectivity was 91.8%, and an 1-n-isopulegol:(the other isomers) ratio was 90.8:9.2.

Example 37-1

Preparation of Organoaluminum Catalyst

In a 50-mL Schlenk flask was added 275 mg (1.60 mmol) of (R)-2,2'-dihydroxy-1,1'-binaphthyl (which may also be called "(R)-BINOL"). After purging with nitrogen, 9.3 mL of toluene and 0.35 mL (10 wt %, 0.60 mmol) of a methylaluminoxane•toluene solution were added successively and the resulting mixture was stirred overnight at 40° C. to obtain a catalyst solution.

Example 37-2

Synthesis of 1-isopulegol

After the catalyst solution obtained in Example 37-1 was cooled to from 0 to 5° C., 3.09 g (20.0 mmol, optical purity: 97.8% e.e.) of d-citronellal was added dropwise. The resulting mixture was stirred overnight at from 0 to 5° C. After completion of the reaction, 2 mL of water was added to the reaction mixture. The organic layer was analyzed using gas chromatography. As a result, it was found that a substrate conversion ratio was 83.7%, an isopulegol selectivity was 84.8%, and an 1-n-isopulegol:(the other isomers) ratio was 87.8:12.2.

Example 38-1

Preparation of Organoaluminum Catalyst

The organoaluminum catalyst was prepared according to the process described in Synlett No. 1, P57-58, 1999.

In a 200-mL reaction flask was added 9.81 g (20.0 mmol) of 3,3',5,5'-tetrabiphenyl-4,4'-diol synthesized according to the process described in Tetrahedron Letters No. 47, p 4241-4243, 1965. After purging with nitrogen, 93 mL of toluene and 12.1 mL (15 wt %, 1.1 mol/L, 13.3 mmol) of a triethylaluminum•toluene solution were added successively. The resulting mixture was exposed to ultrasound at room temperature for about 20 minutes, following filtration to obtain a light yellow solid.

Example 38-2

Synthesis of 1-isopulegol

In a 1-L reaction flask was added 10.05 g (13.2 mmol) of the catalyst obtained in Example 38-1. After purging with nitrogen, 463 mL of toluene was added in a nitrogen atmosphere and the temperature in the system was cooled to from 0 to 5° C. Then, 154.3 g (1 mol, optical purity: 97.8% e.e.) of d-citronellal was added dropwise. The resulting mixture was stirred overnight at from 0 to 5° C. After completion of the reaction, 20 mL of water was added to the reaction mixture. The organic layer was analyzed using gas chromatography. As a result, it was found that a substrate conversion ratio was 93.5%, an isopulegol selectivity was 91.2%, and an 1-n-isopulegol:(the other isomers) ratio was 98.5:1.5.

Example 39-1

Preparation of Organoaluminum Catalyst

The organoaluminum catalyst was prepared according to the process described in Synlett No. 1, P57-58, 1999.

In a 1-L reaction flask was added 11.8 g (24.0 mmol) of 3,3'5,5'-tetrabiphenyl-4,4'-diol synthesized according to the process described in Tetrahedron Letters No. 47, P4241-4243, 1965. After purging with nitrogen, 93 mL of heptane and 11.7 mL (10 wt %, 20 mmol) of a methylaluminoxane•toluene solution were added successively. The resulting mixture was exposed to ultrasound at room temperature for 2 hours. Then, the solvent was distilled off under reduced pressure to obtain a light yellow solid.

Example 39-2

Synthesis of 1-isopulegol

To the catalyst obtained in Example 39-1 was added 463 mL of toluene in a nitrogen atmosphere. The temperature in the system was cooled to from 0 to 5° C. Then, 154.3 g (1 mol, optical purity: 97.8% e.e.) of d-citronellal was added dropwise and the mixture was stirred overnight at from 0 to 5° C.

After completion of the reaction, 20 mL of water was added. The organic layer was analyzed using gas chromatography. As a result, it was found that a substrate conversion ratio was 72.8%, an isopulegol selectivity was 89.2%, and an l-n-isopulegol:(the other isomers) ratio was 96.8:3.2.

Example 40-1

Preparation of Organoaluminum Catalyst

In a nitrogen atmosphere, 286 mg (1.00 mmol) of (R)-BINOL was added in a 50-mL Schlenk flask. After purging with nitrogen, 11 mL of heptane and 0.58 mL (10 wt %, 1.00 mmol) of a methylaluminoxane•toluene solution were added successively. The resulting mixture was stirred at 40° C. for 16 hours. The solvent was then distilled off to obtain a white solid (organoaluminum compound).

Example 40-2

Synthesis of l-isopulegol

After 6 mL of heptane was added to the solid obtained in Example 40-1 in a nitrogen atmosphere, the temperature in the system was cooled to from 0 to 5° C. Then, 1.54 g (10 mmol, optical purity: 97.8% e.e.) of d-citronellal was added dropwise and the resulting mixture was stirred at from 0 to 5° C. for 2 hours. The reaction mixture was allowed to stand for 30 minutes and 4.5 mL of the supernatant was collected through a syringe. Then, 2 mL of water was added and the organic layer was analyzed using gas chromatography. As a result, it was found that a substrate conversion ratio was 99.6%, an isopulegol selectivity was 96.8%, and an l-n-isopulegol:(the other isomers) ratio was 93.4:6.6.

Example 40-3

As a second reaction, 4.5 mL of heptane was added to the residue in the Schlenk flask and the temperature in the system was cooled again to from 0 to 5° C. while re-starting stirring. To the reaction mixture was added dropwise 1.54 g (10 mmol, optical purity: 97.8% e.e.) of d-citronellal. After completion of the dropwise addition, a sample was collected and analyzed by gas chromatography. The reaction mixture was stirred again at from 0 to 5° C. for 3 hours and then, allowed to stand for 30 minutes. After collection of 4.5 mL of the supernatant through a syringe, 2 mL of water was added. The organic layer was analyzed using gas chromatography.

In the second reaction, a substrate conversion ratio in the system immediately after the dropwise addition was 38.2%, a substrate conversion ration after the three-hour reaction was 97.8%, an isopulegol selectivity was 95.7%, and an l-n-isopulegol:(the other isomers) ratio was 94.8:5.2.

Example 40-4

As a third reaction, the reaction was conducted in a similar manner to that of the second reaction.

In the third reaction, a substrate conversion ratio in the system immediately after the dropwise addition was 27.8%, a substrate conversion ration after the three-hour reaction was 96.9%, an isopulegol selectivity was 95.4%, and an l-n-isopulegol:(the other isomers) ratio was 95.1:4.9.

Example 40-5

As a fourth reaction, the reaction was conducted in a similar manner to that of the second reaction.

In the fourth reaction, a substrate conversion ratio in the system immediately after the dropwise addition was 31.1%, a substrate conversion ratio after the five-hour reaction was 92.9%, an isopulegol selectivity was 94.8%, and an l-n-isopulegol:(the other isomers) ratio was 95.5:4.5.

Example 40-6

As a fifth reaction, the reaction was conducted in a similar manner to that of the second reaction.

In the fifth reaction, a substrate conversion ratio in the system immediately after the dropwise addition was 25.4%, a substrate conversion ration after the seven-hour reaction was 90.9%, an isopulegol selectivity was 92.9%, and an l-n-isopulegol:(the other isomers) ratio was 94.5:5.5.

Example 41

Asymmetric Hydrogenation of Citral

In a 3-L reaction flask were added 500.0 g (3.28 mol) of citral, 2.50 g (0.5 wt % based on the citral) of 5 wt. % Pd/barium sulfate, 10.0 g (22.9 mmol, 2.0 wt % based on the citral) of (2R,4R)-2-(bis-(4'-t-butylphenyl)methyl)-4-(ethylcarbamoyloxy)pyrrolidine, 2.6 g (22.9 mmol) of trifluoroacetic acid, and 500 mL of 10 wt % hydrous t-butanol in a nitrogen atmosphere. The resulting mixture was stirred and the atmosphere was exchanged with a hydrogen atmosphere (0.1 MPa (atmospheric pressure)). After stirring at 60° C. for 21 hours, the catalyst was filtered off and the residue was analyzed using gas chromatography. As a result, it was found that a conversion ratio from citral to citronellal was 99.4% and an optical purity was 90.9% e.e. The crude-citronellal thus obtained was distilled to obtain 398 g (2.58 mol, yield: 78.6%) of d-citronellal having a purity of 98%.

Example 42

Ring-Closure Reaction of d-Citronellal

In a 1-L four-necked flask were added 308.5 g (2.0 mol) of the d-citronellal obtained in Example 41, 15.26 g (20 mmol) of a tris(2,6-diphenylphenoxy)aluminum catalyst described in Patent Document 6, and 300 mL of toluene in a nitrogen atmosphere. The resulting mixture was stirred at 5° C. for 5 hours. The reaction mixture was then distilled to obtain 276.5 g (1.79 mol, yield: 89.6%) of l-isopulegol (99.5% n-form, 90.6% e.e.).

Example 43

Hydrogenation Reaction of l-Isopulegol, Synthesis of l-Menthol

In a 500-mL autoclave were added 100.0 g (0.65 mol) of the l-isopulegol obtained in Example 42 and 0.4 g of Raney nickel in a nitrogen atmosphere. Hydrogenation was conducted under a hydrogen pressure of 2.5 MPa at 70° C. for 10 hours. The reaction mixture was filtered and the residue was distilled to obtain 92.3 g (0.59 mol, 90% e.e.) of l-menthol.

Example 44

Deep Cooling Crystallization of l-Isopulegol

In a 1-L separable flask were added 154.3 g (1.00 mol) of the l-isopulegol obtained in Example 42 and 154 mL of heptane in a nitrogen atmosphere. The resulting mixture was cooled gradually to −13° C. After precipitation of the crystals of isopulegol was confirmed, cooling was conducted further to −44° C. The crystals thus precipitated were separated by suction filtration. Then, the crystals thus obtained were dissolved, the solvent was collected, and the residue was distilled to obtain 117.3 g (0.76 mol, yield: 76.0%) of high-purity 1-isopulegol (100% n-form, 100% e.e.).

Example 45

Hydrogenation Reaction of High-Purity 1-Isopulegol and Synthesis of High-Purity 1-Menthol In a 500-mL autoclave were added 100.0 g (0.65 mol) of the 1-isopulegol obtained in Example 44 and 0.4 g of Raney nickel in a nitrogen atmosphere. Hydrogenation was conducted at a hydrogen pressure of 2.5 MPa and 70° C. for 10 hours. The reaction mixture was filtered, followed by distillation to obtain 94.8 g (0.61 mol, 100% e.e.) of 1-menthol.

The present invention has been described in detail and with reference to specific embodiments thereof. It will be apparent for those skilled in the art that various changes and modifications can be made without departing from the spirit and scope of the present invention. This application is based on Japanese Patent Application No. 2010-268633 filed on Dec. 1, 2010, and their contents are incorporated herein by reference.

INDUSTRIAL APPLICABILITY

The asymmetric hydrogenation catalyst used in the present invention, which has been obtained only by mixing a metal powder or a metal-supported substance, an optically active cyclic nitrogen-containing compound, and an acid, can asymmetrically hydrogenate geranial, neral, or citral (a mixture of geranial and neral in any ratio) easily and simply to prepare an optically active citronellal.

The catalyst used for the ring-closure reaction of citronellal in the present invention, which has been obtained only by mixing an alkyl aluminum compound and a specific alcohol, can ring-close citronellal and an optically active citronellal easily and simply to prepare a high n-selectivity isopulegol and an optically active isopulegol, respectively.

The resulting optically active isopulegol not subjected to deep cooling crystallization or a high-purity optically active isopulegol obtained by deep cooling crystallization of the resulting optically active isopulegol is hydrogenated with a conventional carbon-carbon double bond hydrogenation catalyst to prepare optically active menthol.

Thus, the method for manufacturing an optically active menthol according to the present invention is comprised of fewer steps and these steps are all comprised of a step of a catalyst reaction. This production method therefore generates less environmentally contaminating waste and can save a production cost.

In addition, the production method is industrially advantageous because as all the catalysts used in the present invention, those not soluble in a reaction mixture can be used so that the metal or metal-supported substance, optically active cyclic nitrogen-containing compound, and ring closing catalyst and ligand therefor can be easily recovered from the reaction system and provided for re-use.

The invention claimed is:

1. A method for manufacturing an optically active menthol, comprising the following steps:
   A-1) asymmetrically hydrogenating at least one of geranial and neral to thereby obtain an optically active citronellal, wherein a hydrogen gas, and a catalyst containing: at least one of a transition metal; an optically active cyclic nitrogen-containing compound; and an acid, are used,
   B-1) conducting a ring-closure reaction of the optically active citronellal in the presence of an acid catalyst to thereby obtain an optically active isopulegol, and
   C-1) hydrogenating the optically active isopulegol to thereby obtain an optically active menthol.

2. The method for manufacturing an optically active menthol according to claim 1, comprising the following steps:
   A-5) asymmetrically hydrogenating at least one of geranial and neral to thereby obtain an optically active citronellal having an optical purity of from 70 to 99% e.e.,
   B-5) conducting a ring-closure reaction of the optically active citronellal in the presence of an acid catalyst to thereby obtain an optically active isopulegol, and
   C-5) hydrogenating the optically active isopulegol to thereby obtain an optically active menthol.

3. The method for manufacturing an optically active menthol according to claim 1, comprising the following steps:
   A-9) asymmetrically hydrogenating at least one of geranial and neral to thereby obtain d-citronellal,
   B-9) conducting a ring-closure reaction of the d-citronellal in the presence of an acid catalyst to thereby obtain 1-isopulegol, and
   C-9) hydrogenating the 1-isopulegol to thereby obtain 1-menthol.

4. The method for manufacturing an optically active menthol according to claim 1, comprising the following steps:
   A-13) asymmetrically hydrogenating at least one of geranial and neral to thereby obtain d-citronellal having an optical purity of from 70 to 99% e.e.,
   B-13) conducting a ring-closure reaction of the d-citronellal in the presence of an acid catalyst to thereby obtain 1-isopulegol having an optical purity of from 70 to 99% e.e., and
   C-13) hydrogenating the 1-isopulegol to thereby obtain 1-menthol having an optical purity of from 70 to 99% e.e.

5. The method for manufacturing an optically active menthol according to claim 1, wherein the metal is selected from the group consisting of nickel, ruthenium, rhodium, iridium, palladium and platinum.

6. The method for manufacturing an optically active menthol according to claim 1, wherein the acid catalyst in the ring-closure reaction of the optically active citronellal in step B is a Lewis acid aluminum catalyst.

7. The method for manufacturing an optically active menthol according to claim 6, wherein the Lewis acid aluminum catalyst is an organoaluminum compound obtained by reacting:
   a trialkylaluminum of the following formula (3),
   with at least one compound selected from the group consisting of 2,6-diphenylphenol of the following structure (4), 2,6,2',6'-tetraphenyl-biphenyl-4,4'-diol of the following structure (5), 1,1'-binaphthyl-2,2'-diol of the following structure (6) which may be optically active, and (2,2-dimethyl-1,3-dioxolan-4,5-diyl)bis(diphenylmethanol) which may be optically active and is of the following structure (7):

$$(R^{13})_3Al \qquad (3)$$

[in the formula (3), $R^{13}$ represents an alkyl group having from 1 to 8 carbon atoms]

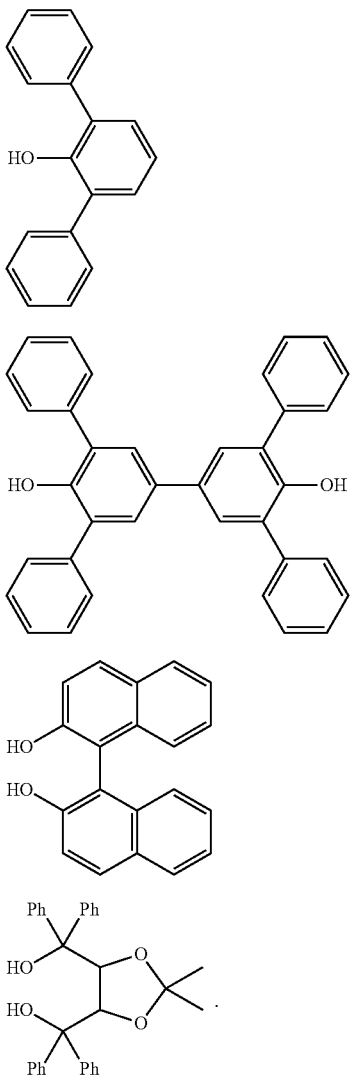

(4)

(5)

(6)

(7)

8. The method for manufacturing an optically active menthol according to claim 6, wherein the Lewis acid aluminum catalyst is an organoaluminum catalyst obtained by reacting:
    at least one organoaluminumoxy compound selected from the group consisting of a chain alminoxane of the following formula (8), a cyclic aluminoxane of the following formula (9) and a bis(dialkylaluminumoxy)alkylborane of the following formula (10),
    with at least one hydroxy compound selected from the group consisting of a diarylphenol of the following formula (11), a bis(diarylphenol) of the following formula (12), a biaryldiol of the following formula (13), a dimethanol of the following formula (14), and a silanol of the following formula (15):

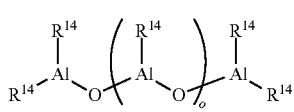

(8)

[in the formula (8), $R^{14}$ represents an alkyl group having from 1 to 6 carbon atoms, an alicyclic group having from 5 to 8 carbon atoms, or an aralkyl group which has from 7 to 12 carbon atoms and may have a substituent group, and a plurality of $R^{14}$ may be the same or different from each other; and o represents an integer of from 0 to 40];

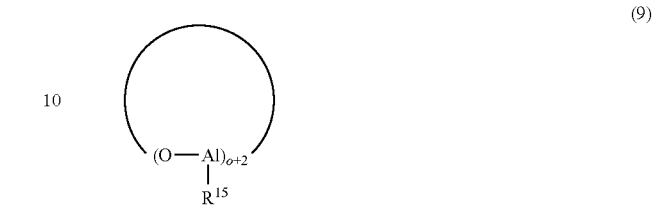

(9)

[in the formula (9), $R^{15}$ represents an alkyl group having from 1 to 6 carbon atoms, an alicyclic group having from 5 to 8 carbon atoms, or an aralkyl group which has from 7 to 12 carbon atoms and may have a substituent group; and o represents an integer of from 0 to 40];

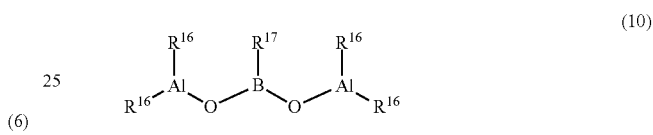

(10)

[in the formula (10), $R^{16}$ represents an alkyl group having from 1 to 6 carbon atoms, an alicyclic group having from 5 to 8 carbon atoms, or an aralkyl group which has from 7 to 12 carbon atoms and may have a substituent group, and a plurality of $R^{16}$ may be the same or different from each other; and $R^{17}$ represents an alkyl group having from 1 to 6 carbon atoms, an alicyclic group having from 5 to 8 carbon atoms, or an aralkyl group which has from 7 to 12 carbon atoms and may have a substituent group];

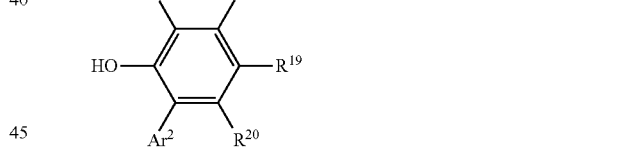

(11)

[in the formula (11), $Ar^1$ and $Ar^2$ each independently represent an aryl group which has from 6 to 15 carbon atoms and may have a substituent group or a heteroaryl group which has from 2 to 15 carbon atoms and may have a substituent group; $R^{18}$, $R^{19}$, and $R^{20}$ each independently represent a hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group, or a polymer chain; and $R^{18}$ and $R^{19}$, or $R^{19}$ and $R^{20}$ may be bonded to each other to independently form a fused benzene ring, a fused substituted benzene ring, a trimethylene group, a tetramethylene group, a pentamethylene group, a methylenedioxy group, an ethylenedioxy group or a trimethylenedioxy group];

(12)

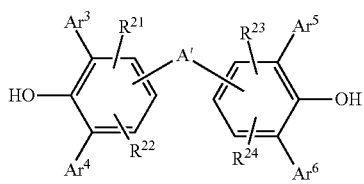

[in the formula (12), $Ar^3$, $Ar^4$, $Ar^5$, and $Ar^6$ each independently represent an aryl group which has from 6 to 15 carbon atoms and may have a substituent group or a heteroaryl group which has from 2 to 15 carbon atoms and may have a substituent group;

$R^{21}$, $R^{22}$, $R^{23}$ and $R^{24}$ each independently represent a hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group or a polymer chain; and $R^{21}$ and $R^{22}$, or $R^{23}$ and $R^{24}$ may be bonded to each other to independently form a fused benzene ring, a fused substituted benzene ring, a trimethylene group, a tetramethylene group, a pentamethylene group, a methylenedioxy group, an ethylenedioxy group or a trimethylenedioxy group; $R^{21}$ or $R^{22}$ and/or $R^{23}$ or $R^{24}$ may be bonded to A' to form an aromatic ring or a non-aromatic ring;

A' represents (1) a linear or branched and/or cyclic hydrocarbon group having from 1 to 25 carbon atoms, which may have at least one of a substituent group and an unsaturated bond; (2) an arylene group which has from 6 to 15 carbon atoms and may have a substituent group; (3) a heteroarylene group which has from 2 to 15 carbon atoms and may have a substituent group; or (4) a functional group or hetero element selected from the group consisting of —O—, —S—, —N($R^{25}$)—, —S(O)—, —C(O)—, —S(O)$_2$—, —P($R^{25}$)—, —($R^{25}$)P(O)— and —Si($R^{26}R^{27}$)— (wherein, $R^{25}$ to $R^{27}$ each independently represent an alkyl group having from 1 to 6 carbon atoms, an alicyclic group having from 5 to 8 carbon atoms, an aralkyl group which has from 7 to 12 carbon atoms and may have a substituent group, or an aryl group which has from 6 to 10 carbon atoms and may have a substituent group)];

(13)

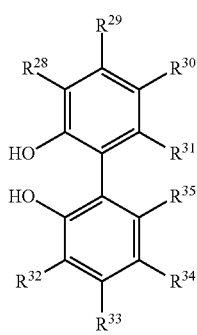

[in the formula (13), $R^{28}$, $R^{29}$, $R^{30}$, $R^{31}$, $R^{32}$, $R^{33}$, $R^{34}$, and $R^{35}$ each independently represent a hydrogen atom, an alkyl group having from 1 to 8 carbon atoms, a perfluoroalkyl group having from 1 to 4 carbon atoms, an alkoxy group having from 1 to 8 carbon atoms, an alicyclic group having from 5 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a dialkylamino group having from 2 to 8 carbon atoms, a thioalkoxy group having from 1 to 4 carbon atoms, a nitro group or a polymer chain; and $R^{28}$ and $R^{29}$, $R^{29}$ and $R^{30}$, $R^{30}$ and $R^{31}$, $R^{31}$ and $R^{35}$, $R^{32}$ and $R^{33}$, $R^{33}$ and $R^{34}$, or $R^{34}$ and $R^{35}$ may be bonded to each other to independently form a fused benzene ring, a fused substituted benzene ring, a trimethylene group, a tetramethylene group, a pentamethylene group, a methylenedioxy group, an ethylenedioxy group, or a trimethylenedioxy group];

(14)

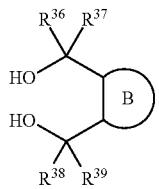

[in the formula (14), $R^{36}$, $R^{37}$, $R^{38}$, and $R^{39}$ each independently represent a hydrogen atom, an alkyl group having from 1 to 8 carbon atoms, an alicyclic group having from 5 to 8 carbon atoms, a perhalogenoalkyl group having from 1 to 8 carbon atoms, an alkoxy group having from 1 to 8 carbon atoms, an aralkyl group which has from 7 to 12 carbon atoms and may have a substituent group, a halogen atom, an organosilyl group, an aryl group which has from 6 to 15 carbon atoms and may have a substituent group, a heteroaryl group which has from 2 to 15 carbon atoms and may have a substituent group, a dialkylamino group having from 2 to 8 carbon atoms, a thioalkoxy group having from 1 to 4 carbon atoms, a nitro group or a polymer chain; and $R^{36}$ and $R^{37}$, and $R^{38}$ and $R^{39}$ may be bonded to each other to independently form a 3- to 9-membered ring which may have a hetero element; and ring B is a 3- to 8-membered ring which may have a hetero element];

(15)

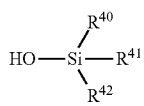

[in the formula (15), $R^{40}$, $R^{41}$, and $R^{42}$ each independently represent an alkyl group having from 1 to 10 carbon atoms, an alicyclic group having from 5 to 8 carbon atoms, an aralkyl group having from 7 to 12 carbon atoms, an aryl group which has from 6 to 10 carbon atoms and may have a substituent group, a heteroaryl group which has from 2 to 15 carbon atoms and may have a substituent group, or a polymer chain].

9. The method for manufacturing an optically active menthol according to claim 6, wherein the Lewis acid aluminum catalyst is an organoaluminum catalyst obtained by reacting:
a chain aluminoxane of the following formula (8),
with at least one compound selected from the group consisting of a 2,6-di-phenylphenol of the following structure (4), 2,6,2',6'-tetraphenyl-biphenyl-4,4'-diol of the following structure (5), and 1,1'-binaphthyl-2,2'-diol which may be optically active and is of the following structure (6):

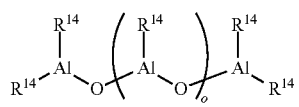
(8)

[in the formula (8), $R^{14}$ represents an alkyl group having from 1 to 6 carbon atoms, an alicyclic group having from 5 to 8 carbon atoms, or an aralkyl group which has from 7 to 12 carbon atoms and may have a substituent group; and a plurality of $R^{14}$ may be the same or different from each other; and o represents an integer of from 0 to 40]

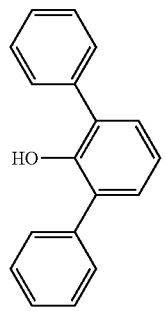
(4)

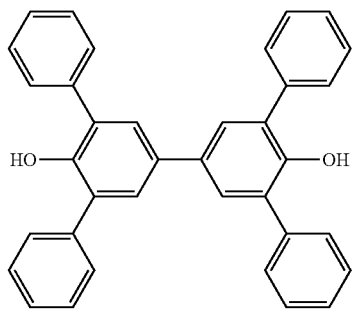
(5)

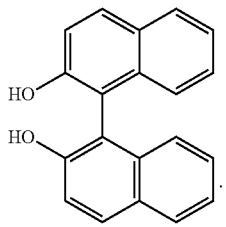
(6)

* * * * *